(12) United States Patent
Shapiro et al.

(10) Patent No.: US 7,528,260 B2
(45) Date of Patent: May 5, 2009

(54) METHOD FOR PREPARING N-PHENYLPYRAZOLE-1-CARBOXAMIDES

(75) Inventors: Rafael Shapiro, Wilmington, DE (US); Eric de Guyon Taylor, Newark, DE (US); William T. Zimmerman, Landenberg, PA (US)

(73) Assignee: E. I. du Pont de Nemours and Company, Wilmington, DE (US)

( * ) Notice: Subject to any disclaimer, the term of this patent is extended or adjusted under 35 U.S.C. 154(b) by 0 days.

(21) Appl. No.: 11/666,920

(22) PCT Filed: Dec. 6, 2005

(86) PCT No.: PCT/US2005/044131

§ 371 (c)(1),
(2), (4) Date: May 3, 2007

(87) PCT Pub. No.: WO2006/062978

PCT Pub. Date: Jun. 15, 2006

(65) Prior Publication Data

US 2007/0299265 A1 Dec. 27, 2007

Related U.S. Application Data

(60) Provisional application No. 60/633,899, filed on Dec. 7, 2004.

(51) Int. Cl.
- C07C 229/58 (2006.01)
- C07C 259/04 (2006.01)
- C07D 231/00 (2006.01)
- C07D 213/08 (2006.01)

(52) U.S. Cl. ............... 548/374.1; 548/356.1; 548/364.1; 548/373.1; 562/458; 562/621; 562/622; 562/800; 546/249; 546/250

(58) Field of Classification Search ............... 546/200, 546/249, 250; 548/200, 356.1, 364.1, 373.1, 548/374.1; 562/458, 621, 622, 800
See application file for complete search history.

(56) References Cited

U.S. PATENT DOCUMENTS

| | | | |
|---|---|---|---|
| 3,739,009 A | 6/1973 | Junge et al. | |
| 3,835,189 A | 9/1974 | Arsura et al. | |
| 3,840,540 A | 10/1974 | Dominy et al. | |
| 3,843,791 A | 10/1974 | McFarland | |
| 4,137,325 A | 1/1979 | Sellstedt et al. | |
| 4,421,931 A | 12/1983 | Tonne et al. | |
| 7,241,767 B2 | 7/2007 | Clark et al. | |

FOREIGN PATENT DOCUMENTS

| | | | |
|---|---|---|---|
| EP | 57424 | | 8/1982 |
| EP | 1 423 379 B1 | | 5/2008 |
| GB | 1178322 | * | 1/1970 |
| GB | 1 410 178 | | 10/1975 |
| GB | 1377275 | | 12/1994 |
| IT | 869213 | | 7/1970 |
| JP | 57167464 | | 10/1982 |
| WO | 93/20038 A1 | | 10/1993 |
| WO | 01/70671 A1 | | 9/2001 |
| WO | 03/015518 A1 | | 2/2003 |
| WO | 03/015519 A1 | | 2/2003 |
| WO | 03/016300 A1 | | 2/2003 |
| WO | 03/062226 A1 | | 7/2003 |
| WO | 2004/011447 A1 | | 2/2004 |
| WO | WO 2004/046129 | * | 6/2004 |
| WO | 2004/067528 A1 | | 9/2004 |
| WO | 2004/111030 A1 | | 12/2004 |

OTHER PUBLICATIONS

Sheibley (Sheibley, Fred E. "The Interaction of 5, 7- Dibromoisatoic Anhydride with Aniline." The Journal of Organic Chemistry 17(2) (1951): 221-225).*

(Continued)

*Primary Examiner*—Kamal A Saeed
*Assistant Examiner*—Samantha L Shterengarts

(57) ABSTRACT

A method is disclosed for preparing compounds of Formula 1 by combining compounds of Formulae 2 and 3 and a sulfonyl chloride.

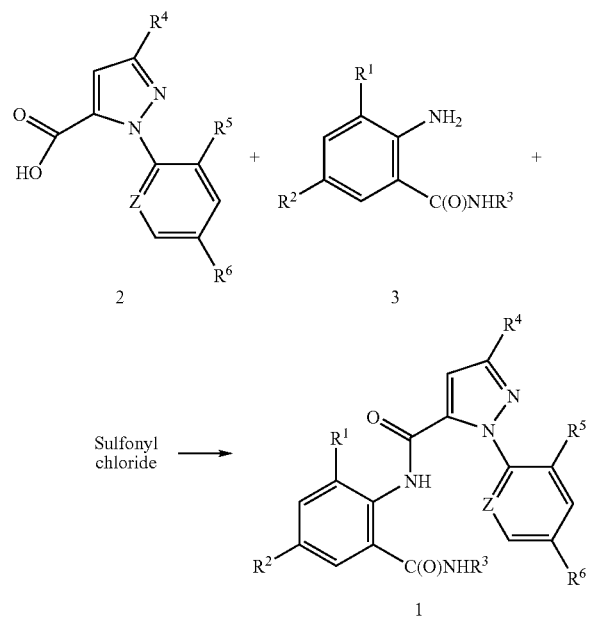

Also disclosed are compounds of Formula 3, which are useful as starting materials for this method.

16 Claims, No Drawings

OTHER PUBLICATIONS

Sheibley, Fred E. "6, 8- Diiodobenzoyleneurea, and the Interaction of 5, 7- Dihalogenoisatoic Anhydrides with Ammonia and with Ethylamine. 3-Ethyl-6, 8- Dihalogenobenzoyleneureas." The Journal of Organic Chemistry 3(5) (1946): 743-751.*

Sheibley et al., 6,8-Diiodobenzoyleneurea and the Interaction of 5,7-Dihalogenoisatoic Anhydrides With Ammonia and With Ethylamine . 3-Ethyl-6,8-Dihalogenobenzoyleneureas, J. Organic Chemistry, 1947, vol. 12:743-751.

J. H. Brewster et al., Dehydrations With Aromatic Sulfonyl Halides in Pyridine, A Convenient Method for the Preparation of Esters, J. Am. Chem. Soc., 1955, vol. 77:6214-6215.

G. E. Keck et al., Synthetic Studies on Lycoricidine. II. An Efficient Route to CIS Dihydrolycoricidine, Tetrahedron Lett., 1981, vol. 22:2615-2618.

J. Urbanski et al., Acylation of Primary and Secondary Amines With Carboxylic Acids in Presence of Aromatic Sulfochlorides and Tertiary Amines, Polish J. Chem., 1983, pp. 603-605.

L. Toke et al., Phase-Transfer Catalyzed Synthesis of Amides and Esters of Carboxlic Acids, Synthesis, 1989, pp. 745-747.

K. Kojima et al., A Facile Synthesis of a Sterically Congested Amide: A Convenient Method of Steroidal 17B-Amide Synthesis From 17B-Carboxylic Acid and a Hindered Amine With 2,4,6-Triisopropylbenzenesulfonyl Chloride as a Condensing Reagent, Synlett., 1996, pp. 517-518.

T. B. Wei et al., Facile and Effective Synthesis of N-Aryl-2-Furancarboxamides Derivatives Under the Condition of Phase Transfer Catalysis, Synthetic Commun., 1999, vol. 29:2943-2947.

A. Baruffini et al., The Selective Phytotoxic Activity of N, N-di,sec. Butylamides of Aminobenzoic Acids That are Mono-, Di-, and Trisubstituted in (on) the Nucleus, Farmaco, Edizione Scientifica, 1978, vol. 33:201-221.

W. Kosbahn et al., A Novel Heteroaromatic System: 2,1,3-Benzothiadiazinylium Derivatives, Angewante Chemie, 1977, vol. 16:780-781.

B. W. Horrom et al., The Anticonvulsant Properties of Some Benzamides, J. Medicinal Chemistry, 1963, vol. 6:528-532.

B. Altenkirk et al., Reactions of Tert-Butyl Hypochlorite. IV. The Reaction Between Tert-Butyl Hypochlorite and Benzamides, J. Organic Chemistry, 1962, vol. 27:4532-4534.

S. M. Gadekar et al., Some Halogenated 1,2,3-Benzotriazin - 4(3H)Ones, J. Organic Chemistry, 1961, vol. 26:613-615.

F. E. Sheibley et al., 6,8-Dichlorobenzoylene Urea and the Interaction of 5,7-Dihalogen Isatoic Anhydrides With Ammonia,—A New Reagent for Sodium, J. Organic Chemistry, 1938, vol. 3, pp. 414-423.

Abstract RE JP 57167464.

Abstract RE EP 57424.

* cited by examiner

METHOD FOR PREPARING N-PHENYLPYRAZOLE-1-CARBOXAMIDES

This application represents a national filing under 35 U.S.C. 371 of International Application No. PCT/US2005/044,131 filed Dec. 6, 2005, claiming priority of U.S. Application No. 60/633,899 filed Dec. 7, 2004.

FIELD OF THE INVENTION

This invention relates to a method for preparing N-phenylpyrazole-1-carboxamides by coupling carboxylic acids with anthranilamides and to anthranilamide compounds suitable for the method.

BACKGROUND OF THE INVENTION

PCT Patent Publication WO 03/015518 discloses the utility of N-acyl anthranilic acid derivatives of Formula i as arthropodicides

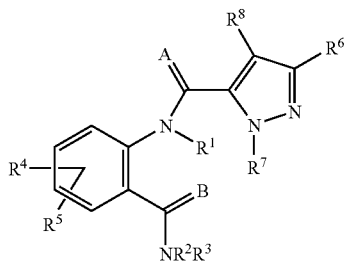

i wherein A and B are independently O or S; $R^1$ is H; $R^2$ is H, $C_1$-$C_6$ alkyl, $C_2$-$C_6$ alkoxycarbonyl or $C_2$-$C_6$ alkylcarbonyl; $R^3$ is, inter alia, H or $C_1$-$C_6$ alkyl; $R^4$ is, inter alia, H or $C_1$-$C_6$ alkyl; $R^5$ is H, $C_1$-$C_6$ alkyl or halogen; $R^6$ is H, $C_1$-$C_6$ alkyl, $C_1$-$C_6$ haloalkyl, halogen, CN, $C_1$-$C_4$ alkoxy or $C_1$-$C_4$ haloalkoxy; $R^7$ is, inter alia, a phenyl ring, a benzyl ring, a 5- or 6-membered heteroaromatic ring, a napththyl ring system, each ring or ring system optionally substituted with 1-3 substituents; and $R^8$ is, inter alia, H. This reference discloses several methods to prepare compounds of Formula i. However, the need continues for new methods that are less costly, more efficient, more flexible, or more convenient to operate.

SUMMARY OF THE INVENTION

This invention is directed to a method for preparing a compound of Formula 1,

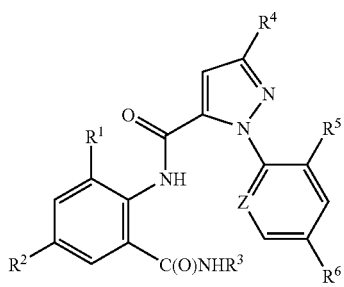

1 wherein
$R^1$ is $CH_3$ or Cl;
$R^2$ is Br, Cl, I or CN;
$R^3$ is H or $C_1$-$C_4$ alkyl;
$R^4$ is Cl, Br, $CF_3$, $OCF_2H$ or $OCH_2CF_3$;
$R^5$ is F, Cl or Br;
$R^6$ is H, F or Cl;
Z is $CR^7$ or N; and
$R^7$ is H, F, Cl or Br.

The method comprises combining (1) a carboxylic acid compound of Formula 2,

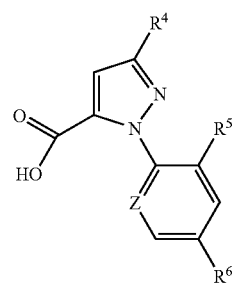

2

(2) an aniline compound of Formula 3,

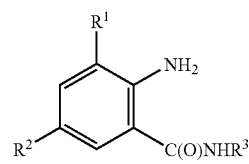

3 and (3) a sulfonyl chloride to form the compound of Formula 1.

This invention is also directed to an aniline compound of Formula 3 wherein
$R^1$ is $CH_3$ or Cl;
$R^2$ is Br, Cl, I or CN; and
$R^3$ is H or $C_1$-$C_4$ alkyl;

provided that
(a) when $R^1$ and $R^2$ are Cl, then $R^3$ is other than H, $CH_2CH_3$, or $CH(CH_3)CH_2CH_3$;
(b) when $R^1$ is $CH_3$ and $R^2$ is Cl, Br or CN, then $R^3$ is other than $CH_3$ or $CH(CH_3)_2$;
(c) when $R^1$ is Cl and $R^2$ is Cl or Br, then $R^3$ is other than $CH_3$ or $CH(CH_3)_2$; and
(d) when $R^1$ is $CH_3$ and $R^2$ is CN, then $R_3$ is other than H.

DETAILED DESCRIPTION OF THE INVENTION

As used herein, the terms "comprises," "comprising," "includes," "including," "has," "having" or any other variation thereof, are intended to cover a non-exclusive inclusion. For example, a composition, process, method, article, or apparatus that comprises a list of elements is not necessarily limited to only those elements but may include other elements not expressly listed or inherent to such composition, process, method, article, or apparatus. Further, unless expressly stated to the contrary, "or" refers to an inclusive or and not to an exclusive or. For example, a condition A or B is satisfied by any one of the following: A is true (or present) and B is false (or not present), A is false (or not present) and B is true (or present), and both A and B are true (or present).

Combining chemicals refers to contacting the chemicals with each other.

Also, the indefinite articles "a" and "an" preceding an element or component of the invention are intended to be nonrestrictive regarding the number of instances (i.e. occurrences) of the element or component. Therefore "a" or "an" should be read to include one or at least one, and the singular word form of the element or component also includes the plural unless the number is obviously meant to be singular.

Carbon-based radical refers to a monovalent molecular component comprising a carbon atom that connects the radical to the remainder of the chemical structure through a single bond. Carbon-based radicals can optionally comprise saturated, unsaturated and aromatic groups, chains, rings and ring systems, and heteroatoms. Although carbon-based radicals are not subject to any particular limit in size, in the context of the present invention they typically comprise 1 to 16 carbon atoms and 0 to 3 heteroatoms. Of note are carbon-based radicals selected from $C_1$-$C_6$ alkyl, $C_1$-$C_4$ haloalkyl and phenyl optionally substituted with 1-3 substituents selected from $C_1$-$C_3$ alkyl, halogen and nitro.

In the recitations herein, the abbreviation "Ph" means phenyl. Alkyl can be straight chain or branched. The term "halogen", either alone or in compound words such as "haloalkyl", includes fluorine, chlorine, bromine or iodine. Further, when used in compound words such as "haloalkyl", said alkyl may be partially or fully substituted with halogen atoms which may be the same or different. Examples of "haloalkyl" include $F_3C$, $ClCH_2$, $CF_3CH_2$ and $CF_3CCl_2$.

Embodiments Of The Present Invention Include:

Embodiment M1. The method wherein the molar ratio of the compound of Formula 2 to the compound of Formula 3 is from about 1.2:1 to about 1:1.2.

Embodiment M2. The method of Embodiment M1 wherein the molar ratio of the compound of Formula 2 to the compound of Formula 3 is from about 1:1 to about 1:1.2.

Embodiment M3. The method of Embodiment M2 wherein the molar ratio of the compound of Formula 2 to the compound of Formula 3 is about 1:1.1.

Embodiment M4. The method wherein the molar ratio of the sulfonyl chloride to the compound of Formula 2 is at least about 1:1.

Embodiment M5. The method of Embodiment M4 wherein the molar ratio of the sulfonyl chloride to the compound of Formula 2 is from about 1:1 to about 2.5:1.

Embodiment M6. The method of Embodiment M5 wherein the molar ratio of the sulfonyl chloride to the compound of Formula 2 is from about 1.1:1 to about 1.4:1.

Embodiment M7. The method of Embodiment M6 wherein when $R^2$ is Br, Cl or I, then the molar ratio of the sulfonyl chloride to the compound of Formula 2 is about 1.2:1.

Embodiment M8. The method of Embodiment M6 wherein when $R^2$ is CN, then the molar ratio of the sulfonyl chloride to the compound of Formula 2 is about 1.4:1.

Embodiment M9. The method wherein the sulfonyl chloride is of Formula 4

$$R^8S(O)_2Cl \qquad 4$$

wherein $R^8$ is a carbon-based radical.

Embodiment M10. The method of Embodiment M9 wherein $R^8$ is $C_1$-$C_4$ alkyl, $C_1$-$C_2$ haloalkyl, or phenyl optionally substituted with 1-3 substituents selected from the group consisting of halogen, $C_1$-$C_3$ alkyl and nitro.

Embodiment M11. The method of Embodiment M10 wherein $R^8$ is $C_1$-$C_2$ alkyl, $CF_3$, phenyl or 4-methylphenyl.

Embodiment M12. The method of Embodiment M11 wherein $R^8$ is $C_1$-$C_2$ alkyl, phenyl or 4-methylphenyl.

Embodiment M13. The method of Embodiment M12 wherein $R^8$ is $CH_3$.

Embodiment M14. The method wherein the carboxylic acid of Formula 2, aniline of Formula 3 and sulfonyl chloride are combined at a temperature is between about −70 and 100° C.

Embodiment M15. The method of Embodiment M14 wherein the temperature is between about −20 and 40° C.

Embodiment M16. The method of Embodiment M15 wherein the temperature is between about −10 and 20° C.

Embodiment M17. The method wherein the carboxylic acid of Formula 2 is combined with the aniline of Formula 3 to form a mixture, and then the mixture is combined with the sulfonyl chloride.

Embodiment M18. The method of Embodiment M17 wherein a base is combined with the mixture either before or after combining with the sulfonyl chloride.

Embodiment M19. The method of Embodiment M17 wherein a base is combined with the compounds of Formulae 2 and 3 to form the mixture before combining with the sulfonyl chloride.

Embodiment M20. The method wherein a base is combined with the compounds of Formulae 2 and 3 and the sulfonyl chloride.

Embodiment M21. The method of any one of Embodiments M18 to M20 wherein the amount of the base is at least about 2 equivalents relative to the sulfonyl chloride.

Embodiment M22. The method of Embodiment M21 wherein the amount of base is at least about 2.1 equivalents relative to the sulfonyl chloride.

Embodiment M23. The method of Embodiment M22 wherein the amount of the base is from about 2.1 to 2.2 equivalents relative to the sulfonyl chloride.

Embodiment M24. The method of any one of Embodiments M18 to M20 wherein the base is selected from tertiary amines (including optionally substituted pyridines).

Embodiment M25. The method of Embodiment M24 wherein the base is selected from optionally substituted pyridines and mixtures thereof.

Embodiment M26. The method of Embodiment M25 wherein the base is selected from 2-picoline, 3-picoline, 2,6-lutidine, pyridine and mixtures of the foregoing.

Embodiment M27. The method of Embodiment M26 wherein the base is 3-picoline.

Embodiment M28. The method wherein a solvent is combined with the compounds of Formulae 2 and 3 and the sulfonyl chloride.

Embodiment M29. The method of Embodiment M17 wherein a solvent is combined with the compounds of Formulae 2 and 3 to form the mixture before combining with the sulfonyl chloride.

Embodiment M30. The method of Embodiments M28 or M29 wherein the solvent is selected from nitriles (e.g., acetonitrile, propionitrile), esters (e.g., methyl acetate, ethyl acetate, butyl acetate), ketones (e.g., acetone, methyl ethyl ketone, methyl butyl ketone, haloalkanes (e.g., dichloromethane, trichloromethane), ethers (e.g., ethyl ether, methyl tert-butyl ether, tetrahydrofuran, p-dioxane), aromatic hydrocarbons (e.g., benzene, toluene, chlorobenzene, dichlorobenzene), tertiary amines (e.g., trialkylamines, dialkylanilines, optionally substituted pyridines), and mixtures of the foregoing.

Embodiment M31. The method of Embodiment M30 wherein the solvent is selected from tertiary amines (e.g., trialkylamines, dialkylanilines, optionally substituted pyridines) and mixtures of the foregoing.

Embodiment M32. The method of Embodiment M30 wherein the solvent is selected from nitriles (e.g., acetonitrile, propionitrile), esters (e.g., methyl acetate, ethyl acetate, butyl acetate), ketones (e.g., acetone, methyl ethyl ketone, methyl butyl ketone, haloalkanes (e.g., dichloromethane, trichloromethane), ethers (e.g., ethyl ether, methyl tert-butyl ether, tetrahydrofuran, p-dioxane), aromatic hydrocarbons (e.g., benzene, toluene, chlorobenzene, dichlorobenzene), and mixtures of the foregoing.

Embodiment M33. The method of Embodiment M32 wherein the solvent is acetonitrile.

Embodiment C1. A compound of Formula 3 wherein $R^1$ is $CH_3$.

Embodiment C2. A compound of Formula 3 wherein $R^2$ is Br or Cl.

Embodiment C3. A compound of Formula 3 wherein $R^2$ is I.

Embodiment C4. A compound of Formula 3 wherein $R^2$ is CN.

Embodiment C5. A compound of Formula 3 wherein $R^3$ is H or $CH_3$.

Embodiment C6. A compound of Formula 3 wherein $R^3$ is $CH_3$.

Of note are compounds of Formula 3 wherein $R^1$ is $CH_3$, $R^2$ is Cl and $R^3$ is H, $CH_2CH_3$, $CH_2CH_2CH_3$, $CH_2CH_2CH_2CH_3$, $CH_2CH(CH_3)_2$, $CH(CH_3)CH_2CH_3$ or $C(CH_3)_3$. Also of note are compounds of Formula 3 wherein $R^1$ is $CH_3$, $R^2$ is Br and $R^3$ is H, $CH_2CH_3$, $CH_2CH_2CH_3$, $CH_2CH_2CH_2CH_3$, $CH_2CH(CH_3)_2$, $CH(CH_3)CH_2CH_3$ or $C(CH_3)_3$. Also of note are compounds of Formula 3 wherein $R^1$ is $CH_3$, $R^2$ is I and $R^3$ is H, $CH_3$, $CH_2CH_3$, $CH_2CH_2CH_3$, $CH(CH_3)_2$, $CH_2CH_2CH_2CH_3$, $CH_2CH(CH_3)_2$, $CH(CH_3)CH_2CH_3$ or $C(CH_3)_3$. Also of note are compounds of Formula 3 wherein $R^1$ is $CH_3$, $R^2$ is CN and $R^3$ is $CH_2CH_3$, $CH_2CH_2CH_3$, $CH_2CH_2CH_2CH_3$, $CH_2CH(CH_3)_2$, $CH(CH_3)CH_2CH_3$ or $C(CH_3)_3$. Also of note are compounds of Formula 3 wherein $R^1$ is Cl, $R^2$ is Cl and $R^3$ is $CH_2CH_2CH_3$, $CH_2CH_2CH_2CH_3$, $CH_2CH(CH_3)_2$ or $C(CH_3)_3$. Also of note are compounds of Formula 3 wherein $R^1$ is Cl, $R^2$ is Br and $R^3$ is H, $CH_2CH_3$, $CH_2CH_2CH_3$, $CH_2CH_2CH_2CH_3$, $CH_2CH(CH_3)_2$, $CH(CH_3)CH_2CH_3$ or $C(CH_3)_3$. Also of note are compounds of Formula 3 wherein $R^1$ is Cl, $R^2$ is I and $R^3$ is H, $CH_3$, $CH_2CH_3$, $CH_2CH_2CH_3$, $CH(CH_3)_2$, $CH_2CH_2CH_2CH_3$, $CH_2CH(CH_3)_2$, $CH(CH_3)CH_2CH_3$ or $C(CH_3)_3$. Also of note are compounds of Formula 3 wherein $R^1$ is Cl, $R^2$ is CN and $R^3$ is H, $CH_3$, $CH_2CH_3$, $CH_2CH_2CH_3$, $CH(CH_3)_2$, $CH_2CH_2CH_2CH_3$, $CH_2CH(CH_3)_2$, $CH(CH_3)CH_2CH_3$ or $C(CH_3)_3$.

In the following Schemes the definitions of $R^1$, $R^2$, $R^3$, $R^4$, $R^5$ and $R^6$ in the compounds of Formulae 1 through 34 below are as defined above in the Summary of the Invention and description of embodiments unless otherwise indicated.

As shown in Scheme 1, this invention relates to a method for preparing compounds of Formula 1 by coupling carboxylic acids of Formula 2 with anthranilamides of Formula 3 using a sulfonyl chloride, typically in the presence of a base and a solvent.

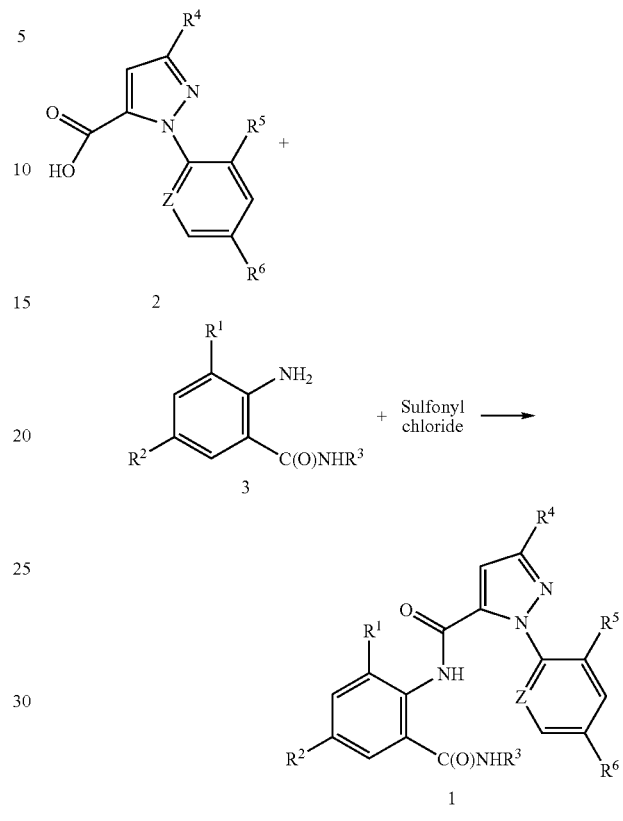

Scheme 1

Thus in the present method a pyrazolecarboxylic acid of Formula 2, an aniline of Formula 3 and a sulfonyl chloride are combined (i.e. contacted) to provide the corresponding N-phenyl-pyrazole-1-carboxamide of Formula 1.

Although a wide range of reactant ratios is possible, the nominal mole ratio of the Formula 3 compound to the Formula 2 compound is typically from about 0.9 to 1.1, and is preferably about 1.0 so that both compounds can be fully consumed. The present method can be conducted over a wide range of temperatures, but commonly it is conducted at temperatures ranging from −70° C. to +100° C. Of note are temperatures are from −20° C. to +40° C. Of particular note for reasons of convenient operation, favorable reaction rate and selectivity, and high process yield are temperatures from −10° C. to +20° C.

The sulfonyl chloride compound is used as a reactant to facilitate coupling of the carboxylic acid with the anthranilamide to form the N-phenylpyrazole-1-carboxamide. The nominal mole ratio of the sulfonyl chloride to the Formula 2 compound is typically from about 1.0 to 2.5, and preferably is from about 1.1 to 1.4 when the cyclization side reaction described below occurs to no more than a small extent (i.e. 0-10%). Sulfonyl chlorides are generally of the formula $R^8S(O)_2Cl$ (Formula 4) wherein $R^8$ is a carbon-based radical. Typically for the present method $R^8$ is $C_1$-$C_4$ alkyl, $C_1$-$C_2$ haloalkyl, or phenyl optionally substituted with 1-3 substituents selected from the group consisting of halogen, $C_1$-$C_3$ alkyl and nitro. Sulfonyl chloride compounds preferred for the present method because of their commercial availability include methanesulfonyl chloride ($R^8$ is $CH_3$), propanesulfonyl chloride ($R^8$ is $(CH_2)_2CH_3$), benzenesulfonyl chloride ($R^8$ is Ph), and p-toluenesulfonyl chloride ($R^8$ is 4-$CH_3$-Ph).

Methanesulfonyl chloride is more preferred for reasons of lower cost, ease of addition and/or less waste.

In the present method, the sulfonyl chloride is combined with the pyrazolecarboxylic acid of Formula 2 and the aniline of Formula 3. The reactants can be combined in a variety of orders, such as combining the sulfonyl chloride with the carboxylic acid of Formula 2 to form a mixture and then combining the mixture with the aniline of Formula 3. However, for preparing the particular N-phenylpyrazole-1-carboxamides of Formula 1, the most preferable order of combination has been found to comprise combining the carboxylic acid of Formula 2 with the aniline of Formula 3 to form a mixture and then combining the sulfonyl chloride with the mixture (e.g., adding the sulfonyl chloride to the mixture of the compounds of Formulae 2 and 3), because this order of the addition allows convenient control of the coupling process. The rate of reaction is readily controlled by simply controlling the rate of addition of the sulfonyl chloride compound. Therefore an embodiment of note of the present method comprises the sequential steps of (1) combining a carboxylic acid of Formula 2 and an aniline of Formula 3 to form a mixture, and (2) then combining the mixture with a sulfonyl chloride. Although addition of the sulfonyl chloride to the mixture containing the aniline of Formula 2 potentially could result in undesirable side reactions, it has been discovered that the particular stereoelectronic profiles of the compounds of Formulae 2 and 3 facilitate obtaining remarkably high yields of compounds of Formula 1 using the present method.

The compound of Formula 1 is formed when the starting compounds of Formulae 2 and 3 and the sulfonyl chloride are contacted with each other in a combined liquid phase, in which each is at least partially soluble. Particularly as the starting materials of Formulae 2 and 3 are typically solids at ordinary ambient temperatures, the method is most satisfactorily conducted using a solvent in which the starting compounds have significant solubility. Thus typically the method is conducted in a liquid phase comprising a solvent. In some cases the carboxylic acid of Formula 2 may have only slight solubility but its salt with added base may have more solubility in the solvent. Suitable solvents for this method include nitriles such as acetonitrile and propionitrile; esters such as methyl acetate, ethyl acetate, and butyl acetate; ketones such as acetone, methyl ethyl ketone (MEK), and methyl butyl ketone; haloalkanes such as dichloromethane and trichloromethane; ethers such as ethyl ether, methyl tert-butyl ether, tetrahydrofuran (THF), and p-dioxane; aromatic hydrocarbons such as benzene, toluene, chlorobenzene, and dichlorobenzene; tertiary amines such as trialkylamines, dialkylanilines, and optionally substituted pyridines; and mixtures of the foregoing. Solvents of note include acetonitrile, propionitrile, ethyl acetate, acetone, MEK, dichloromethane, methyl tert-butyl ether, THF, p-dioxane, toluene, and chlorobenzene. Of particular note as solvent is acetonitrile, as it often provides products in superior yield and/or purity.

As the reaction of the present method generates hydrogen chloride as a byproduct, which would otherwise bind to basic centers on the compounds of Formulae 1, 2 and 3, the method is most satisfactorily conducted in the presence of at least one added base. The base can also facilitate constructive interaction of the carboxylic acid with the sulfonyl chloride compound and the anthranilamide. Reaction of an added base with the carboxylic acid of Formula 2 forms a salt, which may have greater solubility than the carboxylic acid in the reaction medium. Although the base may be added at the same time, in alternation, or even after the addition of the sulfonyl chloride, the base is typically added before the addition of the sulfonyl chloride. Some solvents such as tertiary amines also serve as bases, and when these are used as solvents they will be in large stoichiometric excess as bases. When the base is not used as solvent the nominal mole ratio of the base charged to the sulfonyl chloride charged is typically from about 2.0 to 2.2, and is preferably from about 2.1 to 2.2. Preferred bases are tertiary amines, including substituted pyridines. More preferred bases include 2-picoline, 3-picoline, 2,6-lutidine, and pyridine. Of particular note as base is 3-picoline, as its salts with carboxylic acids of Formula 2 are often highly soluble in solvents such as acetonitrile.

The features of the present method provide efficient production of the N-phenylpyrazole-1-carboxamide of Formula 1 while limiting the amounts of the carboxylic acid, the sulfonyl chloride and the anthranilamide that are consumed during the formation of the N-phenylpyrazole-1-carboxamide and reducing waste. The present method allows convenient control of the coupling process and provides a method involving fewer and simpler operations as compared to previously known processes for the production of N-phenylpyrazole-1-carboxamides such as Formula 1.

A preferred embodiment of the present method combines the pyrazolecarboxylic acid of Formula 2, the anthranilic acid of Formula 3, and a suitable base in a suitable solvent, followed by the addition of the sulfonyl chloride compound (either alone or mixed with a suitable solvent).

The product N-phenylpyrazole-1-carboxamides of Formula 1 can be isolated from the reaction mixtures by methods known to those skilled in the art, including crystallization, filtration, and extraction. As shown in Scheme 2, in some cases, partial cyclization of amides 1 to iminobenzoxazines of Formula cyclo-1 occurs under the conditions of the coupling reaction.

Scheme 2

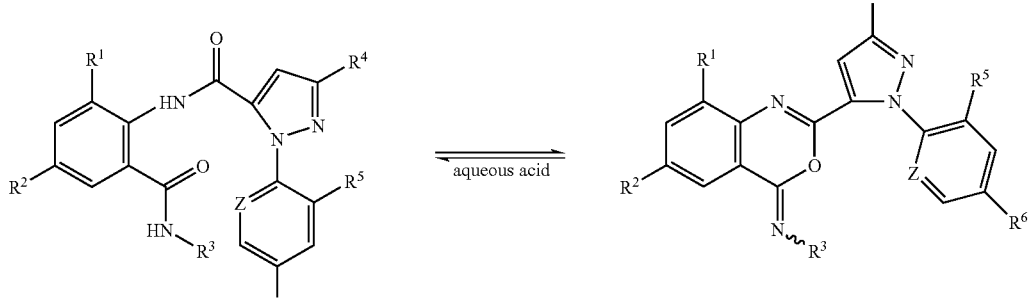

In these cases, it is often advantageous to convert the Formula cyclo-1 compound back to the amide of Formula 1 prior to isolation of the reaction product. This conversion can be accomplished by treatment of the reaction mixture with aqueous acid. Alternatively, the mixture of the iminobenzoxazine of Formula cyclo-1 and amide of Formula 1 can be isolated and this mixture can then be converted to the amide of Formula 1, for example by treatment with dilute aqueous acid, optionally in the presence of a suitable organic solvent.

Under the preferred conditions of this process, the cyclization side reaction converting the desired product of Formula 1 to the Formula cyclo-1 compound usually occurs to only a minor extent, if at all, in which cases the preferred ratios of sulfonyl chloride and base are sufficient to complete the coupling reaction. However, for some pyrazolecarboxylic acids of Formula 2, anthranilic acids of Formula 3 (such as when $R^2$ is CN) and conditions of the reaction (e.g., using sterically hindered substituted pyridines such as 2,6-lutidine as bases), the conversion of the desired product of Formula 1 to the Formula cyclo-1 compound can occur to a more significant extent or can be the predominant reaction. In these cases, the use of larger ratios of sulfonyl chloride and base can facilitate completion of the coupling reaction. The cyclization side reaction stoichiometrically consumes an equivalent of sulfonyl chloride in addition to the equivalent of sulfonyl chloride consumed in the coupling reaction. Therefore if 100% cyclization were to occur, a 2:1 mole ratio of sulfonyl chloride to Formula 2 compound would stoichiometrically be needed to achieve complete consumption of starting materials, and typically up to about a 2.5:1 mole ratio of sulfonyl chloride to Formula 2 compound would be used, in contrast to an about 1.4:1 mole ratio of sulfonyl chloride to Formula 2 compound when the cyclization occurs only to the extent of 5-10% (as is typical with most bases when $R^2$ is CN) and an about 1.2:1 mole ratio of sulfonyl chloride to Formula 2 compound when the cyclization side reaction is negligible (as is typical with most bases when $R^2$ is Br, Cl or I). The additional quantities of sulfonyl chloride and base can be added while the reaction is in progress if the cyclization reaction is observed to be occurring.

The above illustrates a valuable feature of this process, which is that additional quantities of any of the components of the process can be added at any time as required to complete the conversion. Another illustration of the value of this feature concerns the situation where either the component of Formula 2 or the component of Formula 3 is inadvertently undercharged to a reaction mixture. This undercharge can be detected by analysis of the reaction mixture using any of a variety of methods that are generally known and available, including HPLC and NMR. Once detected, the undercharge can be corrected by adding more of the appropriate component to the reaction mixture. This can be particularly valuable for larger scale work, since it allows recovery from a charging error and prevents the resultant waste of an expensive intermediate, which might otherwise occur.

Pyrazolecarboxylic acids of Formula 2 can be prepared using methods of heterocyclic synthesis known in the literature, including references found in the following compendia: *Rodd's Chemistry of Chemistry of Carbon Compounds*, Vol. IVa to IVl, S. Coffey editor, Elsevier Scientific Publishing, New York, 1973; *Comprehensive Heterocyclic Chemistry*, Vol. 1-7, A. R. Katritzky and C. W. Rees editors, Pergamon Press, New York, 1984; *Comprehensive Heterocyclic Chemistry II*, Vol. 1-9, A. R. Katritzky, C. W. Rees, and E. F. Scriven editors, Pergamon Press, New York, 1996; and the series, *The Chemistry of Heterocyclic Compounds*, E. C. Taylor, editor, Wiley, New York. A variety of heterocyclic acids (including pyrazolecarboxylic acids) and general methods for their synthesis are found in PCT Patent Publication WO 98/57397.

One particularly useful procedure for preparing pyrazolecarboxylic acids of Formula 2a is shown in Scheme 3.

Scheme 3

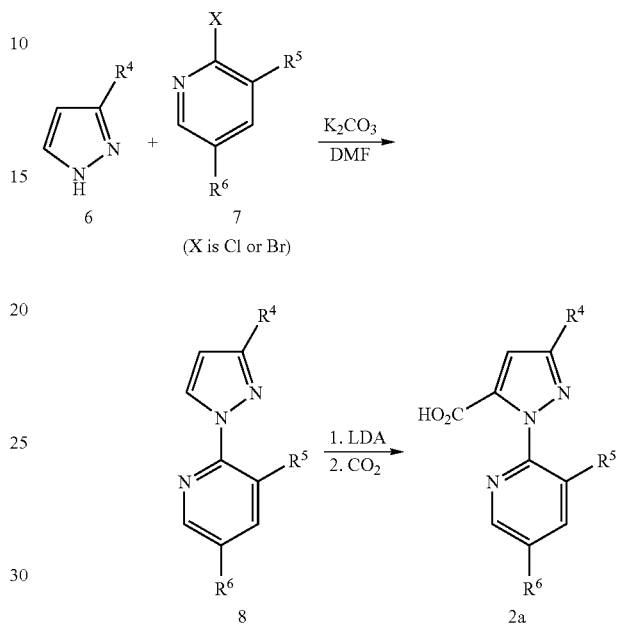

Reaction of a pyrazole of Formula 6 with a 2-halopyridine of Formula 7 affords good yields of the 1-pyridinylpyrazole of Formula 8 with good specificity for the desired regiochemistry. Metallation of the compound of Formula 8 with lithium diisopropylamide (LDA) followed by quenching of the lithium salt with carbon dioxide affords the 1-(2-pyridinyl) pyrazolecarboxylic acid of Formula 2a. For a leading reference to this method see PCT Patent Publication WO 03/015519.

As shown in Scheme 4, pyrazolecarboxylic acids of Formula 2b can be prepared via 3+2 cycloaddition of an appropriately substituted iminohalide of Formula 9 with either substituted propiolates of Formula 10 or acrylates of Formula 11.

Scheme 4

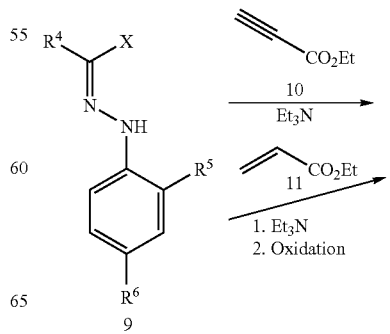

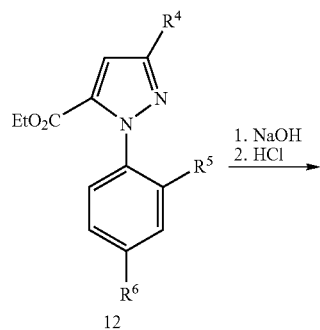

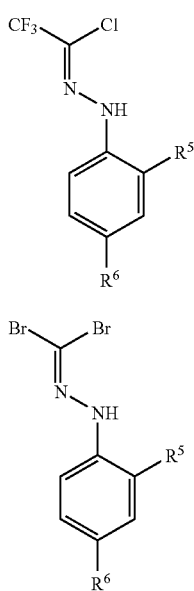

Cycloaddition with acrylates requires additional oxidation of the intermediate pyrazoline to S the pyrazole. Hydrolysis of the ester of Formula 12 affords the pyrazolecarboxylic acids of Formula 2b. Preferred iminohalides for this reaction include the trifluoromethyl iminochloride of Formula 9a and the iminodibromide of Formula 9b. Compounds such as Formula 9a are known (*J. Heterocycl. Chem.* 1985, 22(2), 565-8). Other compounds of Formula 9 such as Formula 9b are available by known methods (*Tetrahedron Letters* 1999, 40, 2605).

Another method for preparation of pyrazolecarboxylic acids of Formula 2b is shown in Scheme 5.

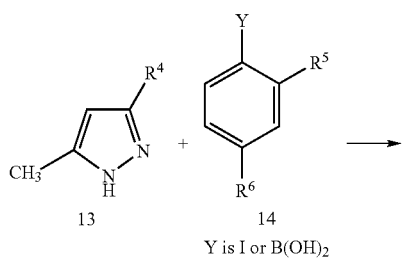

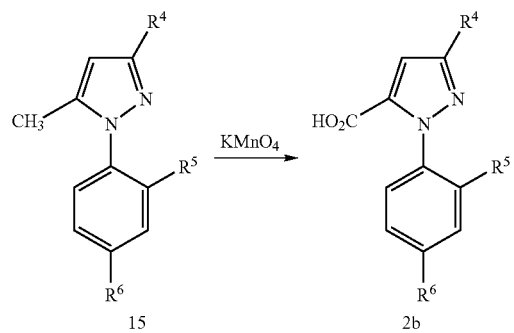

Pyrazoles of Formula 13 can be condensed with aryl iodides using methods such as those reported by A. Klapars, J. C. Antilla, X. Huang and S. L. Buchwald, *J. Am. Chem. Soc.* 2001, 123, 7727-7729, or with aryl boronic acids using methods such as those reported by P. Y. S. Lam, C. G. Clark, S. Saubern, J. Adams, M. P. Winters, D. M. T. Chan and A. Combs, *Tetrahedron Lett.* 1998, 39, 2941-2944. The resulting adducts of Formula 15 can be oxidized with oxidizing agents such as potassium permanganate to afford the pyrazolecarboxylic acids of Formula 2b.

The starting pyrazoles of Formulae 6 and 13 are known compounds or can be prepared according to known methods. For example, the pyrazole of Formula 6a (the compound of Formula 6 wherein $R^4$ is $CF_3$) can be prepared by literature procedures (*J. Fluorine Chem.* 1991, 53(1), 61-70). The pyrazoles of Formula 6b (compounds of Formula 6 wherein $R^4$ is Cl or Br) can be prepared by the procedure described in *Chem. Ber.* 1966, 99(10), 3350-7.

A useful alternative method for the preparation of a compound of Formula 6b is depicted in Scheme 6.

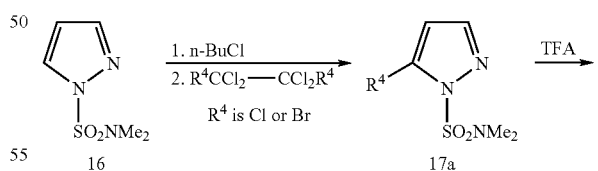

Metallation of the sulfamoylpyrazole of Formula 16 with n-butyllithium followed by direct halogenation of the anion with either hexachloroethane (for $R^4$ being Cl) or 1,2-dibromotetrachloroethane (for $R^4$ being Br) affords the halogenated derivatives of Formula 17a. Removal of the sulfamoyl group with trifluoroacetic acid (TFA) at room temperature proceeds cleanly and in good yield to afford the pyrazoles of Formula 6c. One of ordinary skill in the art will recognize that Formula 6c is a tautomer of Formula 6b.

Pyrazolecarboxylic acids 2 can also be prepared by oxidation of the pyrazoline of Formula 18 to give the pyrazole of Formula 19 followed by hydrolysis to the carboxylic acid as shown in Scheme 7.

Scheme 7

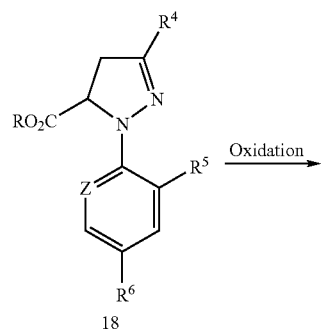

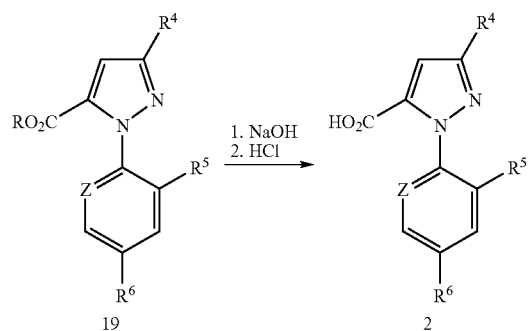

The oxidizing agent can be hydrogen peroxide, organic peroxides, potassium persulfate, sodium persulfate, ammonium persulfate, potassium monopersulfate (e.g., Oxone®) or potassium permanganate. This oxidation can be carried out in the presence of a solvent, preferably an ether, such as tetrahydrofuran, p-dioxane and the like, an organic ester, such as ethyl acetate, dimethyl carbonate and the like, or a polar aprotic organic such as N,N-dimethylformamide, acetonitrile and the like.

Halopyrazolines 18 wherein $R^4$ is Cl or Br can be prepared from pyrazolones of Formula 20 by treatment with an appropriate halogenating agent as shown in Scheme 8.

Scheme 8

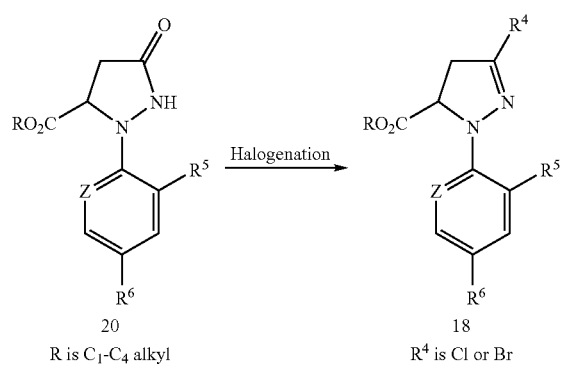

Halogenating reagents that can be used include phosphorus oxyhalides, phosphorus trihalides, phosphorus pentahalides, thionyl chloride, dihalotrialkylphosphoranes, dihalotriphenylphosphoranes, oxalyl chloride and phosgene. Preferred are phosphorus oxyhalides and phosphorus pentahalides. Typical solvents for this halogenation include halogenated alkanes, such as dichloromethane, chloroform, chlorobutane and the like, aromatic solvents, such as benzene, xylene, chlorobenzene and the like, ethers, such as tetrahydrofuran, p-dioxane, diethyl ether, and the like, and polar aprotic solvents such as acetonitrile, N,N-dimethylformamide, and the like. Optionally, an organic base, such as triethylamine, pyridine, N,N-dimethylaniline or the like, can be added. Addition of a catalyst, such as N,N-dimethylformamide, is also an option.

Alternatively, compounds of Formula 18 wherein $R^4$ is halogen can be prepared by treating the corresponding compounds of Formula 18 wherein $R^4$ is a different halogen (e.g., Cl for making Formula 18 wherein $R^4$ is Br) or a sulfonate group such as methanesulfonate, benzenesulfonate or p-toluenesulfonate, with hydrogen bromide or hydrogen chloride, respectively. By this method the $R^4$ halogen or sulfonate substituent on the Formula 18 starting compound is replaced with Br or Cl from hydrogen bromide or hydrogen chloride, respectively. Starting compounds of Formula 18 wherein $R^4$ is Cl or Br can be prepared from corresponding compounds of Formula 20 as already described. Starting compounds of Formula 18 wherein $R^4$ is a sulfonate group can likewise be prepared from corresponding compounds of Formula 20 by standard methods such as treatment with a sulfonyl chloride (e.g., methanesulfonyl chloride, benzenesulfonyl chloride, or p-toluenesulfonyl chloride) and a base such as a tertiary amine (e.g., triethylamine) in a suitable solvent such as dichloromethane.

Pyrazolecarboxylic acids of Formula 2c wherein $R^4$ is $OCHF_2$ or $OCH_2CF_3$ can be prepared by the method outlined in Scheme 9.

Scheme 9

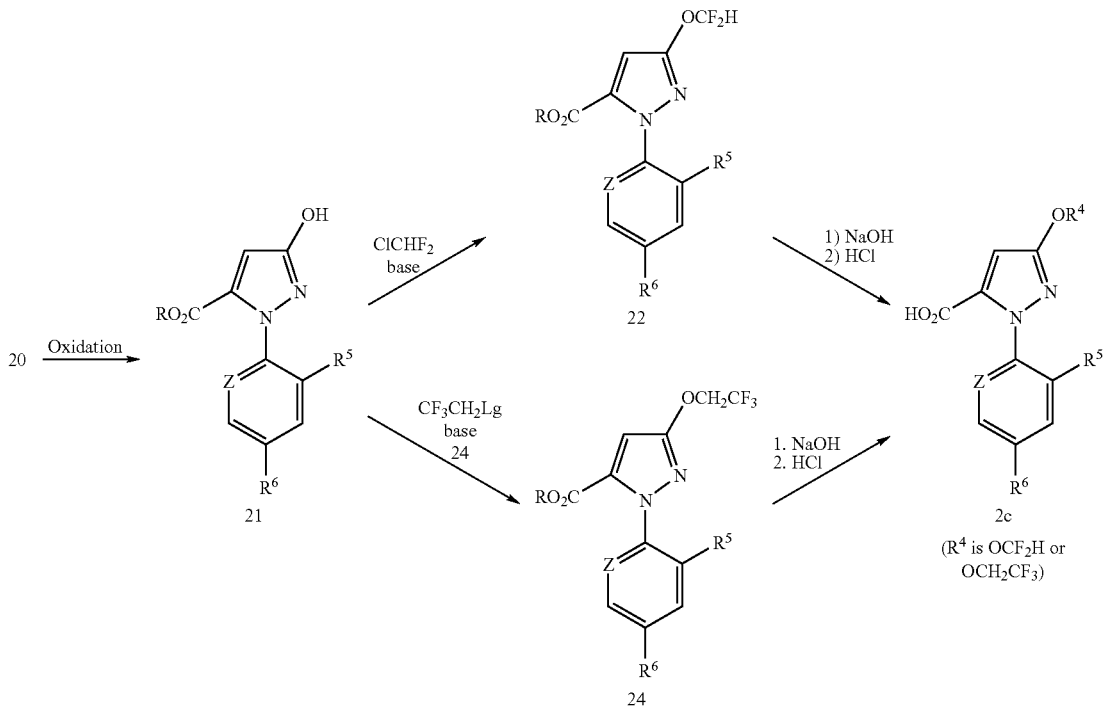

R is C$_1$-C$_4$ alkyl,
Lg is a leaving group

In this method, instead of being halogenated as shown in Scheme 8, the compound of Formula 20 is oxidized to the compound of Formula 21. The reaction conditions for this oxidation are as already described for the conversion of the compound of Formula 18 to the compound of Formula 19 in Scheme 7. The compound of Formula 21 can then be alkylated to form the compound of Formula 22 by contact with difluorocarbene, prepared in situ from CHClF$_2$ in the presence of a base. The compound of Formula 21 can also be alkylated to form the compound of Formula 24 by contact with an alkylating agent CF$_3$CH$_2$Lg in the presence of a base. The alkylation reaction is generally conducted in a solvent, which can comprise ethers, such as tetrahydrofuran or dioxane, and polar aprotic solvents, such as acetonitrile, N,N-dimethylformamide, and the like. The base can be selected from inorganic bases such as potassium carbonate, sodium hydroxide or sodium hydride. Preferably the reaction is conducted using potassium carbonate with N,N-dimethylformamide or acetonitrile as the solvent. In the alkylating agent CF$_3$CH$_2$Lg, Lg is a nucleofuge (i.e. leaving group) such as halogen (e.g., Br, I), OS(O)$_2$CH$_3$ (methanesulfonate), OS(O)$_2$CF$_3$, OS(O)$_2$Ph-p-CH$_3$ (p-toluenesulfonate), and the like. The product of Formula 22 can be isolated by conventional techniques such as extraction. The esters can then be converted to the carboxylic acids of Formula 2c by the methods already described for the conversion of Formula 12 to Formula 2b in Scheme 4.

Compounds of Formula 20 can be prepared from compounds of Formula 25 as outlined in Scheme 10.

Scheme 10

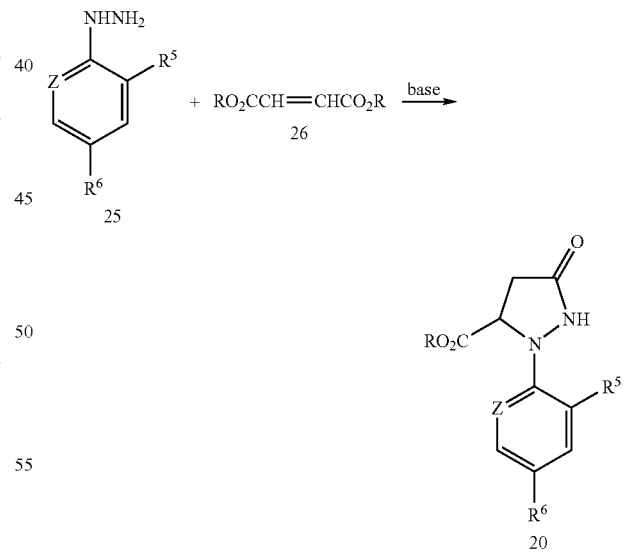

In this method, a hydrazine compound of Formula 25 is contacted with a compound of Formula 26 (a fumarate ester or maleate ester or a mixture thereof may be used) in the presence of a base and a solvent. The base is typically a metal alkoxide salt, such as sodium methoxide, potassium methoxide, sodium ethoxide, potassium ethoxide, potassium tert-butoxide, lithium tert-butoxide, and the like. Polar protic and polar aprotic organic solvents can be used, such as alcohols, acetonitrile, tetrahydrofuran, N,N-dimethyl-formamide, dimethyl sulfoxide and the like. Preferred solvents are alcohols such as methanol and ethanol. It is especially preferred that the alcohol correspond to (i.e. be the same as that making up) the fumarate or maleate ester and the alkoxide base. Depending on the reaction conditions and the means of isolation, the —$CO_2R$ function on the compound of Formula 20 may be hydrolyzed to —$CO_2H$; for example, the presence of water in the reaction mixture can promote such hydrolysis. If the carboxylic acid (—$CO_2H$) is formed, it can be converted back to —$CO_2R$ wherein R is $C_1$-$C_4$ alkyl using esterification methods well known in the art. The desired product, a compound of Formula 20, can be isolated by methods known to those skilled in the art, such as crystallization, extraction or distillation.

Another aspect of this invention is directed to anthranilamides of Formula 3, which are important intermediates in the process of this invention. Samples of anthranilamides of Formula 3 are also useful as analytical standards for determining the presence of the anthranilamides.

Anthranilamides of Formula 3 can be prepared from the reaction of isatoic anhydrides for Formula 27 with ammonia or alkylamines, as shown in Scheme 11, by using procedures such as that described by L. H. Sternbach et al., *J. Org. Chem.* 1971, 36, 777-781.

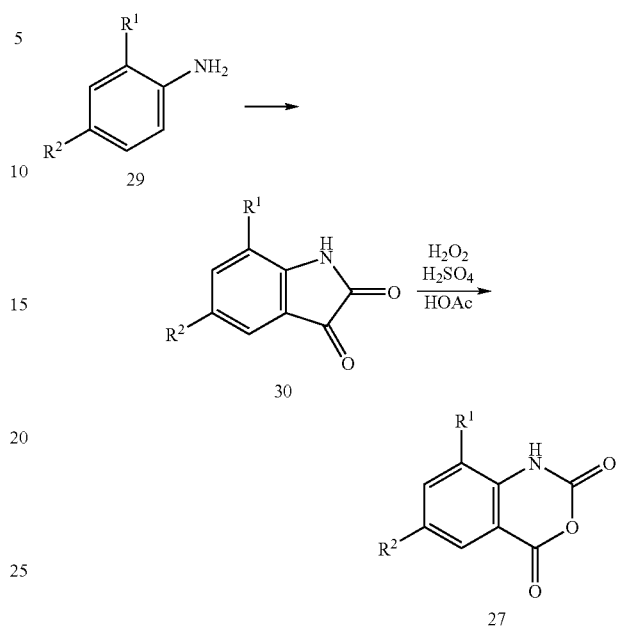

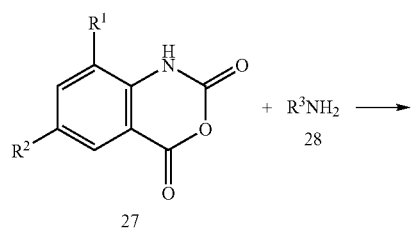

Isatoic anhydrides of Formula 27 can be made by a variety of known methods that are well documented in the chemical literature. For example, isatoic anhydrides are available from the corresponding anthranilic acids via cyclization involving reaction of the anthranilic acid with phosgene or a phosgene equivalent. For leading references to the methods, see Coppola, *Synthesis* 1980, 505 and Fabis et al., *Tetrahedron*, 1998, 10789.

The synthesis of the isatoic anhydrides of Formula 27 can also be achieved from isatins of Formula 30 as outlined in Scheme 12.

Isatins of Formula 30 are available from aniline derivatives of Formula 29 following literature procedures such as F. D. Popp, *Adv. Heterocycl. Chem.* 1975, 18, 1-58 and J. F. M. Da Silva et al., *Journal of the Brazilian Chemical Society* 2001, 12(3), 273-324. Oxidation of isatin 30 with hydrogen peroxide generally affords good yields of the corresponding isatoic anhydride 28 (G. Reissenweber and D. Mangold, *Angew. Chem. Int. Ed. Engl.* 1980, 19, 222-223).

As shown in Scheme 13, isatins of Formula 30 wherein $R^2$ is Cl, Br or I are also available from the 5-unsubstituted isatins of Formula 31 by halogenation. Cyanide displacement can then provide isatins of Formula 30a (Formula 30 where $R^2$ is CN).

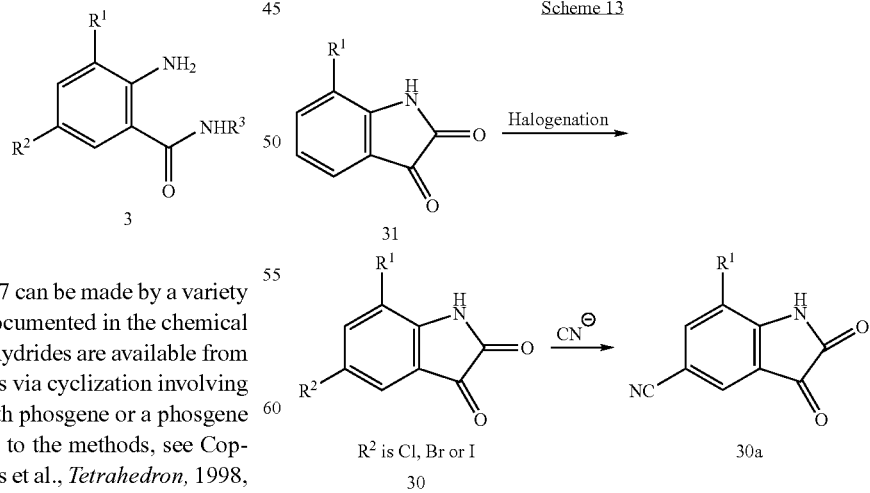

The halogenation reaction can be carried out using many reagents and procedures known in the literature. Suitable reagents include the elemental halogens (chlorine, bromine, or iodine), "positive-halogen" reagents such as trichloroisocyanuric acid, N-chlorosuccinimide (NCS), N-bromosuccinimide (NBS) or N-iodosuccinimide (NIS), and halogenating reagents such as the mixtures comprising hydrogen peroxide and a hydrogen halide. The halogen at the 5-position of isatins of Formula 30 wherein $R^2$ is Cl, Br or I can be displaced by cyanide using methods known in the literature. These methods include the use of a cyanide salt, usually employing a metal compound, and often in the presence of a ligand such as a substituted phosphine or a substituted bisphosphinoalkane. Suitable methods include those employing compounds of palladium such as those described by P. E. Maligres et al., *Tetrahedron Letters* 1999, 40, 8193-8195, and by M. Beller et al., *Chem. Eur. J.* 2003, 9(8), 1828-1836; those employing compounds of copper such as those described by S. L. Buchwald in *J. Am. Chem. Soc.* 2003, 125, 2890-2891; and those employing compounds of nickel such as those described in European Patent 384392, and by K. Sasaki in *Bull. Chem. Soc. Japan* 2004, 77, 1013-1019, and by R. K. Arvela and N. E. Leadbeater in *J. Org. Chem.* 2003, 68, 9122-9125. One versed in the art will appreciate that when $R^1$ is Cl, $R^2$ of Formula 27 is preferably Br or I to obtain selectivity in the cyanation (i.e. displacement of halogen by cyanide).

As shown in Scheme 14, anthranilamides of Formula 3 are typically available from the corresponding 2-nitrobenzoic acids (or esters) of Formula 32 via catalytic hydrogenation of the nitro group followed by reaction of the anthranilic ester of Formula 33 with ammonia or an alkylamine.

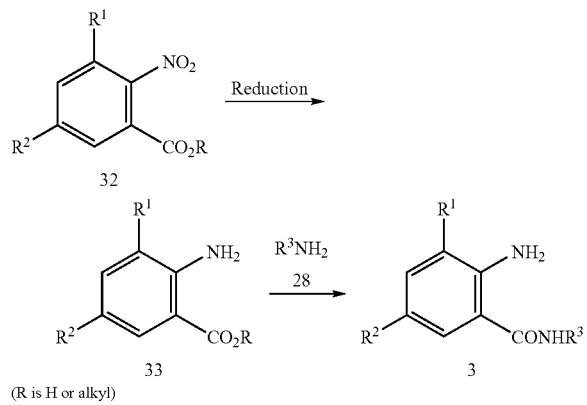

Typical reduction procedures involve reduction with hydrogen in the presence of a metal catalyst such as palladium on carbon or platinum oxide in hydroxylic solvents such as ethanol and isopropanol. The reduction can also be conducted in the presence of zinc in acetic acid. These methods for reducing nitro groups are well documented in the chemical literature. Many methods for interconversion of carboxylic acids, esters, and amides are also well documented in the chemical literature.

As shown in Scheme 15, anthranilamides of Formula 3 are also available from the 5-unsubstituted anthranilamides of Formula 34 by halogenation to provide anthranilamides of Formula 3 wherein $R^2$ is Br, Cl or I, optionally followed by cyanide displacement to provide anthranilamides of Formula 3a (Formula 3 where $R^2$ is CN).

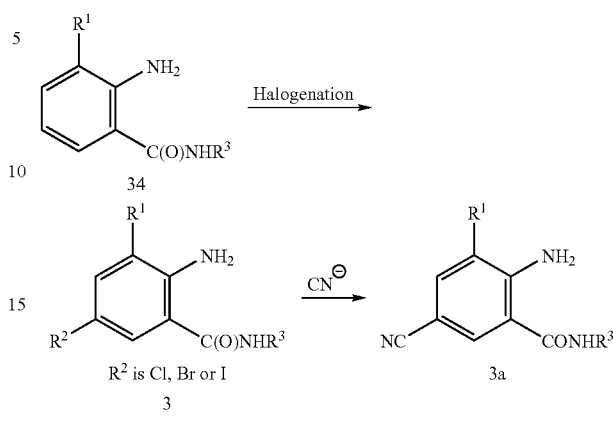

Suitable methods and procedures are known in the literature and are similar to those described for the halogenations and cyanide displacements shown in Scheme 13. One skilled in the art will recognize that the halogenation and cyanation can also be carried out at other stages in the preparation of anthranilamides of Formula 3.

It is recognized that some reagents and reaction conditions described above for preparing compounds of Formulae 2 and 3 may not be compatible with certain functionalities present in the intermediates. In these instances, the incorporation of protection/deprotection sequences or functional group interconversions into the synthesis will aid in obtaining the desired products. The use and choice of the protecting groups will be apparent to one skilled in chemical synthesis (see, for example, Greene, T. W.; Wuts, P. G. M. *Protective Groups in Organic Synthesis,* 2nd ed.; Wiley: New York, 1991). One skilled in the art will recognize that, in some cases, after the introduction of a given reagent as it is depicted in any individual scheme, it may be necessary to perform additional routine synthetic steps not described in detail to complete the synthesis of compounds of Formulae 2 and 3. One skilled in the art will also recognize that it may be necessary to perform a combination of the steps illustrated in the above schemes in an order other than that implied by the particular sequence presented to prepare the compounds of Formulae 2 and 3. One skilled in the art will also recognize that compounds of Formulae 2 and 3 and the intermediates described herein can be subjected to various electrophilic, nucleophilic, radical, organometallic, oxidation, and reduction reactions to add substituents or modify existing substituents.

Without further elaboration, it is believed that one skilled in the art using the preceding description can utilize the present invention to its fullest extent. The following Examples are, therefore, to be construed as merely illustrative and not limiting of the disclosure in any way whatsoever. Steps in the following Examples illustrate a procedure for each step in an overall synthetic transformation, and the starting material for each step may not have necessarily been prepared by a particular preparative run whose procedure is described in other Examples or Steps. Percentages are by weight except for chromatographic solvent mixtures or where otherwise indicated. Parts and percentages for chromatographic solvent mixtures are by volume unless otherwise indicated. $^1$H NMR spectra are reported in ppm downfield from tetramethylsilane; s is singlet, d is doublet, t is triplet, q is quartet, m is multiplet, dd is doublet of doublets, dt is doublet of triplets, br s is broad singlet. Quantitative HPLC of the product was performed using an Ace C18 or C4 Ultra Inert® chromatography column (reversed phase column manufactured by MacMod Analytical Inc., Chadds Ford, Pa. 19317) (3 μm particle size, 4.6 mm×15 cm, eluent 5-80% acetonitrile/pH 3 phosphate buffer).

EXAMPLE 1

Preparation of
2-amino-5-chloro-N,3-dimethylbenzamide

To a suspension of 6-chloro-8-methyl-2H-3,1-benzoxazine-2,4(1H)-dione (211.6 g, 1000 mmol) in acetonitrile (700 mL) was added acetic acid (7.3 g, 122 mmol). Then 40% aqueous methylamine (104 mL) was added dropwise over 30 minutes at 25-30° C. Stirring was continued for 2 h, and then water (700 mL) was added slowly. The resulting suspension was cooled to 5° C., and stirred for 30 minutes at this temperature. The suspension was then filtered, and the solids were washed with water (3×200 mL) and dried under nitrogen to afford the title compound as off-white needles, 172.8 g (87.0% yield), m.p. 141-143° C.
$^1$H NMR (DMSO-$d_6$) δ 2.08 (s, 3H), 2.72 (d, J=4.5 Hz, 3H), 6.34 (br s, 2H), 7.12 (d, J=2.4 Hz, 1H), 7.39 (d, J=2.4 Hz, 1H), 8.31 (br d, 1H).

EXAMPLE 2

Preparation of methyl
2-amino-5-chloro-3-methylbenzoate

Step A: Preparation of
2-amino-5-chloro-3-methylbenzoic acid

To a solution of 2-amino-3-methylbenzoic acid (Aldrich, 15.0 g, 99.2 mmol) in N,N-dimethylformamide (50 mL) was added N-chlorosuccinimide (13.3 g, 99.2 mmol) and the reaction mixture was heated to 100° C. for 30 minutes. The heat was removed and the reaction mixture was cooled to room temperature and allowed to stand overnight. The reaction mixture was then slowly poured into ice water (250 mL) to precipitate a white solid. The solid was filtered and washed four times with water and then taken up in ethyl acetate (900 mL). The ethyl acetate solution was dried (MgSO$_4$) and evaporated under reduced pressure, and the residual solid was washed with ether to afford the desired intermediate as a white solid, 13.9 g (75.4% yield).
$^1$H NMR (DMSO-$d_6$) δ 2.11 (s, 3H), 7.22 (s, 1H), 7.55 (s, 1H).

Step B: Preparation of methyl
2-amino-5-chloro-3-methylbenzoate

To a suspension of 2-amino-5-chloro-3-methylbenzoic acid (i.e. the product of Step A) (92.8 g, 500 mmol) in acetonitrile (500 mL) at 0-5° C. was added 1,4-diaza-bicyclo [5.4.0]undec-7-ene (DBU, 90 mL, 92 g, 600 mmol), and then dimethyl sulfate (57 mL, 76 g, 600 mmol) was added dropwise at 0-5° C. After stirring 3 h at this temperature, additional DBU (15 mL) and dimethyl sulfate (10 mL) were added. After stirring another 3 h at this temperature, more additional DBU (15 mL) and dimethyl sulfate (10 mL) were added. After stirring another 2 h at this temperature, concentrated hydrochloric acid (60 mL, 720 mmol) was added dropwise at 0-10° C. The resulting suspension was stirred for 30 minutes at 0-5° C., then filtered, and the solids were washed with ice-cold 2:1 water-acetonitrile (3×100 mL), and dried under nitrogen. The crude product was suspended in methanol (250 mL), water (1000 mL) was added, and the mixture was stirred at room temperature for 1 h. Then the solids were filtered, washed with 4:1 water-methanol (100 mL), then with water (3×100 mL), and dried under nitrogen to afford the title compound as a low-melting white solid, 87.6 g (87.8% yield). HPLC of the solid product showed 99.7 area % of the title ester.
$^1$H NMR (CDCl$_3$) δ 2.15 (s, 3H), 3.87 (s, 3H), 5.82 (br s, 2H), 7.15 (d, J=2.7 Hz, 1H), 7.74 (d, J=2.7 Hz, 1H).

EXAMPLE 3

Preparation of
2-amino-5-chloro-N,3-dimethylbenzamide

To a suspension of methyl 2-amino-5-chloro-3-methylbenzoate (i.e. the product of Example 2) (4.03 g, 20.2 mmol) in acetonitrile (12.4 g) was added a solution of methylamine (3.1 g, 0.10 mol) in ethylene glycol (12.4 g). The mixture was heated at 60° C. for 23 h, and then cooled to room temperature. Water (25 mL) was added dropwise, and the resulting slurry was cooled to 5° C. and stirred for 10 minutes at this temperature. The mixture was filtered, and the solids were washed with water (3×10 mL), and dried under nitrogen to afford the title compound as white needles, 3.43 g (85.5% yield).

EXAMPLE 4

Preparation of
2-amino-5-chloro-N,3-dimethylbenzamide

Step A: Preparation of methyl
2-amino-3-methylbenzoate

Methyl 3-methyl-2-nitrobenzoate (98.5 g, 505 mmol), 5% Pd/C (Degussa CE 105 XRC/W, 1.0 g), and acetonitrile (300 mL) were combined in a 600-mL pressure vessel. The mixture was heated to 70° C. and hydrogenated at 65 psi (450 kPa) for 8 h. More 5% Pd/C (1.0 g) was added and hydrogenation was continued at 100 psi (690 kPa) for 8.5 h. Then the reaction mixture was cooled, purged with nitrogen, and filtered through Celite® diatomaceous filter aid, rinsing with acetonitrile (3×25 mL). The combined filtrates were partly evaporated to a weight of ~160 g, and then diluted with acetonitrile to a total weight of 200g. Quantitative HPLC of this solution showed 40.3 wt % of the title compound (80.6 g, 97.5% yield).

Step B: Preparation of
methyl 2-amino-5-chloro-3-methylbenzoate

The solution prepared in Step A (195 g, 475 mmol) was diluted with acetonitrile (50 mL), and heated to 50° C. Then a solution of sulfuryl chloride (70.6 g, 523 mmol) in acetonitrile (100 mL) was added over 3.25 h at 50-55° C. Immediately after completion of the addition, the mixture was cooled to 5° C., water (150 g) was added, and the pH of the solution was adjusted to 6.0 by slow addition of 50% aqueous sodium hydroxide (103 g). After stirring for 10 minutes at this temperature, the organic layer was separated, and the aqueous layer was extracted with acetonitrile (50 mL). The organic layers were combined, dried (MgSO$_4$), and partially evaporated to a weight of 193.7 g. Quantitative HPLC of this solution showed 41.5 wt % of the title compound (80.4 g, 84.8% yield).

Step C: Preparation of
2-amino-5-chloro-N,3-dimethylbenzamide

The solution prepared in Step B (96.2 g, 200 mmol) was diluted with acetonitrile (60.0 g) and ethylene glycol (180 g) and dried azeotropically by distilling at atmospheric pressure under a Claisen distillation head to take off ~72 mL of volatiles. Then the distillation head was replaced with a dry-ice-cooled condenser, the remaining solution was cooled to 0-5° C., and methylamine gas (31.1 g, 1000 mmol) was added below the surface of the reaction mixture. The mixture was heated at 70° C. for 17.5 h, and then water (400 mL) was added slowly to precipitate the product. The mixture was cooled slowly to 5° C., stirred for 15 minutes at this temperature, filtered, and the solids were washed with water and dried under nitrogen to afford the subject compound (36.36 g, 91.5% yield). HPLC showed 99.3 area % purity.

EXAMPLE 5

Preparation of
2-amino-5-chloro-N,3-dimethylbenzamide

Step A: Preparation of
2-amino-N,3-dimethylbenzamide

A mixture of 8-methyl-2H-3,1-benzoxazine-2,4(1H)-dione (PCT Patent Publication WO 00/27831) (18 g, 0.1 mol) and acetic acid (1.2 g, 0.02 mol) in ethyl acetate (200 mL) was warmed to 35° C., and aqueous methylamine (40%, 9.0 g, 0.12 mol) was added dropwise over 50 minutes at 35-37° C. Then more aqueous methylamine (40%, 0.9 g, 12 mmol) was added, and the mixture was stirred an additional 2.5 h at 36° C. Then water (20 mL) was added, the layers were separated, and the organic layer was washed with water, dried (MgSO$_4$), and evaporated to afford the title compound, 15.45 g (92%).
$^1$H NMR (CDCl$_3$) δ 2.14 (s, 3H), 2.94 (d, 3H, J=5 Hz), 5.37 (br s, 2H), 6.21 (br s, 1H), 6.56 (t, J=7.5 Hz, 1H), 7.10 (dd, J=7.5 Hz, 7.5 Hz, 1H), 7.18 (dd, J=7.5 Hz, 7.5 Hz, 1H).

Step B: Preparation of
2-amino-5-chloro-N,3-dimethylbenzamide

A mixture of 2-amino-N,3-dimethylbenzamide (i.e. the product of Step A) (16.6 g, 100 mmol) and N,N-dimethylformamide (15.0 g) was cooled to 10° C. and concentrated hydrochloric acid (70 g, 700 mmol) was slowly added. Then the mixture was heated to 30° C., and 30% aqueous hydrogen peroxide (18.5 g, 160 mmol) was added dropwise over 15 minutes at 30-35° C. After stirring at about 35° C. for 3 h, the mixture was cooled to about 10° C., and then water (200 mL) was added. Sodium sulfite (7.56 g, 60 mmol) was added, and then the pH was adjusted to 2.2 by slow addition of 50% aqueous sodium hydroxide (38.1 g). After stirring at 10° C. for 15 minutes, the mixture was filtered, and the solids were washed with water (2×50 mL), and dried in the vacuum oven to afford the title compound as pink solids, 14.61 g (72.7% yield). Quantitative HPLC of the solid product showed 99.1 wt % of the title compound.

EXAMPLE 6

Preparation of
2-amino-5-cyano-N,3-dimethylbenzamide

Step A: Preparation of
2-amino-5-bromo-N,3-dimethylbenzamide

A mixture of 2-amino-N,3-dimethylbenzamide (i.e. the product of Step A of Example 5) (14 g, 85 mmol), acetic acid (50 mL), and water (50 mL) was cooled to 12° C., and concentrated hydrobromic acid (28.5 g, 0.34 mol) was added over 10 minutes at this temperature. Then 30% aqueous hydrogen peroxide (9 g, 0.08 mol) was added over 5 minutes at 10-11° C., and the mixture was allowed to warm slowly to room temperature while being stirred for 2.5 h. Then more concentrated hydrobromic acid (2.9 g) was added, and the mixture was stirred overnight at room temperature. To the mixture was then added water (50 mL) and sodium bisulfite (1.5 g), and then the pH was adjusted to 5-6 by the addition of 50% aqueous sodium hydroxide (~15 mL). The mixture was filtered, and the solids were washed with water and dried in vacuo to afford the title compound, 19.5 g (94%).
$^1$H NMR (CDCl$_3$) δ 2.14 (s, 3H), 2.95 (d, J=5 Hz, 3H), 5.55 (br s, 2H), 6.01 (br s, 1H), 7.21 (m, 1H), 7.30 (d, J=2 Hz, 1H).

Step B: Preparation of
2-amino-5-cyano-N,3-dimethylbenzamide

A flask purged with dry nitrogen was charged with palladium(II) acetate (370 mg, 1.64 mmol), 1,4-bis(diphenylphosphino)butane (850 mg, 2 mmol), activated zinc powder (500 mg, 7.64 mmol), zinc(II) cyanide (51 g, 434 mmol), and 2-amino-5-bromo-N,3-dimethylbenzamide (i.e. the product of Step A) (200 g, 820 mmol). Then freshly degassed N,N-dimethylformamide (500 mL) was added, and the mixture was heated at 130° C. for 25.5 h. Then the temperature was reduced to 95° C., and acetic acid (200 mL) was added. The mixture was sparged with nitrogen to remove hydrogen cyanide through scrubbers charged with aqueous sodium hydroxide and sodium hypochlorite solutions while cooling to room temperature. Then water (1500 mL) was added over 1.5 h, and sparging with nitrogen was continued overnight. Then the mixture was filtered, and the solids were washed with water and dried in a vacuum oven to afford the title compound as fluffy, light yellow solids, 141.5 g (90.9% yield).
$^1$H NMR (CDCl$_3$) δ 2.16 (s, 3H), 2.98 (d, J=4.8 Hz, 3H), 6.17 (br s, 3H), 7.34 (d, J=1.8 Hz, 1H), 7.56 (d, J=1.8 Hz, 1H).

EXAMPLE 7

Preparation of 3-bromo-N-[4-chloro-2-methyl-6-
[(methylamino)carbonyl]phenyl]-1-(3-chloro-2-pyridinyl)-1H-pyrazole-5-carboxamide To a mixture of 3-bromo-1-(3-chloro-2-pyridinyl)-1H-pyrazole-5-carboxylic acid (see PCT Patent Publication WO 03/015519 for preparation) (93.6% purity, 16.16 g, 50.0 mmol) and 2-amino-5-chloro-N,3-dimethylbenzamide (i.e. the product of Examples 1, 3, 4 and 5) (10.43 g, 52.5 mmol) in acetonitrile (35 mL) was added 3-picoline (12.65 mL, 12.11 g, 130 mmol). The mixture was cooled to −5° C., and then a solution of methanesulfonyl chloride (4.64 mL, 6.89 g, 60 mmol) in acetonitrile (10 mL) was added dropwise at −5 to 0° C. The mixture was stirred for 15 minutes at this temperature, and then for 3 h at room temperature. Then water (15 mL) was added dropwise and the mixture was cooled to 0° C. for 1 h. The mixture was filtered, and the solids were washed with 3:1 acetonitrile-water (2×10 mL), and then with acetonitrile (2×10 mL), and dried under nitrogen to afford the title compound as a light tan powder, 23.98 g (92.9% uncorrected yield), m.p. 239 to 240° C.

$^1$H NMR (CDCl$_3$) δ 2.18 (s, 3H), 2.95 (s, 3H), 6.21 (m, 1H), 7.10 (s, 1H), 7.24 (m, 2H), 7.39 (m, 1H), 7.80 (d, 1H), 8.45 (d, 1H).

EXAMPLE 8

Preparation of 3-bromo-N-[4-chloro-2-methyl-6-[(methylamino)carbonyl]phenyl]-1-(3-chloro-2-pyridinyl)-1H-pyrazole-5-carboxamide using pyridine as the base To a mixture of 3-bromo-1-(3-chloro-2-pyridinyl)-1H-pyrazole-5-carboxylic acid (See PCT Patent Publication WO 03/015519 for preparation) (6.05 g, 20.0 mmol) and 2-amino-5-chloro-N,3-dimethylbenzamide (i.e. the product of Examples 1, 3, 4 and 5) (4.17 g, 21.0 mmol) in acetonitrile (18 mL) was added pyridine (4.20 mL, 4.11 g, 52 mmol). The mixture was cooled to −5° C., and then methanesulfonyl chloride (1.86 mL, 2.75 g, 24 mmol) was added dropwise at −5 to 0° C. The mixture was stirred for 1 h at this temperature, and then for 3 h at room temperature. Then water (6 mL) was added dropwise and the mixture was stirred at room temperature for 1 h. The mixture was filtered, and the solids were washed with 3:1 acetonitrile-water (2×4 mL), and then with acetonitrile (2×4 mL), and dried under nitrogen to afford the title compound as an off-white powder, 9.35 g (96.8% uncorrected yield).

EXAMPLE 9

Preparation of 3-bromo-N-[4-chloro-2-methyl-6-[(methylamino)carbonyl]phenyl]-1-(3-chloro-2-pyridinyl)-1H-pyrazole-5-carboxamide using "mixed picolines" as the base To a mixture of 3-bromo-1-(3-chloro-2-pyridinyl)-1H-pyrazole-5-carboxylic acid (see PCT Patent Publication WO 03/015519 for preparation) (6.05 g, 20.0 mmol) and 2-amino-5-chloro-N,3-dimethylbenzamide (i.e. the product of Examples 1, 3, 4 and 5) (4.17 g, 21.0 mmol) in acetonitrile (18 mL) was added 3-picoline (2.53 mL, 2.42 g, 26 mmol), followed by 4-picoline (2.53 mL, 2.42 g, 26 mmol). The mixture became much thicker after the 4-picoline addition. The mixture was cooled to −5° C., and then methanesulfonyl chloride (1.86 mL, 2.75 g, 24 mmol) was added dropwise at −5 to 0° C. The mixture was stirred for 2 h at 0 to 5° C. Then water (6 mL) was added dropwise and the mixture was stirred at 0° C. for 1 h. The mixture was filtered, and the solids were washed with 3:1 acetonitrile-water (2×4 mL), and then with acetonitrile (2×4 mL), and dried under nitrogen to afford the title compound as a yellow powder, 9.15 g (94.7% uncorrected yield).

EXAMPLE 10

Preparation of 3-bromo-N-[4-chloro-2-methyl-6-[(methylamino)carbonyl]phenyl]-1-(3-chloro-2-pyridinyl)-1H-pyrazole-5-carboxamide in acetone To a mixture of 3-bromo-1-(3-chloro-2-pyridinyl)-1H-pyrazole-5-carboxylic acid (see PCT Patent Publication WO 03/015519 for preparation) (6.05 g, 20.0 mmol) and 2-amino-5-chloro-N,3-dimethylbenzamide (i.e. the product of Examples 1, 3, 4 and 5) (4.17 g, 21.0 mmol) in acetone (18 mL) was added 3-picoline (5.06 mL, 4.84 g, 52 mmol). The mixture was cooled to −5° C., and then methanesulfonyl chloride (1.86 mL, 2.75 g, 24 mmol) was added dropwise at −5 to 0° C. The mixture was stirred for 3 h at 0-5° C. Then water (9 mL) was added dropwise and the mixture was stirred at 0° C. for 1 h. The mixture was filtered, and the solids were washed with ice-cold 2:1 acetone-water (2×4 mL), and dried under nitrogen to afford the title compound as a nearly white powder, 9.32 g (96.4% uncorrected yield).

EXAMPLE 11

Preparation of 3-bromo-N-[4-chloro-2-methyl-6-[(methylamino)carbonyl]phenyl]-1-(3-chloro-2-pyridinyl)-1H-pyrazole-5-carboxamide in tetrahydrofuran To a mixture of 3-bromo-1-(3-chloro-2-pyridinyl)-1H-pyrazole-5-carboxylic acid (see PCT Patent Publication WO 03/015519 for preparation) (6.05 g, 20.0 mmol) and 2-amino-5-chloro-N,3-dimethylbenzamide (product of Examples 1, 3, 4 and 5) (4.17 g, 21.0 mmol) in tetrahydrofuran (THF, 18 mL) was added 3-picoline (5.06 mL, 4.84 g, 52 mmol). The mixture was cooled to −5° C., and then methanesulfonyl chloride (1.86 mL, 2.75 g, 24 mmol) was added dropwise at −5 to 0° C. The mixture was stirred for 3 h at 0 to 5° C. Then water (9 mL) was added dropwise and the mixture was stirred at 0° C. for 1 h. The mixture was filtered, and the solids were washed with ice-cold 2:1 THF-water (2×4 mL), and dried under nitrogen to afford the title compound as a nearly white powder, 6.93 g (71.7% uncorrected yield).

EXAMPLE 12

Preparation of 3-bromo-N-[4-chloro-2-methyl-6-[(methylamino)carbonyl]phenyl]-1-(3-chloro-2-pyridinyl)-1H-pyrazole-5-carboxamide in dichloromethane To a mixture of 3-bromo-1-(3-chloro-2-pyridinyl)-1H-pyrazole-5-carboxylic acid (see PCT Patent Publication WO 03/015519 for preparation) (6.05 g, 20.0 mmol) and 2-amino-5-chloro-N,3-dimethylbenzamide (i.e. the product of Examples 1, 3, 4 and 5) (4.17 g, 21.0 mmol) in dichloromethane (18 mL) was added 3-picoline (5.06 mL, 4.84 g, 52 mmol). The mixture was cooled to −5° C., and then methanesulfonyl chloride (1.86 mL, 2.75 g, 24 mmol) was added dropwise at −5 to 0° C. The mixture was stirred for 3 h at 0 to 5° C. Then water (9 mL) was added dropwise. More dichloromethane (18 mL) was added to stir the thick suspension and the mixture was stirred at 0° C. for 1 h. The mixture was filtered, and the solids were washed with ice-cold 2:1 dichloromethane-water (2×4.5 mL), and dried under nitrogen to afford the title compound as a nearly white powder, 8.86 g (91.7% uncorrected yield).

EXAMPLE 13

Preparation of 3-bromo-N-[4-chloro-2-methyl-6-[(methylamino)carbonyl]phenyl]-1-(3-chloro-2-pyridinyl)-1H-pyrazole-5-carboxamide in Propionitrile To a mixture of 3-bromo-1-(3-chloro-2-pyridinyl)-1H-pyrazole-5-carboxylic acid (see PCT Patent Publication WO 03/015519 for preparation) (6.05 g, 20.0 mmol) and 2-amino-5-chloro-N,3-dimethylbenzamide (i.e. the product of Examples 1, 3, 4 and 5) (4.17 g, 21.0 mmol) in propionitrile (18 mL) was added 3-picoline (5.06 mL, 4.84 g, 52 mmol). The mixture was cooled to −5° C., and then methanesulfonyl chloride (1.86 mL, 2.75 g, 24 mmol) was added dropwise at −5 to 0° C. The mixture was stirred for 1 h at 0 to 5° C., and then for 3 h at room temperature. Then water (9 mL) was added dropwise and the mixture was stirred at room temperature for 1 h. The mixture was filtered, and the solids were washed with 3:1 propionitrile-water (2×4 mL), then with propionitrile (2×4 mL), and dried under nitrogen to afford the title compound as a nearly white powder, 9.37 g (97.0% uncorrected yield).

EXAMPLE 14

Preparation of 3-bromo-N-[4-chloro-2-methyl-6-[(methylamino)carbonyl]phenyl]-1-(3-chloro-2-pyridinyl)-1H-pyrazole-5-carboxamide in methyl ethyl ketone To a mixture of 3-bromo-1-(3-chloro-2-pyridinyl)-1H-pyrazole-5-carboxylic acid (see PCT Patent Publication WO 03/015519 for preparation) (6.05 g, 20.0 mmol) and 2-amino-5-chloro-N,3-dimethylbenzamide (product of Examples 1, 3, 4 and 5) (4.17 g, 21.0 mmol) in methyl ethyl ketone (MEK, 18 mL) was added 3-picoline (5.06 mL, 4.84 g, 52 mmol). The mixture was cooled to −5° C., and then methanesulfonyl chloride (1.86 mL, 2.75 g, 24 mmol) was added dropwise at −5 to 0° C. The mixture was stirred for 3 h at 0 to 5° C. Then water (9 mL) was added dropwise and the mixture was stirred at room temperature for 1 h. The mixture was filtered, and the solids were washed with 3:1 MEK-water (2×4 mL), then with MEK (2×4 mL), and dried under nitrogen to afford the title compound as a nearly white powder, 9.27 g (95.9% uncorrected yield).

EXAMPLE 15

Preparation of 3-bromo-1-(3-chloro-2-pyridinyl)-N-[4-cyano-2-methyl-6-[(methylamino)-carbonyl]phenyl]-1H-pyrazole-5-carboxamide To a mixture of 3-bromo-1-(3-chloro-2-pyridinyl)-1H-pyrazole-5-carboxylic acid (see PCT Patent Publication WO 03/015519 for preparation) (95.4% purity, 15.85 g, 50.0 mmol) and 2-amino-5-cyano-N,3-dimethylbenzamide (i.e. the product of Example 6) (9.93 g, 52.5 mmol) in acetonitrile (120 mL) was added 3-picoline (17.5 mL, 16.7 g, 180 mmol). The mixture was cooled to −10° C., and then a solution of methanesulfonyl chloride (5.4 mL, 8.0 g, 70 mmol) was added dropwise at −10 to −5° C. The mixture was stirred for 5 minutes at this temperature, and then for 3 h at 0 to 5° C. Then water (55 mL) was added dropwise. The mixture was stirred for 15 minutes, then concentrated hydrochloric acid (5.0 mL, 60 mmol) was added dropwise and the mixture was stirred at 0 to 5° C. for 1 h. Then the mixture was filtered, and the solids were washed with 2:1 acetonitrile-water (2×10 mL), and then with acetonitrile (2×10 mL), and dried under nitrogen to afford the title compound as an off-white powder, 24.70 g (99.5% uncorrected yield), m.p. 177-181° C. (decomposition).

Crystallization of the crude product (5.00 g) from 1-propanol (50 mL) afforded the title compound as white crystals, 4.44 g (88.8% recovery), m.p. 217-219° C.

$^1$H NMR (DMSO-$d_6$) δ 2.21 (s, 3H), 2.67 (d, J=4.8 Hz, 3H), 7.41 (s, 1H), 7.60 (m, 1H), 7.76 (d, J=1.8 Hz, 1H), 7.87 (d, J=1.8 Hz, 1H), 8.16 (dd, 1H), 8.36 (m, 1H), 8.49 (dd, 1H).

EXAMPLE 16

Preparation of 3-bromo-1-(3-chloro-2-pyridinyl)-N-[4-cyano-2-methyl-6-[(methylamino)-carbonyl]phenyl]-1H-pyrazole-5-carboxamide using pyridine as the base To a mixture of 3-bromo-1-(3-chloro-2-pyridinyl)-1H-pyrazole-5-carboxylic acid (see PCT Patent Publication WO 03/015519 for preparation) (95.4% purity, 15.85 g, 50.0 mmol) and 2-amino-5-cyano-N,3-dimethylbenzamide (product of Example 6) (9.93 g, 52.5 mmol) in acetonitrile (120 mL) was added pyridine (14.6 mL, 14.3 g, 180 mmol). The mixture was cooled to −10° C., and then a solution of methanesulfonyl chloride (5.4 mL, 8.0 g, 70 mmol) was added dropwise at −10 to −5° C. The mixture was stirred for 5 minutes at this temperature, and then for 3 h at 0 to 5° C. Then the mixture was warmed to room temperature, and water (85 mL) was added dropwise. The mixture was stirred for 15 minutes, then concentrated hydrochloric acid (5.0 mL, 60 mmol) was added dropwise and the mixture was stirred for 1 h. Then the mixture was filtered, and the solids were washed with 4:3 acetonitrile-water (2×10 mL), and then with acetonitrile (2×10 mL), and dried under nitrogen to afford the title compound as an off-white powder, 24.29 g (97.9% uncorrected yield).

EXAMPLE 17

Preparation of 3-bromo-1-(3-chloro-2-pyridinyl)-N-[4-cyano-2-methyl-6-[(methylamino)-carbonyl]phenyl]-1H-pyrazole-5-carboxamide Using 2-picoline as the base To a mixture of 3-bromo-1-(3-chloro-2-pyridinyl)-1H-pyrazole-5-carboxylic acid (see PCT Patent Publication WO 03/015519 for preparation) (96.7% purity, 15.64 g, 50.0 mmol) and 2-amino-5-cyano-N,3-dimethylbenzamide (i.e. the product of Example 6) (9.93 g, 52.5 mmol) in acetonitrile (120 mL) was added 2-picoline (17.8 mL, 16.8 g, 180 mmol). The mixture was cooled to −10° C., and then a solution of methanesulfonyl chloride (5.4 mL, 8.0 g, 70 mmol) was added dropwise at −10 to −5° C. The mixture was stirred for 5 minutes at this temperature, then for 3 h at 0 to 5° C. and then for 18 h at room temperature. Then water (25 mL) was added dropwise. The mixture was stirred for 15 minutes, then concentrated hydrochloric acid (5.0 mL, 60 mmol) was added dropwise and the mixture was stirred for 1 h. Then the mixture was filtered, and the solids were washed with 4:1 acetonitrile-water (2×10 mL), and then with acetonitrile (2×10 mL), and dried under nitrogen to afford the title compound as an off-white powder, 22.52 g (92.0% uncorrected yield).

EXAMPLE 18

Preparation of 3-bromo-1-(3-chloro-2-pyridinyl)-N-[4-cyano-2-methyl-6-[(methylamino)-carbonyl]phenyl]-1H-pyrazole-5-carboxamide using 2,6-lutidine as the base To a mixture of 3-bromo-1-(3-chloro-2-pyridinyl)-1H-pyrazole-5-carboxylic acid (see PCT Patent Publication WO 03/015519 for preparation) (97.6% purity, 15.50 g, 50.0 mmol) and 2-amino-5-cyano-N,3-dimethylbenzamide (i.e. the product of Example 6) (9.93 g, 52.5 mmol) in acetonitrile (120 mL) was added 2,6-lutidine (21.0 mL, 19.3 g, 180 mmol). The mixture was cooled to −10° C., and then a solution of methanesulfonyl chloride (5.4 mL, 8.0 g, 70 mmol) was added dropwise at −10 to-5° C. The mixture was stirred for 5 minutes at this temperature, then for 1 h at 0 to 5° C. and then for 1 h at room temperature. NMR analysis of the reaction mass showed that little of the title compound was present, but 10.3% of the cyclized derivative had formed. Additional 2,6-lutidine (11.7 mL, 10.8 g, 100 mmol) and methanesulfonyl chloride (3.9 mL, 5.8 g, 50 mmol) were added and the mixture was stirred for 22 h at room temperature. NMR analysis of the reaction mass showed 9.6% of the title compound and 89.8% of the cyclized derivative had formed. Water (55 mL) was added dropwise. The mixture was stirred for 15 minutes, then concentrated hydrochloric acid (5.0 mL, 60 mmol) was added dropwise and the mixture was stirred for 1 h. Then the mixture was filtered, and the solids were washed with 2:1 acetonitrile-water (2×10 mL), and then with acetonitrile (2×10 mL), and dried under nitrogen to afford a light yellow powder, 21.92 g. This solid was suspended in acetonitrile (60 mL), and water (10 mL) and hydrochloric acid (1N, 10 mL) were added, and the mixture was stirred at room temperature for 30 minutes. Then the mixture was filtered and the solids were washed with 3:1 acetonitrile-water (2×10 mL), and then with acetonitrile (2×10 mL), and dried in the vacuum oven to afford the title compound as an off-white powder, 20.72 g (85.4% uncorrected yield).

EXAMPLE 19

Preparation of 3-bromo-1-(3-chloro-2-pyridinyl)-N-[4-cyano-2-methyl-6-[(methylamino)-carbonyl]phenyl]-1H-pyrazole-5-carboxamide in acetone To a mixture of 3-bromo-1-(3-chloro-2-pyridinyl)-1H-pyrazole-5-carboxylic acid (see PCT Patent Publication WO 03/015519 for preparation) (97.6% purity, 15.50 g, 50.0 mmol) and 2-amino-5-cyano-N,3-dimethylbenzamide (i.e. the product of Example 6) (9.93 g, 52.5 mmol) in acetone (120 mL) was added 3-picoline (17.5 mL, 16.7 g, 180 mmol). The mixture was cooled to −10° C., and then a solution of methanesulfonyl chloride (5.4 mL, 8.0 g, 70 mmol) was added dropwise at −10 to −5° C. The mixture was stiffed for 5 minutes at this temperature, then for 3 h at 0 to 5° C. Then water (55 mL) was added dropwise. The mixture was stirred for 15 minutes, then concentrated hydrochloric acid (5.0 mL, 60 mmol) was added dropwise and the mixture was stirred at 0 to 5° C. for 1 h. Then the mixture was filtered, and the solids were washed with 2:1 acetone-water (3×10 mL), and dried under nitrogen to afford the title compound as an off-white powder, 24.07 g (99.2% uncorrected yield). Karl Fisher titration (KFT) of this solid showed that it contained 5.5 wt % water. A portion of the solid (23.35 g) was dried in the vacuum oven to afford the title compound as an off-white powder, 22.16 g, now containing 0.76 wt % water by KFT.

EXAMPLE 20

Preparation of 3-bromo-1-(3-chloro-2-pyridinyl)-N-[4-cyano-2-methyl-6-[(methylamino)-carbonyl]phenyl]-1H-pyrazole-5-carboxamide in propionitrile To a mixture of 3-bromo-1-(3-chloro-2-pyridinyl)-1H-pyrazole-5-carboxylic acid (see PCT Patent Publication WO 03/015519 for preparation) (97.6% purity, 15.50 g, 50.0 mmol) and 2-amino-5-cyano-N,3-dimethylbenzamide (product of Example 6) (9.93 g, 52.5 mmol) in propionitrile (120 mL) was added 3-picoline (17.5 mL, 16.7 g, 180 mmol). The mixture was cooled to −10° C., and then a solution of methanesulfonyl chloride (5.4 mL, 8.0 g, 70 mmol) was added dropwise at −10 to −5° C. The mixture was stirred for 5 minutes at this temperature, then for 4 h at 0 to 5° C. Then water (55 mL) was added dropwise. The mixture was stirred for 15 minutes, then concentrated hydrochloric acid (5.0 mL, 60 mmol) was added dropwise and the mixture was stirred at 0 to 5° C. for 1 h. Then the mixture was filtered, and the solids were washed with 2:1 propionitrile-water (2×10 mL), then with propionitrile (2×10 mL), and dried under nitrogen to afford the title compound as an off-white powder, 21.85 g (90.1% uncorrected yield). Karl Fisher titration (KFT) of this solid showed that it contained 5.4 wt % water. A portion of the solid (21.03 g) was dried in the vacuum oven to afford the title compound as an off-white powder, 20.07 g, now containing 0.9 wt % water by KFT.

The following abbreviations are used in the Tables which follow: t means tertiary, s means secondary, n means normal, i means iso, Me means methyl, Et means ethyl, Pr means propyl, i-Pr means isopropyl, and Bu means butyl. By the procedures described herein together with methods known in the art, the following compounds of Table 1 can be prepared and used in the method of the present invention.

TABLE 1

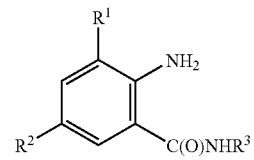

3

| $R^1$ | $R^2$ | $R^3$ | $R^1$ | $R^2$ | $R^3$ | $R^1$ | $R^2$ | $R^3$ |
|---|---|---|---|---|---|---|---|---|
| $CH_3$ | Cl | H | $CH_3$ | I | n-Bu | Cl | Br | i-Pr |
| $CH_3$ | Cl | Me | $CH_3$ | I | s-Bu | Cl | Br | i-Bu |
| $CH_3$ | Cl | Et | $CH_3$ | I | i-Bu | Cl | Br | n-Pr |
| $CH_3$ | Cl | i-Pr | $CH_3$ | CN | H | Cl | Br | n-Bu |
| $CH_3$ | Cl | t-Bu | $CH_3$ | CN | Me | Cl | Br | s-Bu |
| $CH_3$ | Cl | n-Pr | $CH_3$ | CN | Et | Cl | Br | i-Bu |
| $CH_3$ | Cl | n-Bu | $CH_3$ | CN | i-Pr | Cl | I | H |
| $CH_3$ | Cl | s-Bu | $CH_3$ | CN | t-Bu | Cl | I | Me |
| $CH_3$ | Cl | i-Bu | $CH_3$ | CN | n-Pr | Cl | I | Et |
| $CH_3$ | Br | H | $CH_3$ | CN | n-Bu | Cl | I | i-Pr |
| $CH_3$ | Br | Me | $CH_3$ | CN | s-Bu | Cl | I | t-Bu |
| $CH_3$ | Br | Et | $CH_3$ | CN | i-Bu | Cl | I | n-Pr |
| $CH_3$ | Br | i-Pr | Cl | Cl | H | Cl | I | n-Bu |
| $CH_3$ | Br | t-Bu | Cl | Cl | Me | Cl | I | s-Bu |
| $CH_3$ | Br | n-Pr | Cl | Cl | Et | Cl | I | i-Bu |
| $CH_3$ | Br | n-Bu | Cl | Cl | i-Pr | Cl | CN | H |
| $CH_3$ | Br | s-Bu | Cl | Cl | t-Bu | Cl | CN | Me |
| $CH_3$ | Br | i-Bu | Cl | Cl | n-Pr | Cl | CN | Et |
| $CH_3$ | I | H | Cl | Cl | n-Bu | Cl | CN | i-Pr |
| $CH_3$ | I | Me | Cl | Cl | s-Bu | Cl | CN | t-Bu |
| $CH_3$ | I | Et | Cl | Cl | i-Bu | Cl | CN | n-Pr |
| $CH_3$ | I | i-Pr | Cl | Br | H | Cl | CN | n-Bu |

TABLE 1-continued

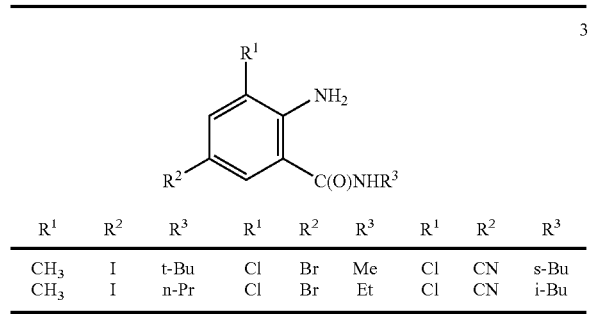

| R¹ | R² | R³ | R¹ | R² | R³ | R¹ | R² | R³ |
|---|---|---|---|---|---|---|---|---|
| CH₃ | I | t-Bu | Cl | Br | Me | Cl | CN | s-Bu |
| CH₃ | I | n-Pr | Cl | Br | Et | Cl | CN | i-Bu |

Table 2 illustrates particular transformations to prepare compounds of Formula 1 according 5 to a method of the present invention.

TABLE 2

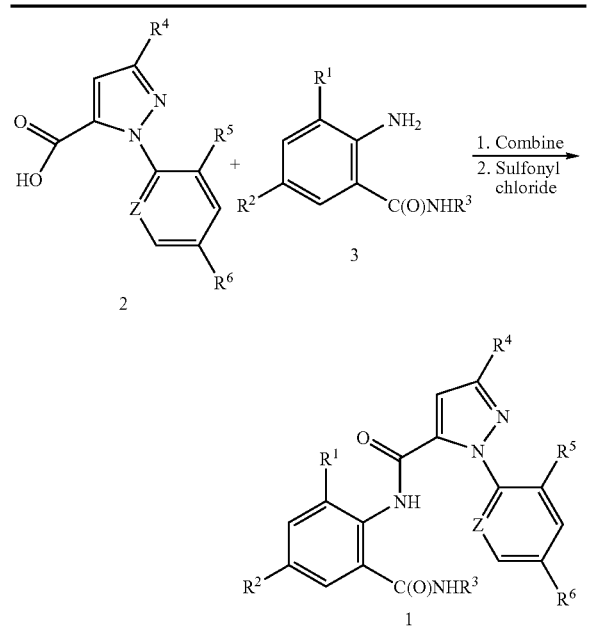

| R¹ | R² | R⁴ | R³ | Z | R⁵ |
|---|---|---|---|---|---|
| CH₃ | Cl | CF₃ | H | N | F |
| CH₃ | Cl | CF₃ | Me | N | F |
| CH₃ | Cl | CF₃ | Et | N | F |
| CH₃ | Cl | CF₃ | i-Pr | N | F |
| CH₃ | Cl | CF₃ | t-Bu | N | F |
| CH₃ | Cl | CF₃ | H | N | Cl |
| CH₃ | Cl | CF₃ | Me | N | Cl |
| CH₃ | Cl | CF₃ | Et | N | Cl |
| CH₃ | Cl | CF₃ | i-Pr | N | Cl |
| CH₃ | Cl | CF₃ | t-Bu | N | Cl |
| CH₃ | Cl | CF₃ | H | N | Br |
| CH₃ | Cl | CF₃ | Me | N | Br |
| CH₃ | Cl | CF₃ | Et | N | Br |
| CH₃ | Cl | CF₃ | i-Pr | N | Br |
| CH₃ | Cl | CF₃ | t-Bu | N | Br |
| CH₃ | Cl | Cl | H | N | F |
| CH₃ | Cl | Cl | Me | N | F |
| CH₃ | Cl | Cl | Et | N | F |
| CH₃ | Cl | Cl | i-Pr | N | F |
| CH₃ | Cl | Cl | t-Bu | N | F |
| CH₃ | Cl | Cl | H | N | Cl |
| CH₃ | Cl | Cl | Me | N | Cl |
| CH₃ | Cl | Cl | Et | N | Cl |
| CH₃ | Cl | Cl | i-Pr | N | Cl |

TABLE 2-continued

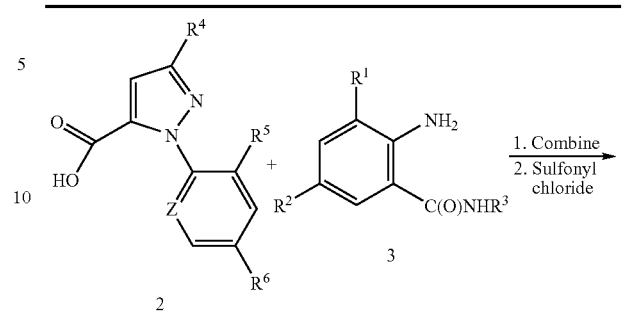

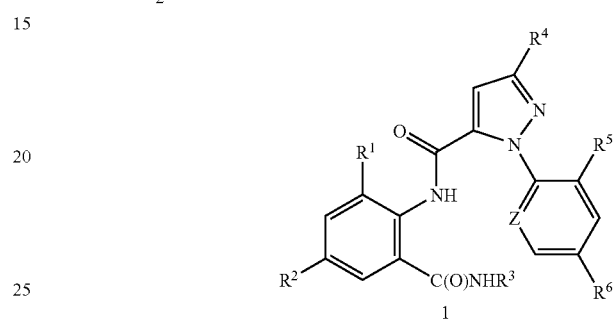

| R¹ | R² | R⁴ | R³ | Z | R⁵ |
|---|---|---|---|---|---|
| CH₃ | Cl | Cl | t-Bu | N | Cl |
| CH₃ | Cl | Cl | H | N | Br |
| CH₃ | Cl | Cl | Me | N | Br |
| CH₃ | Cl | Cl | Et | N | Br |
| CH₃ | Cl | Cl | i-Pr | N | Br |
| CH₃ | Cl | Cl | t-Bu | N | Br |
| CH₃ | Cl | Br | H | N | F |
| CH₃ | Cl | Br | Me | N | F |
| CH₃ | Cl | Br | Et | N | F |
| CH₃ | Cl | Br | i-Pr | N | F |
| CH₃ | Cl | Br | t-Bu | N | F |
| CH₃ | Cl | Br | H | N | Cl |
| CH₃ | Cl | Br | Me | N | Cl |
| CH₃ | Cl | Br | Et | N | Cl |
| CH₃ | Cl | Br | i-Pr | N | Cl |
| CH₃ | Cl | Br | t-Bu | N | Cl |
| CH₃ | Cl | Br | H | N | Br |
| CH₃ | Cl | Br | Me | N | Br |
| CH₃ | Cl | Br | Et | N | Br |
| CH₃ | Cl | Br | i-Pr | N | Br |
| CH₃ | Cl | Br | t-Bu | N | Br |
| CH₃ | Cl | OCH₂CF₃ | H | N | F |
| CH₃ | Cl | OCH₂CF₃ | Me | N | F |
| CH₃ | Cl | OCH₂CF₃ | Et | N | F |
| CH₃ | Cl | OCH₂CF₃ | i-Pr | N | F |
| CH₃ | Cl | OCH₂CF₃ | t-Bu | N | F |
| CH₃ | Cl | OCH₂CF₃ | H | N | Cl |
| CH₃ | Cl | OCH₂CF₃ | Me | N | Cl |
| CH₃ | Cl | OCH₂CF₃ | Et | N | Cl |
| CH₃ | Cl | OCH₂CF₃ | i-Pr | N | Cl |
| CH₃ | Cl | OCH₂CF₃ | t-Bu | N | Cl |
| CH₃ | Cl | OCH₂CF₃ | H | N | Br |
| CH₃ | Cl | OCH₂CF₃ | Me | N | Br |
| CH₃ | Cl | OCH₂CF₃ | Et | N | Br |
| CH₃ | Cl | OCH₂CF₃ | i-Pr | N | Br |
| CH₃ | Cl | OCH₂CF₃ | t-Bu | N | Br |
| CH₃ | Br | CF₃ | H | N | F |
| CH₃ | Br | CF₃ | Me | N | F |
| CH₃ | Br | CF₃ | Et | N | F |
| CH₃ | Br | CF₃ | i-Pr | N | F |
| CH₃ | Br | CF₃ | t-Bu | N | F |
| CH₃ | Br | CF₃ | H | N | Cl |
| CH₃ | Br | CF₃ | Me | N | Cl |
| CH₃ | Br | CF₃ | Et | N | Cl |
| CH₃ | Br | CF₃ | i-Pr | N | Cl |
| CH₃ | Br | CF₃ | t-Bu | N | Cl |
| CH₃ | Br | CF₃ | H | N | Br |

TABLE 2-continued

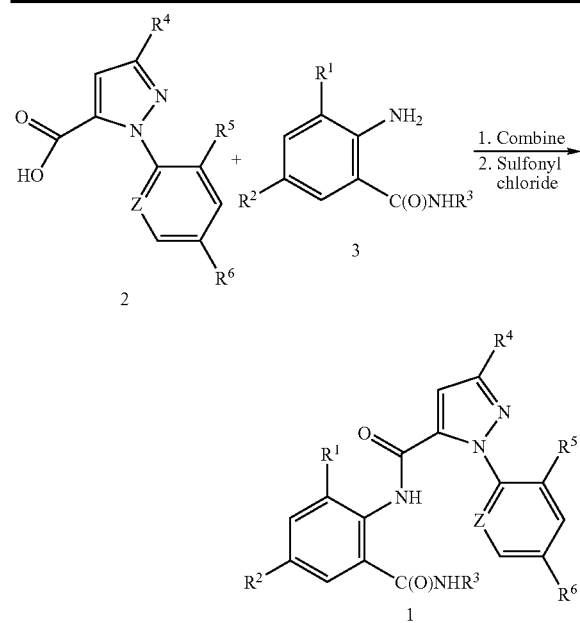

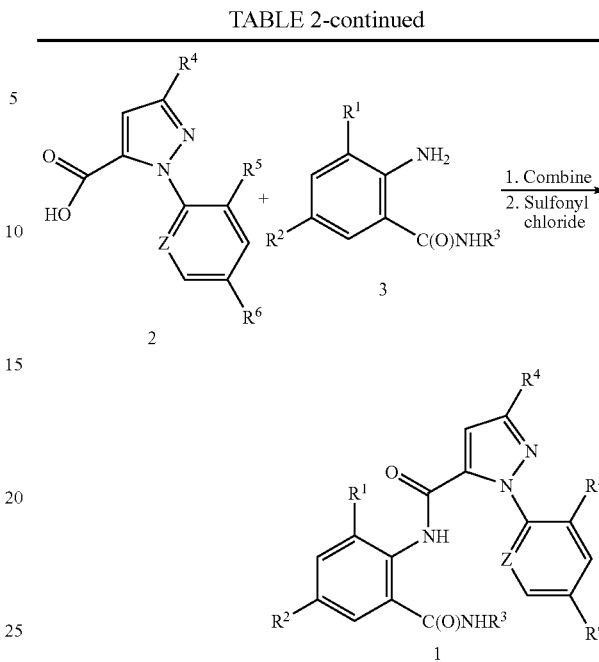

| R¹ | R² | R⁴ | R³ | Z | R⁵ |
|---|---|---|---|---|---|
| CH₃ | Br | CF₃ | Me | N | Br |
| CH₃ | Br | CF₃ | Et | N | Br |
| CH₃ | Br | CF₃ | i-Pr | N | Br |
| CH₃ | Br | CF₃ | t-Bu | N | Br |
| CH₃ | Br | Cl | H | N | F |
| CH₃ | Br | Cl | Me | N | F |
| CH₃ | Br | Cl | Et | N | F |
| CH₃ | Br | Cl | i-Pr | N | F |
| CH₃ | Br | Cl | t-Bu | N | F |
| CH₃ | Br | Cl | H | N | Cl |
| CH₃ | Br | Cl | Me | N | Cl |
| CH₃ | Br | Cl | Et | N | Cl |
| CH₃ | Br | Cl | i-Pr | N | Cl |
| CH₃ | Br | Cl | t-Bu | N | Cl |
| CH₃ | Br | Cl | H | N | Br |
| CH₃ | Br | Cl | Me | N | Br |
| CH₃ | Br | Cl | Et | N | Br |
| CH₃ | Br | Cl | i-Pr | N | Br |
| CH₃ | Br | Cl | t-Bu | N | Br |
| CH₃ | Br | Br | H | N | F |
| CH₃ | Br | Br | Me | N | F |
| CH₃ | Br | Br | Et | N | F |
| CH₃ | Br | Br | i-Pr | N | F |
| CH₃ | Br | Br | t-Bu | N | F |
| CH₃ | Br | Br | H | N | Cl |
| CH₃ | Br | Br | Me | N | Cl |
| CH₃ | Br | Br | Et | N | Cl |
| CH₃ | Br | Br | i-Pr | N | Cl |
| CH₃ | Br | Br | t-Bu | N | Cl |
| CH₃ | Br | Br | H | N | Br |
| CH₃ | Br | Br | Me | N | Br |
| CH₃ | Br | Br | Et | N | Br |
| CH₃ | Br | Br | i-Pr | N | Br |
| CH₃ | Br | Br | t-Bu | N | Br |
| CH₃ | Br | OCH₂CF₃ | H | N | F |
| CH₃ | Br | OCH₂CF₃ | Me | N | F |
| CH₃ | Br | OCH₂CF₃ | Et | N | F |
| CH₃ | Br | OCH₂CF₃ | i-Pr | N | F |
| CH₃ | Br | OCH₂CF₃ | t-Bu | N | F |
| CH₃ | Br | OCH₂CF₃ | H | N | Cl |
| CH₃ | Br | OCH₂CF₃ | Me | N | Cl |
| CH₃ | Br | OCH₂CF₃ | Et | N | Cl |
| CH₃ | Br | OCH₂CF₃ | i-Pr | N | Cl |
| CH₃ | Br | OCH₂CF₃ | t-Bu | N | Cl |
| CH₃ | Br | OCH₂CF₃ | H | N | Br |
| CH₃ | Br | OCH₂CF₃ | Me | N | Br |
| CH₃ | Br | OCH₂CF₃ | Et | N | Br |

| R¹ | R² | R⁴ | R³ | Z | R⁵ |
|---|---|---|---|---|---|
| CH₃ | Br | OCH₂CF₃ | i-Pr | N | Br |
| CH₃ | Br | OCH₂CF₃ | t-Bu | N | Br |
| CH₃ | I | CF₃ | H | N | F |
| CH₃ | I | CF₃ | Me | N | F |
| CH₃ | I | CF₃ | Et | N | F |
| CH₃ | I | CF₃ | i-Pr | N | F |
| CH₃ | I | CF₃ | t-Bu | N | F |
| CH₃ | I | CF₃ | H | N | Cl |
| CH₃ | I | CF₃ | Me | N | Cl |
| CH₃ | I | CF₃ | Et | N | Cl |
| CH₃ | I | CF₃ | i-Pr | N | Cl |
| CH₃ | I | CF₃ | t-Bu | N | Cl |
| CH₃ | I | CF₃ | H | N | Br |
| CH₃ | I | CF₃ | Me | N | Br |
| CH₃ | I | CF₃ | Et | N | Br |
| CH₃ | I | CF₃ | i-Pr | N | Br |
| CH₃ | I | CF₃ | t-Bu | N | Br |
| CH₃ | I | Cl | H | N | F |
| CH₃ | I | Cl | Me | N | F |
| CH₃ | I | Cl | Et | N | F |
| CH₃ | I | Cl | i-Pr | N | F |
| CH₃ | I | Cl | t-Bu | N | F |
| CH₃ | I | Cl | H | N | Cl |
| CH₃ | I | Cl | Me | N | Cl |
| CH₃ | I | Cl | Et | N | Cl |
| CH₃ | I | Cl | i-Pr | N | Cl |
| CH₃ | I | Cl | t-Bu | N | Cl |
| CH₃ | I | Cl | H | N | Br |
| CH₃ | I | Cl | Me | N | Br |
| CH₃ | I | Cl | Et | N | Br |
| CH₃ | I | Cl | i-Pr | N | Br |
| CH₃ | I | Cl | t-Bu | N | Br |
| CH₃ | I | Br | H | N | F |
| CH₃ | I | Br | Me | N | F |
| CH₃ | I | Br | Et | N | F |
| CH₃ | I | Br | i-Pr | N | F |
| CH₃ | I | Br | t-Bu | N | F |
| CH₃ | I | Br | H | N | Cl |
| CH₃ | I | Br | Me | N | Cl |
| CH₃ | I | Br | Et | N | Cl |
| CH₃ | I | Br | i-Pr | N | Cl |
| CH₃ | I | Br | t-Bu | N | Cl |
| CH₃ | I | Br | H | N | Br |
| CH₃ | I | Br | Me | N | Br |
| CH₃ | I | Br | Et | N | Br |
| CH₃ | I | Br | i-Pr | N | Br |
| CH₃ | I | Br | t-Bu | N | Br |

TABLE 2-continued

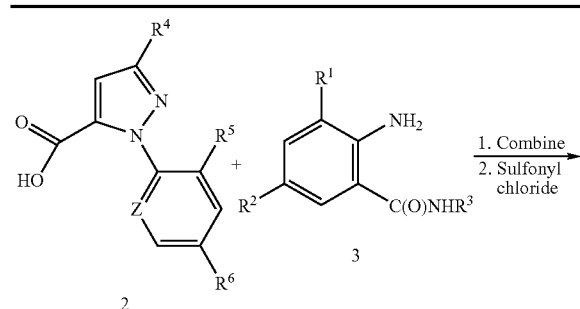

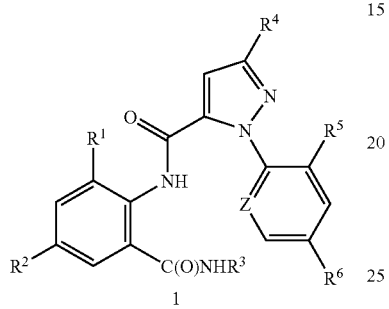

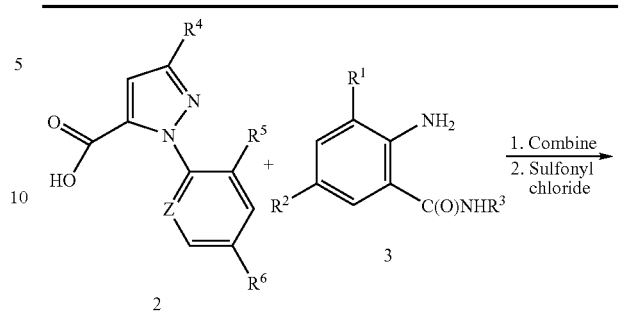

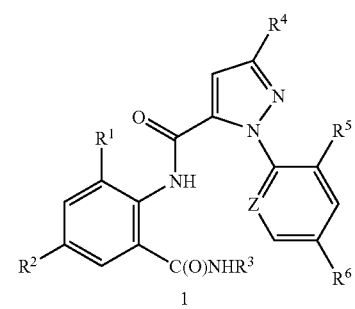

| R¹ | R² | R⁴ | R³ | Z | R⁵ | R¹ | R² | R⁴ | R³ | Z | R⁵ |
|---|---|---|---|---|---|---|---|---|---|---|---|
| CH₃ | I | OCH₂CF₃ | H | N | F | CH₃ | I | OCHF₂ | Et | N | F |
| CH₃ | I | OCH₂CF₃ | Me | N | F | CH₃ | I | OCHF₂ | i-Pr | N | F |
| CH₃ | I | OCH₂CF₃ | Et | N | F | CH₃ | I | OCHF₂ | t-Bu | N | F |
| CH₃ | I | OCH₂CF₃ | i-Pr | N | F | CH₃ | I | OCHF₂ | H | N | Cl |
| CH₃ | I | OCH₂CF₃ | t-Bu | N | F | CH₃ | I | OCHF₂ | Me | N | Cl |
| CH₃ | I | OCH₂CF₃ | H | N | Cl | CH₃ | I | OCHF₂ | Et | N | Cl |
| CH₃ | I | OCH₂CF₃ | Me | N | Cl | CH₃ | I | OCHF₂ | i-Pr | N | Cl |
| CH₃ | I | OCH₂CF₃ | Et | N | Cl | CH₃ | I | OCHF₂ | t-Bu | N | Cl |
| CH₃ | I | OCH₂CF₃ | i-Pr | N | Cl | CH₃ | I | OCHF₂ | H | N | Br |
| CH₃ | I | OCH₂CF₃ | t-Bu | N | Cl | CH₃ | I | OCHF₂ | Me | N | Br |
| CH₃ | I | OCH₂CF₃ | H | N | Br | CH₃ | I | OCHF₂ | Et | N | Br |
| CH₃ | I | OCH₂CF₃ | Me | N | Br | CH₃ | I | OCHF₂ | i-Pr | N | Br |
| CH₃ | I | OCH₂CF₃ | Et | N | Br | CH₃ | I | OCHF₂ | t-Bu | N | Br |
| CH₃ | I | OCH₂CF₃ | i-Pr | N | Br | CH₃ | CN | CF₃ | H | N | F |
| CH₃ | I | OCH₂CF₃ | t-Bu | N | Br | CH₃ | CN | CF₃ | Me | N | F |
| CH₃ | Cl | OCHF₂ | H | N | F | CH₃ | CN | CF₃ | Et | N | F |
| CH₃ | Cl | OCHF₂ | Me | N | F | CH₃ | CN | CF₃ | i-Pr | N | F |
| CH₃ | Cl | OCHF₂ | Et | N | F | CH₃ | CN | CF₃ | t-Bu | N | F |
| CH₃ | Cl | OCHF₂ | i-Pr | N | F | CH₃ | CN | CF₃ | H | N | Cl |
| CH₃ | Cl | OCHF₂ | t-Bu | N | F | CH₃ | CN | CF₃ | Me | N | Cl |
| CH₃ | Cl | OCHF₂ | H | N | Cl | CH₃ | CN | CF₃ | Et | N | Cl |
| CH₃ | Cl | OCHF₂ | Me | N | Cl | CH₃ | CN | CF₃ | i-Pr | N | Cl |
| CH₃ | Cl | OCHF₂ | Et | N | Cl | CH₃ | CN | CF₃ | t-Bu | N | Cl |
| CH₃ | Cl | OCHF₂ | i-Pr | N | Cl | CH₃ | CN | CF₃ | H | N | Br |
| CH₃ | Cl | OCHF₂ | t-Bu | N | Cl | CH₃ | CN | CF₃ | Me | N | Br |
| CH₃ | Cl | OCHF₂ | H | N | Br | CH₃ | CN | CF₃ | Et | N | Br |
| CH₃ | Cl | OCHF₂ | Me | N | Br | CH₃ | CN | CF₃ | i-Pr | N | Br |
| CH₃ | Cl | OCHF₂ | Et | N | Br | CH₃ | CN | CF₃ | t-Bu | N | Br |
| CH₃ | Cl | OCHF₂ | i-Pr | N | Br | CH₃ | CN | Cl | H | N | F |
| CH₃ | Cl | OCHF₂ | t-Bu | N | Br | CH₃ | CN | Cl | Me | N | F |
| CH₃ | Br | OCHF₂ | H | N | F | CH₃ | CN | Cl | Et | N | F |
| CH₃ | Br | OCHF₂ | Me | N | F | CH₃ | CN | Cl | i-Pr | N | F |
| CH₃ | Br | OCHF₂ | Et | N | F | CH₃ | CN | Cl | t-Bu | N | F |
| CH₃ | Br | OCHF₂ | i-Pr | N | F | CH₃ | CN | Cl | H | N | Cl |
| CH₃ | Br | OCHF₂ | t-Bu | N | F | CH₃ | CN | Cl | Me | N | Cl |
| CH₃ | Br | OCHF₂ | H | N | Cl | CH₃ | CN | Cl | Et | N | Cl |
| CH₃ | Br | OCHF₂ | Me | N | Cl | CH₃ | CN | Cl | i-Pr | N | Cl |
| CH₃ | Br | OCHF₂ | Et | N | Cl | CH₃ | CN | Cl | t-Bu | N | Cl |
| CH₃ | Br | OCHF₂ | i-Pr | N | Cl | CH₃ | CN | Cl | H | N | Br |
| CH₃ | Br | OCHF₂ | t-Bu | N | Cl | CH₃ | CN | Cl | Me | N | Br |
| CH₃ | Br | OCHF₂ | H | N | Br | CH₃ | CN | Cl | Et | N | Br |
| CH₃ | Br | OCHF₂ | Me | N | Br | CH₃ | CN | Cl | i-Pr | N | Br |
| CH₃ | Br | OCHF₂ | Et | N | Br | CH₃ | CN | Cl | t-Bu | N | Br |
| CH₃ | Br | OCHF₂ | i-Pr | N | Br | CH₃ | CN | Br | H | N | F |
| CH₃ | Br | OCHF₂ | t-Bu | N | Br | CH₃ | CN | Br | Me | N | F |
| CH₃ | I | OCHF₂ | H | N | F | CH₃ | CN | Br | Et | N | F |
| CH₃ | I | OCHF₂ | Me | N | F | CH₃ | CN | Br | i-Pr | N | F |

TABLE 2-continued

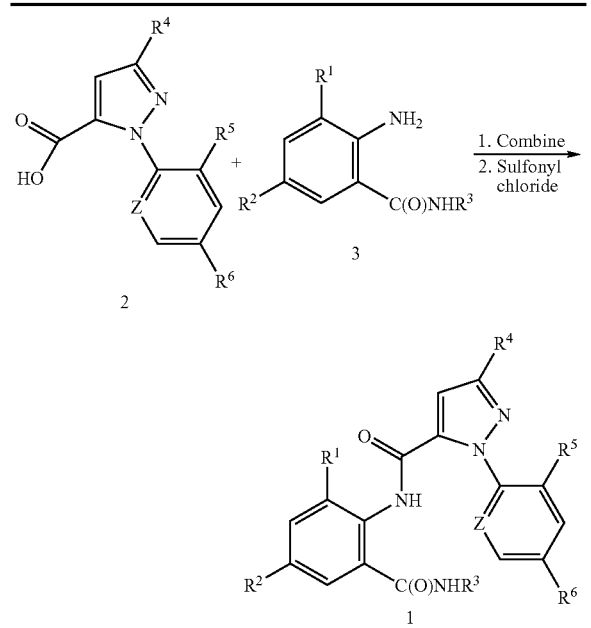

| R¹ | R² | R⁴ | R³ | Z | R⁵ |
|---|---|---|---|---|---|
| CH₃ | CN | Br | t-Bu | N | F |
| CH₃ | CN | Br | H | N | Cl |
| CH₃ | CN | Br | Me | N | Cl |
| CH₃ | CN | Br | Et | N | Cl |
| CH₃ | CN | Br | i-Pr | N | Cl |
| CH₃ | CN | Br | t-Bu | N | Cl |
| CH₃ | CN | Br | H | N | Br |
| CH₃ | CN | Br | Me | N | Br |
| CH₃ | CN | Br | Et | N | Br |
| CH₃ | CN | Br | i-Pr | N | Br |
| CH₃ | CN | Br | t-Bu | N | Br |
| CH₃ | CN | OCH₂CF₃ | H | N | F |
| CH₃ | CN | OCH₂CF₃ | Me | N | F |
| CH₃ | CN | OCH₂CF₃ | Et | N | F |
| CH₃ | CN | OCH₂CF₃ | i-Pr | N | F |
| CH₃ | CN | OCH₂CF₃ | t-BU | N | F |
| CH₃ | CN | OCH₂CF₃ | H | N | Cl |
| CH₃ | CN | OCH₂CF₃ | Me | N | Cl |
| CH₃ | CN | OCH₂CF₃ | Et | N | Cl |
| CH₃ | CN | OCH₂CF₃ | i-Pr | N | Cl |
| CH₃ | CN | OCH₂CF₃ | t-Bu | N | Cl |
| CH₃ | CN | OCH₂CF₃ | H | N | Br |
| CH₃ | CN | OCH₂CF₃ | Me | N | Br |
| CH₃ | CN | OCH₂CF₃ | Et | N | Br |
| CH₃ | CN | OCH₂CF₃ | i-Pr | N | Br |
| CH₃ | CN | OCH₂CF₃ | t-Bu | N | Br |
| CH₃ | CN | OCHF₂ | H | N | F |
| CH₃ | CN | OCHF₂ | Me | N | F |
| CH₃ | CN | OCHF₂ | Et | N | F |
| CH₃ | CN | OCHF₂ | i-Pr | N | F |
| CH₃ | CN | OCHF₂ | t-Bu | N | F |
| CH₃ | CN | OCHF₂ | H | N | Cl |
| CH₃ | CN | OCHF₂ | Me | N | Cl |
| CH₃ | CN | OCHF₂ | Et | N | Cl |
| CH₃ | CN | OCHF₂ | i-Pr | N | Cl |
| CH₃ | CN | OCHF₂ | t-Bu | N | Cl |
| CH₃ | CN | OCHF₂ | H | N | Br |
| CH₃ | CN | OCHF₂ | Me | N | Br |
| CH₃ | CN | OCHF₂ | Et | N | Br |
| CH₃ | CN | OCHF₂ | i-Pr | N | Br |
| CH₃ | CN | OCHF₂ | t-Bu | N | Br |
| CH₃ | Cl | CF₃ | H | CH | F |
| CH₃ | Cl | CF₃ | Me | CH | F |
| CH₃ | Cl | CF₃ | Et | CH | F |
| CH₃ | Cl | CF₃ | i-Pr | CH | F |
| CH₃ | Cl | CF₃ | t-Bu | CH | F |
| CH₃ | Cl | CF₃ | H | CH | Cl |

TABLE 2-continued

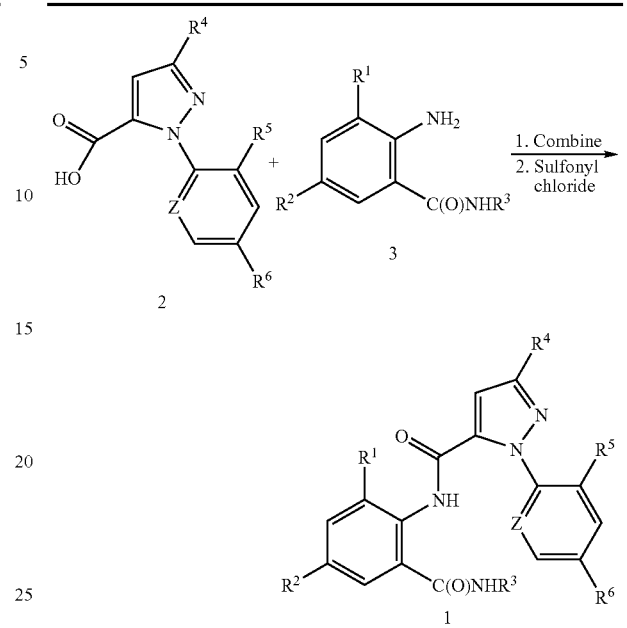

| R¹ | R² | R⁴ | R³ | Z | R⁵ |
|---|---|---|---|---|---|
| CH₃ | Cl | CF₃ | Me | CH | Cl |
| CH₃ | Cl | CF₃ | Et | CH | Cl |
| CH₃ | Cl | CF₃ | i-Pr | CH | Cl |
| CH₃ | Cl | CF₃ | t-Bu | CH | Cl |
| CH₃ | Cl | CF₃ | H | CH | Br |
| CH₃ | Cl | CF₃ | Me | CH | Br |
| CH₃ | Cl | CF₃ | Et | CH | Br |
| CH₃ | Cl | CF₃ | i-Pr | CH | Br |
| CH₃ | Cl | CF₃ | t-Bu | CH | Br |
| CH₃ | Cl | Cl | H | CH | F |
| CH₃ | Cl | Cl | Me | CH | F |
| CH₃ | Cl | Cl | Et | CH | F |
| CH₃ | Cl | Cl | i-Pr | CH | F |
| CH₃ | Cl | Cl | t-Bu | CH | F |
| CH₃ | Cl | Cl | H | CH | Cl |
| CH₃ | Cl | Cl | Me | CH | Cl |
| CH₃ | Cl | Cl | Et | CH | Cl |
| CH₃ | Cl | Cl | i-Pr | CH | Cl |
| CH₃ | Cl | Cl | t-Bu | CH | Cl |
| CH₃ | Cl | Cl | H | CH | Br |
| CH₃ | Cl | Cl | Me | CH | Br |
| CH₃ | Cl | Cl | Et | CH | Br |
| CH₃ | Cl | Cl | i-Pr | CH | Br |
| CH₃ | Cl | Cl | t-Bu | CH | Br |
| CH₃ | Cl | Br | H | CH | F |
| CH₃ | Cl | Br | Me | CH | F |
| CH₃ | Cl | Br | Et | CH | F |
| CH₃ | Cl | Br | i-Pr | CH | F |
| CH₃ | Cl | Br | t-Bu | CH | F |
| CH₃ | Cl | Br | H | CH | Cl |
| CH₃ | Cl | Br | Me | CH | Cl |
| CH₃ | Cl | Br | Et | CH | Cl |
| CH₃ | Cl | Br | i-Pr | CH | Cl |
| CH₃ | Cl | Br | t-Bu | CH | Cl |
| CH₃ | Cl | Br | H | CH | Br |
| CH₃ | Cl | Br | Me | CH | Br |
| CH₃ | Cl | Br | Et | CH | Br |
| CH₃ | Cl | Br | i-Pr | CH | Br |
| CH₃ | Cl | Br | t-Bu | CH | Br |
| CH₃ | Cl | OCH₂CF₃ | H | CH | F |
| CH₃ | Cl | OCH₂CF₃ | Me | CH | F |
| CH₃ | Cl | OCH₂CF₃ | Et | CH | F |
| CH₃ | Cl | OCH₂CF₃ | i-Pr | CH | F |
| CH₃ | Cl | OCH₂CF₃ | t-Bu | CH | F |
| CH₃ | Cl | OCH₂CF₃ | H | CH | Cl |
| CH₃ | Cl | OCH₂CF₃ | Me | CH | Cl |
| CH₃ | Cl | OCH₂CF₃ | Et | CH | Cl |

TABLE 2-continued

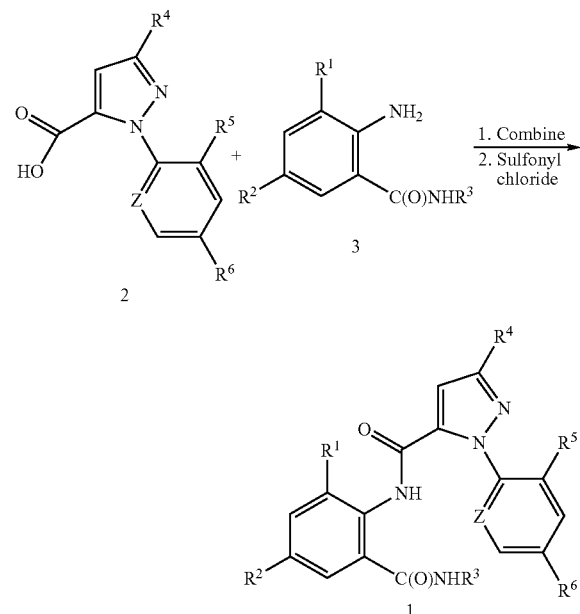

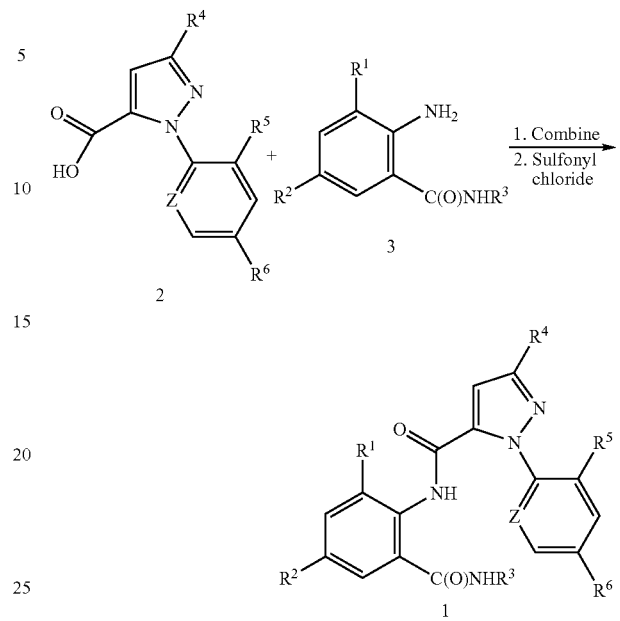

| R¹ | R² | R⁴ | R³ | Z | R⁵ |
|---|---|---|---|---|---|
| CH₃ | Cl | OCH₂CF₃ | i-Pr | CH | Cl |
| CH₃ | Cl | OCH₂CF₃ | t-Bu | CH | Cl |
| CH₃ | Cl | OCH₂CF₃ | H | CH | Br |
| CH₃ | Cl | OCH₂CF₃ | Me | CH | Br |
| CH₃ | Cl | OCH₂CF₃ | Et | CH | Br |
| CH₃ | Cl | OCH₂CF₃ | i-Pr | CH | Br |
| CH₃ | Cl | OCH₂CF₃ | t-Bu | CH | Br |
| CH₃ | Br | CF₃ | H | CH | F |
| CH₃ | Br | CF₃ | Me | CH | F |
| CH₃ | Br | CF₃ | Et | CH | F |
| CH₃ | Br | CF₃ | i-Pr | CH | F |
| CH₃ | Br | CF₃ | t-Bu | CH | F |
| CH₃ | Br | CF₃ | H | CH | Cl |
| CH₃ | Br | CF₃ | Me | CH | Cl |
| CH₃ | Br | CF₃ | Et | CH | Cl |
| CH₃ | Br | CF₃ | i-Pr | CH | Cl |
| CH₃ | Br | CF₃ | t-Bu | CH | Cl |
| CH₃ | Br | CF₃ | H | CH | Br |
| CH₃ | Br | CF₃ | Me | CH | Br |
| CH₃ | Br | CF₃ | Et | CH | Br |
| CH₃ | Br | CF₃ | i-Pr | CH | Br |
| CH₃ | Br | CF₃ | t-Bu | CH | Br |
| CH₃ | Br | Cl | H | CH | F |
| CH₃ | Br | Cl | Me | CH | F |
| CH₃ | Br | Cl | Et | CH | F |
| CH₃ | Br | Cl | i-Pr | CH | F |
| CH₃ | Br | Cl | t-Bu | CH | F |
| CH₃ | Br | Cl | H | CH | Cl |
| CH₃ | Br | Cl | Me | CH | Cl |
| CH₃ | Br | Cl | Et | CH | Cl |
| CH₃ | Br | Cl | i-Pr | CH | Cl |
| CH₃ | Br | Cl | t-Bu | CH | Cl |
| CH₃ | Br | Cl | H | CH | Br |
| CH₃ | Br | Cl | Me | CH | Br |
| CH₃ | Br | Cl | Et | CH | Br |
| CH₃ | Br | Cl | i-Pr | CH | Br |
| CH₃ | Br | Cl | t-Bu | CH | Br |
| CH₃ | Br | Br | H | CH | F |
| CH₃ | Br | Br | Me | CH | F |
| CH₃ | Br | Br | Et | CH | F |
| CH₃ | Br | Br | i-Pr | CH | F |
| CH₃ | Br | Br | t-Bu | CH | F |
| CH₃ | Br | Br | H | CH | Cl |
| CH₃ | Br | Br | Me | CH | Cl |
| CH₃ | Br | Br | Et | CH | Cl |
| CH₃ | Br | Br | i-Pr | CH | Cl |
| CH₃ | Br | Br | t-Bu | CH | Cl |
| CH₃ | Br | Br | H | CH | Br |
| CH₃ | Br | Br | Me | CH | Br |
| CH₃ | Br | Br | Et | CH | Br |
| CH₃ | Br | Br | i-Pr | CH | Br |
| CH₃ | Br | Br | t-Bu | CH | Br |
| CH₃ | Br | OCH₂CF₃ | H | CH | F |
| CH₃ | Br | OCH₂CF₃ | Me | CH | F |
| CH₃ | Br | OCH₂CF₃ | Et | CH | F |
| CH₃ | Br | OCH₂CF₃ | i-Pr | CH | F |
| CH₃ | Br | OCH₂CF₃ | t-Bu | CH | F |
| CH₃ | Br | OCH₂CF₃ | H | CH | Cl |
| CH₃ | Br | OCH₂CF₃ | Me | CH | Cl |
| CH₃ | Br | OCH₂CF₃ | Et | CH | Cl |
| CH₃ | Br | OCH₂CF₃ | i-Pr | CH | Cl |
| CH₃ | Br | OCH₂CF₃ | t-Bu | CH | Cl |
| CH₃ | Br | OCH₂CF₃ | H | CH | Br |
| CH₃ | Br | OCH₂CF₃ | Me | CH | Br |
| CH₃ | Br | OCH₂CF₃ | Et | CH | Br |
| CH₃ | Br | OCH₂CF₃ | i-Pr | CH | Br |
| CH₃ | Br | OCH₂CF₃ | t-Bu | CH | Br |
| CH₃ | I | CF₃ | H | CH | F |
| CH₃ | I | CF₃ | Me | CH | F |
| CH₃ | I | CF₃ | Et | CH | F |
| CH₃ | I | CF₃ | i-Pr | CH | F |
| CH₃ | I | CF₃ | t-Bu | CH | F |
| CH₃ | I | CF₃ | H | CH | Cl |
| CH₃ | I | CF₃ | Me | CH | Cl |
| CH₃ | I | CF₃ | Et | CH | Cl |
| CH₃ | I | CF₃ | i-Pr | CH | Cl |
| CH₃ | I | CF₃ | t-Bu | CH | Cl |
| CH₃ | I | CF₃ | H | CH | Br |
| CH₃ | I | CF₃ | Me | CH | Br |
| CH₃ | I | CF₃ | Et | CH | Br |
| CH₃ | I | CF₃ | i-Pr | CH | Br |
| CH₃ | I | CF₃ | t-Bu | CH | Br |
| CH₃ | I | Cl | H | CH | F |
| CH₃ | I | Cl | Me | CH | F |
| CH₃ | I | Cl | Et | CH | F |
| CH₃ | I | Cl | i-Pr | CH | F |
| CH₃ | I | Cl | t-Bu | CH | F |
| CH₃ | I | Cl | H | CH | Cl |
| CH₃ | I | Cl | Me | CH | Cl |
| CH₃ | I | Cl | Et | CH | Cl |
| CH₃ | I | Cl | i-Pr | CH | Cl |
| CH₃ | I | Cl | t-Bu | CH | Cl |
| CH₃ | I | Cl | H | CH | Br |
| CH₃ | I | Cl | Me | CH | Br |

TABLE 2-continued

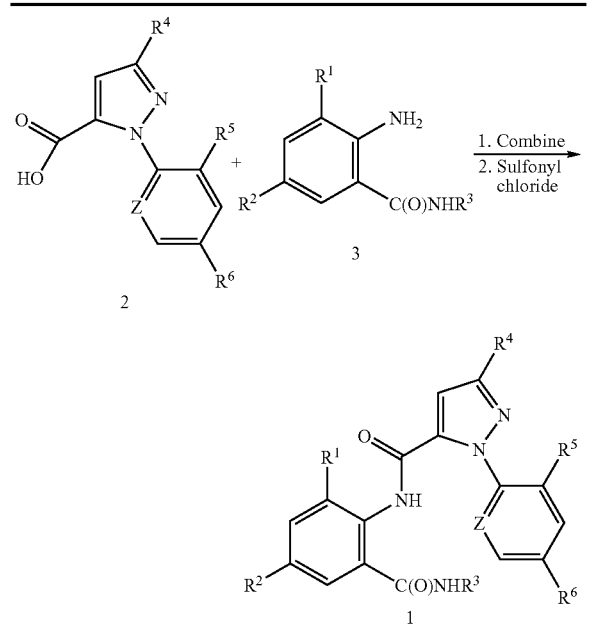

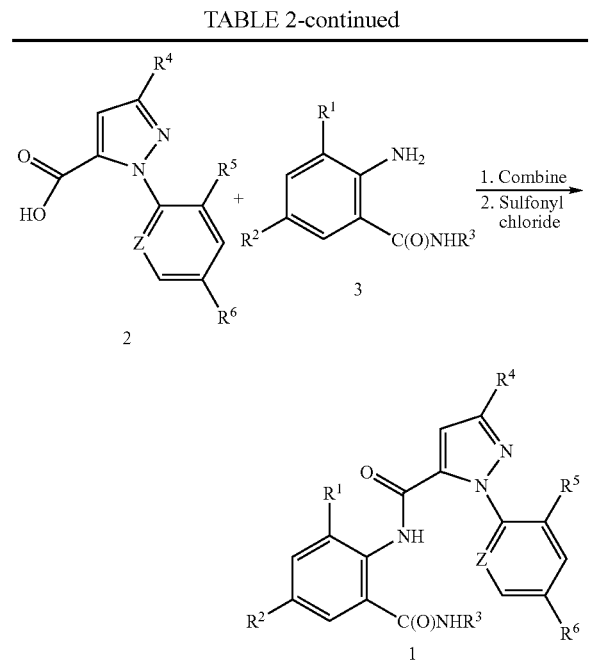

| R¹ | R² | R⁴ | R³ | Z | R⁵ | R¹ | R² | R⁴ | R³ | Z | R⁵ |
|---|---|---|---|---|---|---|---|---|---|---|---|
| CH₃ | I | Cl | Et | CH | Br | CH₃ | Cl | OCHF₂ | t-Bu | CH | Br |
| CH₃ | I | Cl | i-Pr | CH | Br | CH₃ | Br | OCHF₂ | H | CH | F |
| CH₃ | I | Cl | t-Bu | CH | Br | CH₃ | Br | OCHF₂ | Me | CH | F |
| CH₃ | I | Br | H | CH | F | CH₃ | Br | OCHF₂ | Et | CH | F |
| CH₃ | I | Br | Me | CH | F | CH₃ | Br | OCHF₂ | i-Pr | CH | F |
| CH₃ | I | Br | Et | CH | F | CH₃ | Br | OCHF₂ | t-Bu | CH | F |
| CH₃ | I | Br | i-Pr | CH | F | CH₃ | Br | OCHF₂ | H | CH | Cl |
| CH₃ | I | Br | t-Bu | CH | F | CH₃ | Br | OCHF₂ | Me | CH | Cl |
| CH₃ | I | Br | H | CH | Cl | CH₃ | Br | OCHF₂ | Et | CH | Cl |
| CH₃ | I | Br | Me | CH | Cl | CH₃ | Br | OCHF₂ | i-Pr | CH | Cl |
| CH₃ | I | Br | Et | CH | Cl | CH₃ | Br | OCHF₂ | t-Bu | CH | Cl |
| CH₃ | I | Br | i-Pr | CH | Cl | CH₃ | Br | OCHF₂ | H | CH | Br |
| CH₃ | I | Br | t-Bu | CH | Cl | CH₃ | Br | OCHF₂ | Me | CH | Br |
| CH₃ | I | Br | H | CH | Br | CH₃ | Br | OCHF₂ | Et | CH | Br |
| CH₃ | I | Br | Me | CH | Br | CH₃ | Br | OCHF₂ | i-Pr | CH | Br |
| CH₃ | I | Br | Et | CH | Br | CH₃ | Br | OCHF₂ | t-Bu | CH | Br |
| CH₃ | I | Br | i-Pr | CH | Br | CH₃ | I | OCHF₂ | H | CH | F |
| CH₃ | I | Br | t-Bu | CH | Br | CH₃ | I | OCHF₂ | Me | CH | F |
| CH₃ | I | OCH₂CF₃ | H | CH | F | CH₃ | I | OCHF₂ | Et | CH | F |
| CH₃ | I | OCH₂CF₃ | Me | CH | F | CH₃ | I | OCHF₂ | i-Pr | CH | F |
| CH₃ | I | OCH₂CF₃ | Et | CH | F | CH₃ | I | OCHF₂ | t-Bu | CH | F |
| CH₃ | I | OCH₂CF₃ | i-Pr | CH | F | CH₃ | I | OCHF₂ | H | CH | Cl |
| CH₃ | I | OCH₂CF₃ | t-Bu | CH | F | CH₃ | I | OCHF₂ | Me | CH | Cl |
| CH₃ | I | OCH₂CF₃ | H | CH | Cl | CH₃ | I | OCHF₂ | Et | CH | Cl |
| CH₃ | I | OCH₂CF₃ | Me | CH | Cl | CH₃ | I | OCHF₂ | i-Pr | CH | Cl |
| CH₃ | I | OCH₂CF₃ | Et | CH | Cl | CH₃ | I | OCHF₂ | t-Bu | CH | Cl |
| CH₃ | I | OCH₂CF₃ | i-Pr | CH | Cl | CH₃ | I | OCHF₂ | H | CH | Br |
| CH₃ | I | OCH₂CF₃ | t-Bu | CH | Cl | CH₃ | I | OCHF₂ | Me | CH | Br |
| CH₃ | I | OCH₂CF₃ | H | CH | Br | CH₃ | I | OCHF₂ | Et | CH | Br |
| CH₃ | I | OCH₂CF₃ | Me | CH | Br | CH₃ | I | OCHF₂ | i-Pr | CH | Br |
| CH₃ | I | OCH₂CF₃ | Et | CH | Br | CH₃ | I | OCHF₂ | t-Bu | CH | Br |
| CH₃ | I | OCH₂CF₃ | i-Pr | CH | Br | CH₃ | CN | CF₃ | H | CH | F |
| CH₃ | I | OCH₂CF₃ | t-Bu | CH | Br | CH₃ | CN | CF₃ | Me | CH | F |
| CH₃ | Cl | OCHF₂ | H | CH | F | CH₃ | CN | CF₃ | Et | CH | F |
| CH₃ | Cl | OCHF₂ | Me | CH | F | CH₃ | CN | CF₃ | i-Pr | CH | F |
| CH₃ | Cl | OCHF₂ | Et | CH | F | CH₃ | CN | CF₃ | t-Bu | CH | F |
| CH₃ | Cl | OCHF₂ | i-Pr | CH | F | CH₃ | CN | CF₃ | H | CH | Cl |
| CH₃ | Cl | OCHF₂ | t-Bu | CH | F | CH₃ | CN | CF₃ | Me | CH | Cl |
| CH₃ | Cl | OCHF₂ | H | CH | Cl | CH₃ | CN | CF₃ | Et | CH | Cl |
| CH₃ | Cl | OCHF₂ | Me | CH | Cl | CH₃ | CN | CF₃ | i-Pr | CH | Cl |
| CH₃ | Cl | OCHF₂ | Et | CH | Cl | CH₃ | CN | CF₃ | t-Bu | CH | Cl |
| CH₃ | Cl | OCHF₂ | i-Pr | CH | Cl | CH₃ | CN | CF₃ | H | CH | Br |
| CH₃ | Cl | OCHF₂ | t-Bu | CH | Cl | CH₃ | CN | CF₃ | Me | CH | Br |
| CH₃ | Cl | OCHF₂ | H | CH | Br | CH₃ | CN | CF₃ | Et | CH | Br |
| CH₃ | Cl | OCHF₂ | Me | CH | Br | CH₃ | CN | CF₃ | i-Pr | CH | Br |
| CH₃ | Cl | OCHF₂ | Et | CH | Br | CH₃ | CN | CF₃ | t-Bu | CH | Br |
| CH₃ | Cl | OCHF₂ | i-Pr | CH | Br | CH₃ | CN | Cl | H | CH | F |

TABLE 2-continued

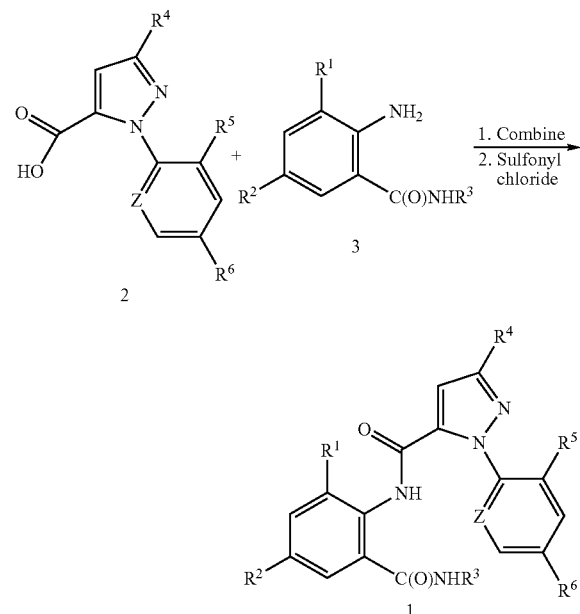
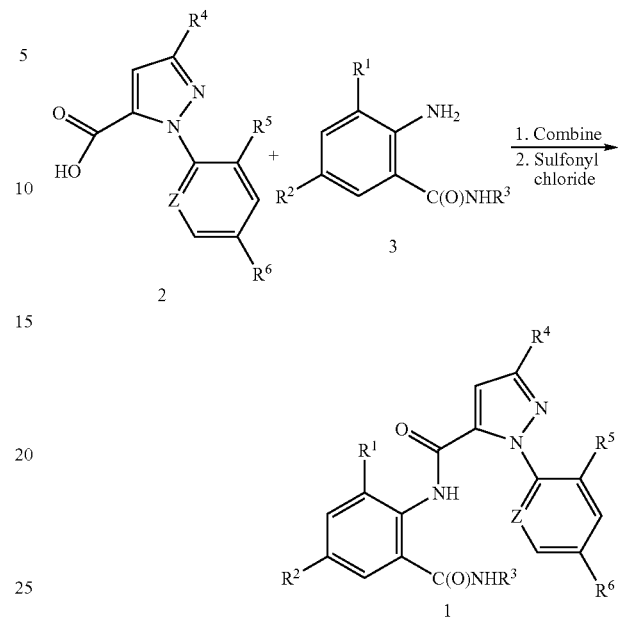

| R¹ | R² | R⁴ | R³ | Z | R⁵ | R¹ | R² | R⁴ | R³ | Z | R⁵ |
|---|---|---|---|---|---|---|---|---|---|---|---|
| CH₃ | CN | Cl | Me | CH | F | CH₃ | CN | OCHF₂ | i-Pr | CH | F |
| CH₃ | CN | Cl | Et | CH | F | CH₃ | CN | OCHF₂ | t-Bu | CH | F |
| CH₃ | CN | Cl | i-Pr | CH | F | CH₃ | CN | OCHF₂ | H | CH | Cl |
| CH₃ | CN | Cl | t-Bu | CH | F | CH₃ | CN | OCHF₂ | Me | CH | Cl |
| CH₃ | CN | Cl | H | CH | Cl | CH₃ | CN | OCHF₂ | Et | CH | Cl |
| CH₃ | CN | Cl | Me | CH | Cl | CH₃ | CN | OCHF₂ | i-Pr | CH | Cl |
| CH₃ | CN | Cl | Et | CH | Cl | CH₃ | CN | OCHF₂ | t-Bu | CH | Cl |
| CH₃ | CN | Cl | i-Pr | CH | Cl | CH₃ | CN | OCHF₂ | H | CH | Br |
| CH₃ | CN | Cl | t-Bu | CH | Cl | CH₃ | CN | OCHF₂ | Me | CH | Br |
| CH₃ | CN | Cl | H | CH | Br | CH₃ | CN | OCHF₂ | Et | CH | Br |
| CH₃ | CN | Cl | Me | CH | Br | CH₃ | CN | OCHF₂ | i-Pr | CH | Br |
| CH₃ | CN | Cl | Et | CH | Br | CH₃ | CN | OCHF₂ | t-Bu | CH | Br |
| CH₃ | CN | Cl | i-Pr | CH | Br | Cl | Cl | CF₃ | H | N | F |
| CH₃ | CN | Cl | t-Bu | CH | Br | Cl | Cl | CF₃ | Me | N | F |
| CH₃ | CN | Br | H | CH | F | Cl | Cl | CF₃ | Et | N | F |
| CH₃ | CN | Br | Me | CH | F | Cl | Cl | CF₃ | i-Pr | N | F |
| CH₃ | CN | Br | Et | CH | F | Cl | Cl | CF₃ | t-Bu | N | F |
| CH₃ | CN | Br | i-Pr | CH | F | Cl | Cl | CF₃ | H | N | Cl |
| CH₃ | CN | Br | t-Bu | CH | F | Cl | Cl | CF₃ | Me | N | Cl |
| CH₃ | CN | Br | H | CH | Cl | Cl | Cl | CF₃ | Et | N | Cl |
| CH₃ | CN | Br | Me | CH | Cl | Cl | Cl | CF₃ | i-Pr | N | Cl |
| CH₃ | CN | Br | Et | CH | Cl | Cl | Cl | CF₃ | t-Bu | N | Cl |
| CH₃ | CN | Br | i-Pr | CH | Cl | Cl | Cl | CF₃ | H | N | Br |
| CH₃ | CN | Br | t-Bu | CH | Cl | Cl | Cl | CF₃ | Me | N | Br |
| CH₃ | CN | Br | H | CH | Br | Cl | Cl | CF₃ | Et | N | Br |
| CH₃ | CN | Br | Me | CH | Br | Cl | Cl | CF₃ | i-Pr | N | Br |
| CH₃ | CN | Br | Et | CH | Br | Cl | Cl | CF₃ | t-Bu | N | Br |
| CH₃ | CN | Br | i-Pr | CH | Br | Cl | Cl | Cl | H | N | F |
| CH₃ | CN | Br | t-Bu | CH | Br | Cl | Cl | Cl | Me | N | F |
| CH₃ | CN | OCH₂CF₃ | H | CH | F | Cl | Cl | Cl | Et | N | F |
| CH₃ | CN | OCH₂CF₃ | Me | CH | F | Cl | Cl | Cl | i-Pr | N | F |
| CH₃ | CN | OCH₂CF₃ | Et | CH | F | Cl | Cl | Cl | t-Bu | N | F |
| CH₃ | CN | OCH₂CF₃ | i-Pr | CH | F | Cl | Cl | Cl | H | N | Cl |
| CH₃ | CN | OCH₂CF₃ | t-Bu | CH | F | Cl | Cl | Cl | Me | N | Cl |
| CH₃ | CN | OCH₂CF₃ | H | CH | Cl | Cl | Cl | Cl | Et | N | Cl |
| CH₃ | CN | OCH₂CF₃ | Me | CH | Cl | Cl | Cl | Cl | i-Pr | N | Cl |
| CH₃ | CN | OCH₂CF₃ | Et | CH | Cl | Cl | Cl | Cl | t-Bu | N | Cl |
| CH₃ | CN | OCH₂CF₃ | i-Pr | CH | Cl | Cl | Cl | Cl | H | N | Br |
| CH₃ | CN | OCH₂CF₃ | t-Bu | CH | Cl | Cl | Cl | Cl | Me | N | Br |
| CH₃ | CN | OCH₂CF₃ | H | CH | Br | Cl | Cl | Cl | Et | N | Br |
| CH₃ | CN | OCH₂CF₃ | Me | CH | Br | Cl | Cl | Cl | i-Pr | N | Br |
| CH₃ | CN | OCH₂CF₃ | Et | CH | Br | Cl | Cl | Cl | t-Bu | N | Br |
| CH₃ | CN | OCH₂CF₃ | i-Pr | CH | Br | Cl | Cl | Br | H | N | F |
| CH₃ | CN | OCH₂CF₃ | t-Bu | CH | Br | Cl | Cl | Br | Me | N | F |
| CH₃ | CN | OCHF₂ | H | CH | F | Cl | Cl | Br | Et | N | F |
| CH₃ | CN | OCHF₂ | Me | CH | F | Cl | Cl | Br | i-Pr | N | F |
| CH₃ | CN | OCHF₂ | Et | CH | F | Cl | Cl | Br | t-Bu | N | F |

TABLE 2-continued

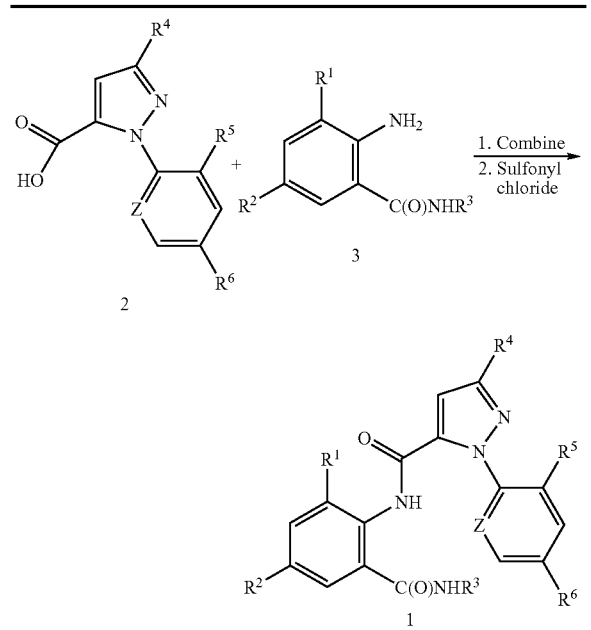

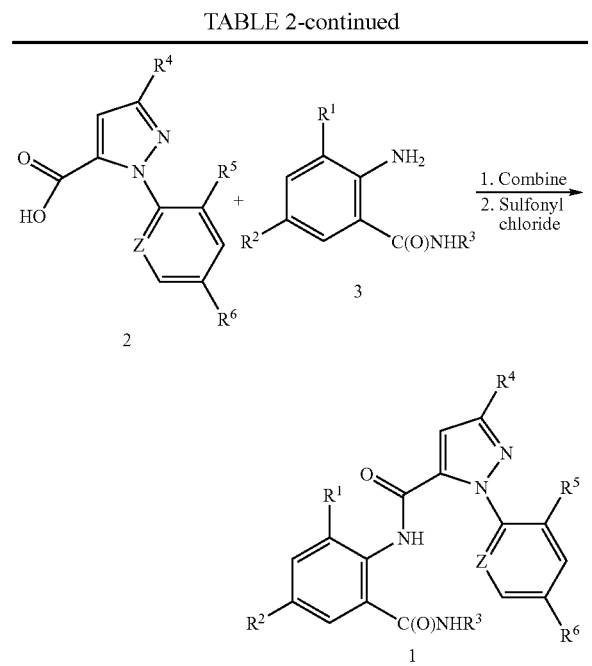

| R¹ | R² | R⁴ | R³ | Z | R⁵ | R¹ | R² | R⁴ | R³ | Z | R⁵ |
|----|----|----|----|---|----|----|----|----|----|---|----|
| Cl | Cl | Br | H | N | Cl | Cl | Br | Cl | Et | N | Cl |
| Cl | Cl | Br | Me | N | Cl | Cl | Br | Cl | i-Pr | N | Cl |
| Cl | Cl | Br | Et | N | Cl | Cl | Br | Cl | t-Bu | N | Cl |
| Cl | Cl | Br | i-Pr | N | Cl | Cl | Br | Cl | H | N | Br |
| Cl | Cl | Br | t-Bu | N | Cl | Cl | Br | Cl | Me | N | Br |
| Cl | Cl | Br | H | N | Br | Cl | Br | Cl | Et | N | Br |
| Cl | Cl | Br | Me | N | Br | Cl | Br | Cl | i-Pr | N | Br |
| Cl | Cl | Br | Et | N | Br | Cl | Br | Cl | t-Bu | N | Br |
| Cl | Cl | Br | i-Pr | N | Br | Cl | Br | Br | H | N | F |
| Cl | Cl | Br | t-Bu | N | Br | Cl | Br | Br | Me | N | F |
| Cl | Cl | OCH₂CF₃ | H | N | F | Cl | Br | Br | Et | N | F |
| Cl | Cl | OCH₂CF₃ | Me | N | F | Cl | Br | Br | i-Pr | N | F |
| Cl | Cl | OCH₂CF₃ | Et | N | F | Cl | Br | Br | t-Bu | N | F |
| Cl | Cl | OCH₂CF₃ | i-Pr | N | F | Cl | Br | Br | H | N | Cl |
| Cl | Cl | OCH₂CF₃ | t-Bu | N | F | Cl | Br | Br | Me | N | Cl |
| Cl | Cl | OCH₂CF₃ | H | N | Cl | Cl | Br | Br | Et | N | Cl |
| Cl | Cl | OCH₂CF₃ | Me | N | Cl | Cl | Br | Br | i-Pr | N | Cl |
| Cl | Cl | OCH₂CF₃ | Et | N | Cl | Cl | Br | Br | t-Bu | N | CJ |
| Cl | Cl | OCH₂CF₃ | i-Pr | N | Cl | Cl | Br | Br | H | N | Br |
| Cl | Cl | OCH₂CF₃ | t-Bu | N | Cl | Cl | Br | Br | Me | N | Br |
| Cl | Cl | OCH₂CF₃ | H | N | Br | Cl | Br | Br | Et | N | Br |
| Cl | Cl | OCH₂CF₃ | Me | N | Br | Cl | Br | Br | i-Pr | N | Br |
| Cl | Cl | OCH₂CF₃ | Et | N | Br | Cl | Br | Br | t-Bu | N | Br |
| Cl | Cl | OCH₂CF₃ | i-Pr | N | Br | Cl | Br | OCH₂CF₃ | H | N | F |
| Cl | Cl | OCH₂CF₃ | t-Bu | N | Br | Cl | Br | OCH₂CF₃ | Me | N | F |
| Cl | Br | CF₃ | H | N | F | Cl | Br | OCH₂CF₃ | Et | N | F |
| Cl | Br | CF₃ | Me | N | F | Cl | Br | OCH₂CF₃ | i-Pr | N | F |
| Cl | Br | CF₃ | Et | N | F | Cl | Br | OCH₂CF₃ | t-Bu | N | F |
| Cl | Br | CF₃ | i-Pr | N | F | Cl | Br | OCH₂CF₃ | H | N | Cl |
| Cl | Br | CF₃ | t-Bu | N | F | Cl | Br | OCH₂CF₃ | Me | N | Cl |
| Cl | Br | CF₃ | H | N | Cl | Cl | Br | OCH₂CF₃ | Et | N | Cl |
| Cl | Br | CF₃ | Me | N | Cl | Cl | Br | OCH₂CF₃ | i-Pr | N | Cl |
| Cl | Br | CF₃ | Et | N | Cl | Cl | Br | OCH₂CF₃ | t-Bu | N | Cl |
| Cl | Br | CF₃ | i-Pr | N | Cl | Cl | Br | OCH₂CF₃ | H | N | Br |
| Cl | Br | CF₃ | t-Bu | N | Cl | Cl | Br | OCH₂CF₃ | Me | N | Br |
| Cl | Br | CF₃ | H | N | Br | Cl | Br | OCH₂CF₃ | Et | N | Br |
| Cl | Br | CF₃ | Me | N | Br | Cl | Br | OCH₂CF₃ | i-Pr | N | Br |
| Cl | Br | CF₃ | Et | N | Br | Cl | Br | OCH₂CF₃ | t-Bu | N | Br |
| Cl | Br | CF₃ | i-Pr | N | Br | Cl | I | CF₃ | H | N | F |
| Cl | Br | CF₃ | t-Bu | N | Br | Cl | I | CF₃ | Me | N | F |
| Cl | Br | Cl | H | N | F | Cl | I | CF₃ | Et | N | F |
| Cl | Br | Cl | Me | N | F | Cl | I | CF₃ | i-Pr | N | F |
| Cl | Br | Cl | Et | N | F | Cl | I | CF₃ | t-Bu | N | F |
| Cl | Br | Cl | i-Pr | N | F | Cl | I | CF₃ | H | N | Cl |
| Cl | Br | Cl | t-Bu | N | F | Cl | I | CF₃ | Me | N | Cl |
| Cl | Br | Cl | H | N | Cl | Cl | I | CF₃ | Et | N | Cl |
| Cl | Br | Cl | Me | N | Cl | Cl | I | CF₃ | i-Pr | N | Cl |

TABLE 2-continued

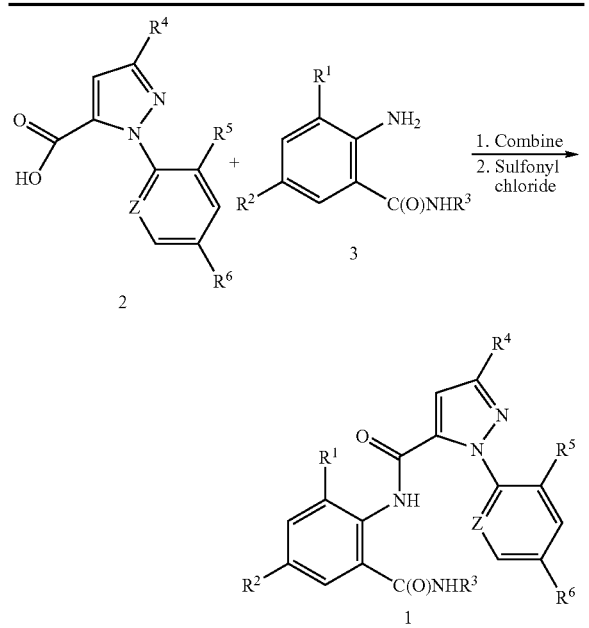

TABLE 2-continued

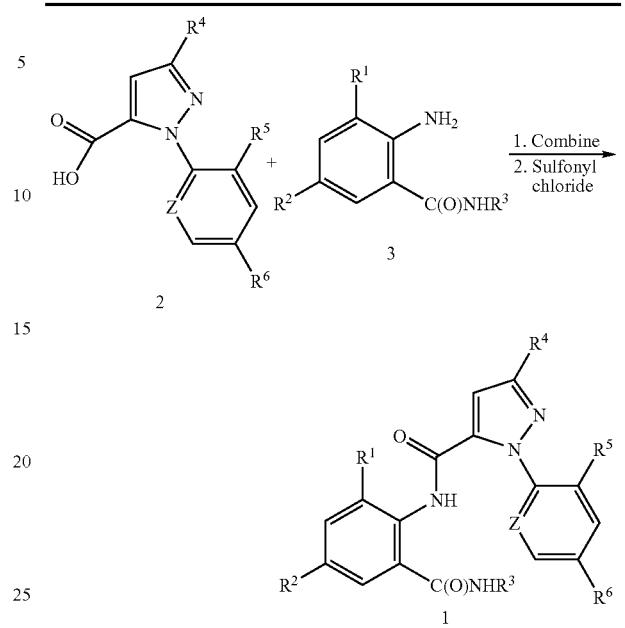

| R¹ | R² | R⁴ | R³ | Z | R⁵ | R¹ | R² | R⁴ | R³ | Z | R⁵ |
|---|---|---|---|---|---|---|---|---|---|---|---|
| Cl | I | CF₃ | t-Bu | N | Cl | Cl | I | OCH₂CF₃ | Me | N | Br |
| Cl | I | CF₃ | H | N | Br | Cl | I | OCH₂CF₃ | Et | N | Br |
| Cl | I | CF₃ | Me | N | Br | Cl | I | OCH₂CF₃ | i-Pr | N | Br |
| Cl | I | CF₃ | Et | N | Br | Cl | I | OCH₂CF₃ | t-Bu | N | Br |
| Cl | I | CF₃ | i-Pr | N | Br | Cl | Cl | OCHF₂ | H | N | F |
| Cl | I | CF₃ | t-Bu | N | Br | Cl | Cl | OCHF₂ | Me | N | F |
| Cl | I | Cl | H | N | F | Cl | Cl | OCHF₂ | Et | N | F |
| Cl | I | Cl | Me | N | F | Cl | Cl | OCHF₂ | i-Pr | N | F |
| Cl | I | Cl | Et | N | F | Cl | Cl | OCHF₂ | t-Bu | N | F |
| Cl | I | Cl | i-Pr | N | F | Cl | Cl | OCHF₂ | H | N | Cl |
| Cl | I | Cl | t-Bu | N | F | Cl | Cl | OCHF₂ | Me | N | Cl |
| Cl | I | Cl | H | N | Cl | Cl | Cl | OCHF₂ | Et | N | Cl |
| Cl | I | Cl | Me | N | Cl | Cl | Cl | OCHF₂ | i-Pr | N | Cl |
| Cl | I | Cl | Et | N | Cl | Cl | Cl | OCHF₂ | t-Bu | N | Cl |
| Cl | I | Cl | i-Pr | N | Cl | Cl | Cl | OCHF₂ | H | N | Br |
| Cl | I | Cl | t-Bu | N | Cl | Cl | Cl | OCHF₂ | Me | N | Br |
| Cl | I | Cl | H | N | Br | Cl | Cl | OCHF₂ | Et | N | Br |
| Cl | I | Cl | Me | N | Br | Cl | Cl | OCHF₂ | i-Pr | N | Br |
| Cl | I | Cl | Et | N | Br | Cl | Cl | OCHF₂ | t-Bu | N | Br |
| Cl | I | Cl | i-Pr | N | Br | Cl | Br | OCHF₂ | H | N | F |
| Cl | I | Cl | t-Bu | N | Br | Cl | Br | OCHF₂ | Me | N | F |
| Cl | I | Br | H | N | F | Cl | Br | OCHF₂ | Et | N | F |
| Cl | I | Br | Me | N | F | Cl | Br | OCHF₂ | i-Pr | N | F |
| Cl | I | Br | Et | N | F | Cl | Br | OCHF₂ | t-Bu | N | F |
| Cl | I | Br | i-Pr | N | F | Cl | Br | OCHF₂ | H | N | Cl |
| Cl | I | Br | t-Bu | N | F | Cl | Br | OCHF₂ | Me | N | Cl |
| Cl | I | Br | H | N | Cl | Cl | Br | OCHF₂ | Et | N | Cl |
| Cl | I | Br | Me | N | Cl | Cl | Br | OCHF₂ | i-Pr | N | Cl |
| Cl | I | Br | Et | N | Cl | Cl | Br | OCHF₂ | t-Bu | N | Cl |
| Cl | I | Br | i-Pr | N | Cl | Cl | Br | OCHF₂ | H | N | Br |
| Cl | I | Br | t-Bu | N | Cl | Cl | Br | OCHF₂ | Me | N | Br |
| Cl | I | Br | H | N | Br | Cl | Br | OCHF₂ | Et | N | Br |
| Cl | I | Br | Me | N | Br | Cl | Br | OCHF₂ | i-Pr | N | Br |
| Cl | I | Br | Et | N | Br | Cl | Br | OCHF₂ | t-Bu | N | Br |
| Cl | I | Br | i-Pr | N | Br | Cl | I | OCHF₂ | H | N | F |
| Cl | I | Br | t-Bu | N | Br | Cl | I | OCHF₂ | Me | N | F |
| Cl | I | OCH₂CF₃ | H | N | F | Cl | I | OCHF₂ | Et | N | F |
| Cl | I | OCH₂CF₃ | Me | N | F | Cl | I | OCHF₂ | i-Pr | N | F |
| Cl | I | OCH₂CF₃ | Et | N | F | Cl | I | OCHF₂ | t-Bu | N | F |
| Cl | I | OCH₂CF₃ | i-Pr | N | F | Cl | I | OCHF₂ | H | N | Cl |
| Cl | I | OCH₂CF₃ | t-Bu | N | F | Cl | I | OCHF₂ | Me | N | Cl |
| Cl | I | OCH₂CF₃ | H | N | Cl | Cl | I | OCHF₂ | Et | N | Cl |
| Cl | I | OCH₂CF₃ | Me | N | Cl | Cl | I | OCHF₂ | i-Pr | N | Cl |
| Cl | I | OCH₂CF₃ | Et | N | Cl | Cl | I | OCHF₂ | t-Bu | N | Cl |
| Cl | I | OCH₂CF₃ | i-Pr | N | Cl | Cl | I | OCHF₂ | H | N | Br |
| Cl | I | OCH₂CF₃ | t-Bu | N | Cl | Cl | I OCHF₂ | Me | N | Br |
| Cl | I | OCH₂CF₃ | H | N | Br | Cl | I | OCHF₂ | Et | N | Br |

TABLE 2-continued

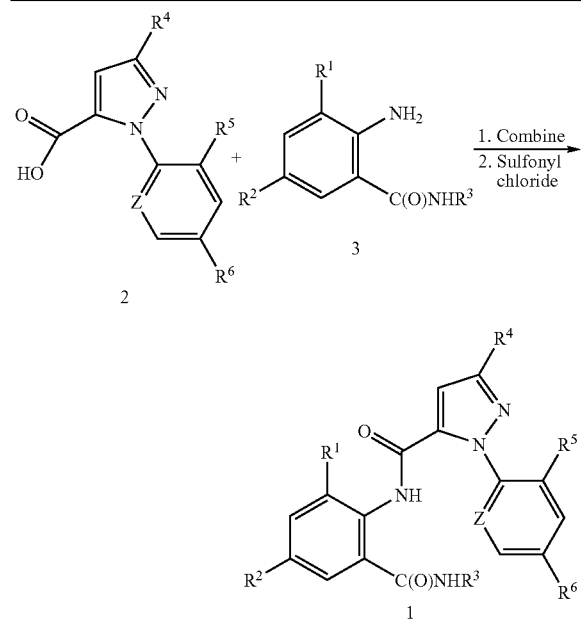

| R¹ | R² | R⁴ | R³ | Z | R⁵ |
|---|---|---|---|---|---|
| Cl | I | OCHF₂ | i-Pr | N | Br |
| Cl | I | OCHF₂ | t-Bu | N | Br |
| Cl | CN | CF₃ | H | N | F |
| Cl | CN | CF₃ | Me | N | F |
| Cl | CN | CF₃ | Et | N | F |
| Cl | CN | CF₃ | i-Pr | N | F |
| Cl | CN | CF₃ | t-Bu | N | F |
| Cl | CN | CF₃ | H | N | Cl |
| Cl | CN | CF₃ | Me | N | Cl |
| Cl | CN | CF₃ | Et | N | Cl |
| Cl | CN | CF₃ | i-Pr | N | Cl |
| Cl | CN | CF₃ | t-Bu | N | Cl |
| Cl | CN | CF₃ | H | N | Br |
| Cl | CN | CF₃ | Me | N | Br |
| Cl | CN | CF₃ | Et | N | Br |
| Cl | CN | CF₃ | i-Pr | N | Br |
| Cl | CN | CF₃ | t-Bu | N | Br |
| Cl | CN | Cl | H | N | F |
| Cl | CN | Cl | Me | N | F |
| Cl | CN | Cl | Et | N | F |
| Cl | CN | Cl | i-Pr | N | F |
| Cl | CN | Cl | t-Bu | N | F |
| Cl | CN | Cl | H | N | Cl |
| Cl | CN | Cl | Me | N | Cl |
| Cl | CN | Cl | Et | N | Cl |
| Cl | CN | Cl | i-Pr | N | Cl |
| Cl | CN | Cl | t-Bu | N | Cl |
| Cl | CN | Cl | H | N | Br |
| Cl | CN | Cl | Me | N | Br |
| Cl | CN | Cl | Et | N | Br |
| Cl | CN | Cl | i-Pr | N | Br |
| Cl | CN | Cl | t-Bu | N | Br |
| Cl | CN | Br | H | N | F |
| Cl | CN | Br | Me | N | F |
| Cl | CN | Br | Et | N | F |
| Cl | CN | Br | i-Pr | N | F |
| Cl | CN | Br | t-Bu | N | F |
| Cl | CN | Br | H | N | Cl |
| Cl | CN | Br | Me | N | Cl |
| Cl | CN | Br | Et | N | Cl |
| Cl | CN | Br | i-Pr | N | Cl |
| Cl | CN | Br | t-Bu | N | Cl |
| Cl | CN | Br | H | N | Br |
| Cl | CN | Br | Me | N | Br |
| Cl | CN | Br | Et | N | Br |
| Cl | CN | Br | i-Pr | N | Br |
| Cl | CN | Br | t-Bu | N | Br |

TABLE 2-continued

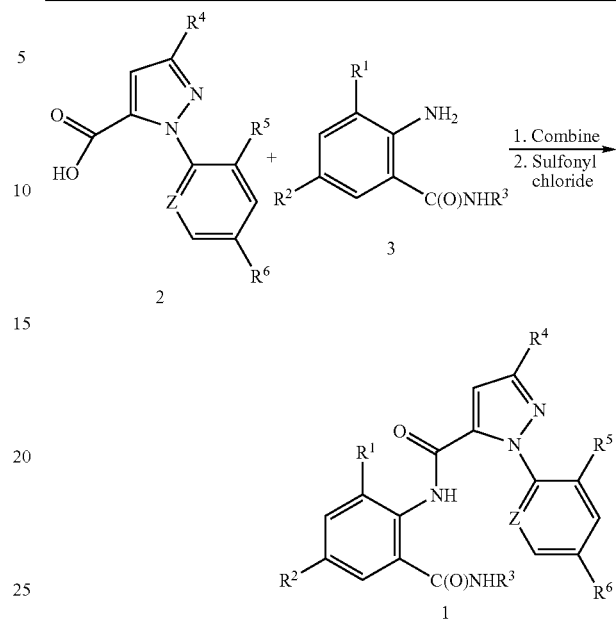

| R¹ | R² | R⁴ | R³ | Z | R⁵ |
|---|---|---|---|---|---|
| Cl | CN | OCH₂CF₃ | H | N | F |
| Cl | CN | OCH₂CF₃ | Me | N | F |
| Cl | CN | OCH₂CF₃ | Et | N | F |
| Cl | CN | OCH₂CF₃ | i-Pr | N | F |
| Cl | CN | OCH₂CF₃ | t-Bu | N | F |
| Cl | CN | OCH₂CF₃ | H | N | Cl |
| Cl | CN | OCH₂CF₃ | Me | N | Cl |
| Cl | CN | OCH₂CF₃ | Et | N | Cl |
| Cl | CN | OCH₂CF₃ | i-Pr | N | Cl |
| Cl | CN | OCH₂CF₃ | t-Bu | N | Cl |
| Cl | CN | OCH₂CF₃ | H | N | Br |
| Cl | CN | OCH₂CF₃ | Me | N | Br |
| Cl | CN | OCH₂CF₃ | Et | N | Br |
| Cl | CN | OCH₂CF₃ | i-Pr | N | Br |
| Cl | CN | OCH₂CF₃ | t-Bu | N | Br |
| Cl | CN | OCHF₂ | H | N | F |
| Cl | CN | OCHF₂ | Me | N | F |
| Cl | CN | OCHF₂ | Et | N | F |
| Cl | CN | OCHF₂ | i-Pr | N | F |
| Cl | CN | OCHF₂ | t-Bu | N | F |
| Cl | CN | OCHF₂ | H | N | Cl |
| Cl | CN | OCHF₂ | Me | N | Cl |
| Cl | CN | OCHF₂ | Et | N | Cl |
| Cl | CN | OCHF₂ | i-Pr | N | Cl |
| Cl | CN | OCHF₂ | t-Bu | N | Cl |
| Cl | CN | OCHF₂ | H | N | Br |
| Cl | CN | OCHF₂ | Me | N | Br |
| Cl | CN | OCHF₂ | Et | N | Br |
| Cl | CN | OCHF₂ | i-Pr | N | Br |
| Cl | CN | OCHF₂ | t-Bu | N | Br |
| Cl | Cl | CF₃ | H | CH | F |
| Cl | Cl | CF₃ | Me | CH | F |
| Cl | Cl | CF₃ | Et | CH | F |
| Cl | Cl | CF₃ | i-Pr | CH | F |
| Cl | Cl | CF₃ | t-Bu | CH | F |
| Cl | Cl | CF₃ | H | CH | Cl |
| Cl | Cl | CF₃ | Me | CH | Cl |
| Cl | Cl | CF₃ | Et | CH | Cl |
| Cl | Cl | CF₃ | i-Pr | CH | Cl |
| Cl | Cl | CF₃ | t-Bu | CH | Cl |
| Cl | Cl | CF₃ | H | CH | Br |
| Cl | Cl | CF₃ | Me | CH | Br |
| Cl | Cl | CF₃ | Et | CH | Br |
| Cl | Cl | CF₃ | i-Pr | CH | Br |
| Cl | Cl | CF₃ | t-Bu | CH | Br |
| Cl | Cl | Cl | H | CH | F |
| Cl | Cl | Cl | Me | CH | F |

TABLE 2-continued

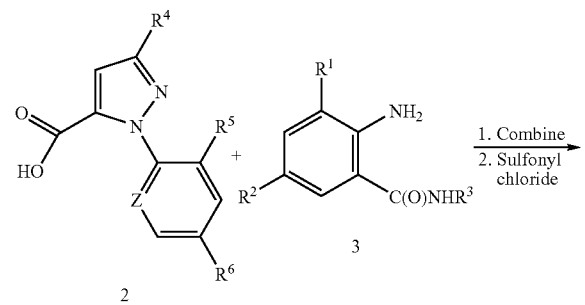

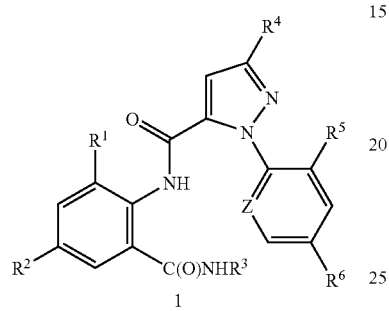

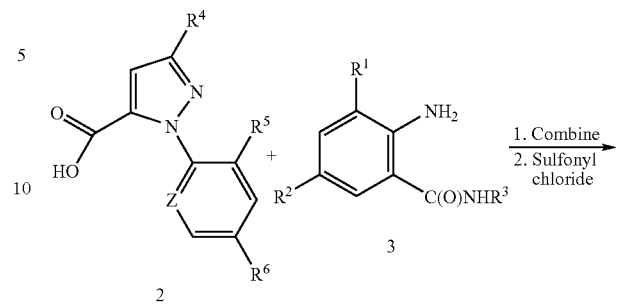

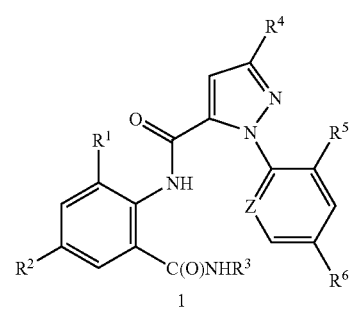

| R¹ | R² | R⁴ | R³ | Z | R⁵ | R¹ | R² | R⁴ | R³ | Z | R⁵ |
|---|---|---|---|---|---|---|---|---|---|---|---|
| Cl | Cl | Cl | Et | CH | F | Cl | Br | CF₃ | t-Bu | CH | F |
| Cl | Cl | Cl | i-Pr | CH | F | Cl | Br | CF₃ | H | CH | Cl |
| Cl | Cl | Cl | t-Bu | CH | F | Cl | Br | CF₃ | Me | CH | Cl |
| Cl | Cl | Cl | H | CH | Cl | Cl | Br | CF₃ | Et | CH | Cl |
| Cl | Cl | Cl | Me | CH | Cl | Cl | Br | CF₃ | i-Pr | CH | Cl |
| Cl | Cl | Cl | Et | CH | Cl | Cl | Br | CF₃ | t-Bu | CR | Cl |
| Cl | Cl | Cl | i-Pr | CH | Cl | Cl | Br | CF₃ | H | CH | Br |
| Cl | Cl | Cl | t-Bu | CH | Cl | Cl | Br | CF₃ | Me | CH | Br |
| Cl | Cl | Cl | H | CH | Br | Cl | Br | CF₃ | Et | CH | Br |
| Cl | Cl | Cl | Me | CH | Br | Cl | Br | CF₃ | i-Pr | CH | Br |
| Cl | Cl | Cl | Et | CH | Br | Cl | Br | CF₃ | t-Bu | CH | Br |
| Cl | Cl | Cl | i-Pr | CH | Br | Cl | Br | Cl | H | CH | F |
| Cl | Cl | Cl | t-Bu | CH | Br | Cl | Br | Cl | Me | CH | F |
| Cl | Cl | Br | H | CH | F | Cl | Br | Cl | Et | CH | F |
| Cl | Cl | Br | Me | CH | F | Cl | Br | Cl | i-Pr | CH | F |
| Cl | Cl | Br | Et | CH | F | Cl | Br | Cl | t-Bu | CH | F |
| Cl | Cl | Br | i-Pr | CH | F | Cl | Br | Cl | H | CH | Cl |
| Cl | Cl | Br | t-Bu | CH | F | Cl | Br | Cl | Me | CH | Cl |
| Cl | Cl | Br | H | CH | Cl | Cl | Br | Cl | Et | CH | Cl |
| Cl | Cl | Br | Me | CH | Cl | Cl | Br | Cl | i-Pr | CH | Cl |
| Cl | Cl | Br | Et | CH | Cl | Cl | Br | Cl | t-Bu | CH | Cl |
| Cl | Cl | Br | i-Pr | CH | Cl | Cl | Br | Cl | H | CH | Br |
| Cl | Cl | Br | t-Bu | CH | Cl | Cl | Br | Cl | Me | CH | Br |
| Cl | Cl | Br | H | CH | Br | Cl | Br | Cl | Et | CH | Br |
| Cl | Cl | Br | Me | CH | Br | Cl | Br | Cl | i-Pr | CH | Br |
| Cl | Cl | Br | Et | CE | Br | Cl | Br | Cl | t-Bu | CH | Br |
| Cl | Cl | Br | i-Pr | CH | Br | Cl | Br | Br | H | CH | F |
| Cl | Cl | Br | t-Bu | CH | Br | Cl | Br | Br | Me | CH | F |
| Cl | Cl | OCH₂CF₃ | H | CH | F | Cl | Br | Br | Et | CH | F |
| Cl | Cl | OCH₂CF₃ | Me | CH | F | Cl | Br | Br | i-Pr | CH | F |
| Cl | Cl | OCH₂CF₃ | Et | CH | F | Cl | Br | Br | t-Bu | CH | F |
| Cl | Cl | OCH₂CF₃ | i-Pr | CH | F | Cl | Br | Br | H | CH | Cl |
| Cl | Cl | OCH₂CF₃ | t-Bu | CH | F | Cl | Br | Br | Me | CH | Cl |
| Cl | Cl | OCH₂CF₃ | H | CH | Cl | Cl | Br | Br | Et | CH | Cl |
| Cl | Cl | OCH₂CF₃ | Me | CH | Cl | Cl | Br | Br | i-Pr | CH | Cl |
| Cl | Cl | OCH₂CF₃ | Et | CH | Cl | Cl | Br | Br | t-Bu | CH | Cl |
| Cl | Cl | OCH₂CF₃ | i-Pr | CH | Cl | Cl | Br | Br | H | CH | Br |
| Cl | Cl | OCH₂CF₃ | t-Bu | CH | Cl | Cl | Br | Br | Me | CH | Br |
| Cl | Cl | OCH₂CF₃ | H | CH | Br | Cl | Br | Br | Et | CH | Br |
| Cl | Cl | OCH₂CF₃ | Me | CH | Br | Cl | Br | Br | i-Pr | CH | Br |
| Cl | Cl | OCH₂CF₃ | Et | CH | Br | Cl | Br | Br | t-Bu | CH | Br |
| Cl | Cl | OCH₂CF₃ | i-Pr | CH | Br | Cl | Br | OCH₂CF₃ | H | CH | F |
| Cl | Cl | OCH₂CF₃ | t-Bu | CH | Br | Cl | Br | OCH₂CF₃ | Me | CH | F |
| Cl | Br | CF₃ | H | CH | F | Cl | Br | OCH₂CF₃ | Et | CH | F |
| Cl | Br | CF₃ | Me | CH | F | Cl | Br | OCH₂CF₃ | i-Pr | CH | F |
| Cl | Br | CF₃ | Et | CH | F | Cl | Br | OCH₂CF₃ | t-Bu | CH | F |
| Cl | Br | CF₃ | i-Pr | CH | F | Cl | Br | OCH₂CF₃ | H | CH | Cl |

TABLE 2-continued

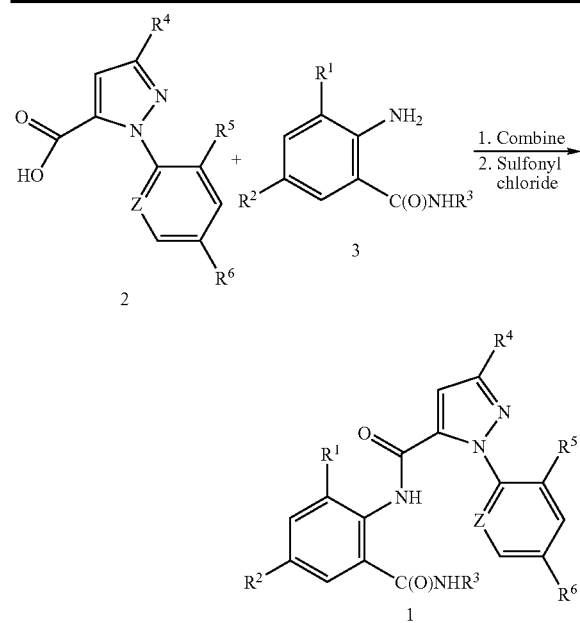

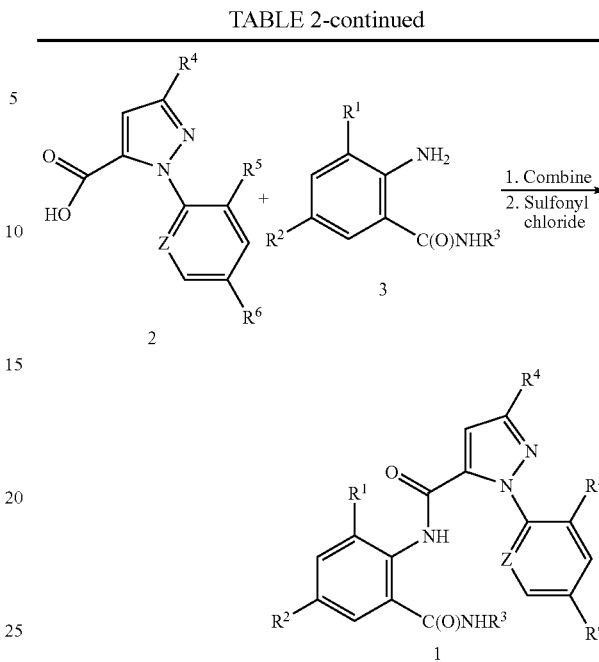

| R¹ | R² | R⁴ | R³ | Z | R⁵ |
|---|---|---|---|---|---|
| Cl | Br | OCH₂CF₃ | Me | CH | Cl |
| Cl | Br | OCH₂CF₃ | Et | CH | Cl |
| Cl | Br | OCH₂CF₃ | i-Pr | CH | Cl |
| Cl | Br | OCH₂CF₃ | t-Bu | CH | Cl |
| Cl | Br | OCH₂CF₃ | H | CH | Br |
| Cl | Br | OCH₂CF₃ | Me | CH | Br |
| Cl | Br | OCH₂CF₃ | Et | CH | Br |
| Cl | Br | OCH₂CF₃ | i-Pr | CH | Br |
| Cl | Br | OCH₂CF₃ | t-Bu | CH | Br |
| Cl | I | CF₃ | H | CH | F |
| Cl | I | CF₃ | Me | CH | F |
| Cl | I | CF₃ | Et | CH | F |
| Cl | I | CF₃ | i-Pr | CH | F |
| Cl | I | CF₃ | t-Bu | CH | F |
| Cl | I | CF₃ | H | CH | Cl |
| Cl | I | CF₃ | Me | CH | Cl |
| Cl | I | CF₃ | Et | CH | Cl |
| Cl | I | CF₃ | i-Pr | CH | Cl |
| Cl | I | CF₃ | t-Bu | CH | Cl |
| Cl | I | CF₃ | H | CH | Br |
| Cl | I | CF₃ | Me | CH | Br |
| Cl | I | CF₃ | Et | CH | Br |
| Cl | I | CF₃ | i-Pr | CH | Br |
| Cl | I | CF₃ | t-Bu | CH | Br |
| Cl | I | Cl | H | CH | F |
| Cl | I | Cl | Me | CH | F |
| Cl | I | Cl | Et | CH | F |
| Cl | I | Cl | i-Pr | CH | F |
| Cl | I | Cl | t-Bu | CH | F |
| Cl | I | Cl | H | CH | Cl |
| Cl | I | Cl | Me | CH | Cl |
| Cl | I | Cl | Et | CH | Cl |
| Cl | I | Cl | i-Pr | CH | Cl |
| Cl | I | Cl | t-Bu | CH | Cl |
| Cl | I | Cl | H | CH | Br |
| Cl | I | Cl | Me | CH | Br |
| Cl | I | Cl | Et | CH | Br |
| Cl | I | Cl | i-Pr | CH | Br |
| Cl | I | Cl | t-Bu | CH | Br |
| Cl | I | Br | H | CH | F |
| Cl | I | Br | Me | CH | F |
| Cl | I | Br | Et | CH | F |
| Cl | I | Br | i-Pr | CH | F |
| Cl | I | Br | t-Bu | CH | F |
| Cl | I | Br | H | CH | Cl |
| Cl | I | Br | Me | CH | Cl |
| Cl | I | Br | Et | CH | Cl |
| Cl | I | Br | i-Pr | CH | Cl |
| Cl | I | Br | t-Bu | CH | Cl |
| Cl | I | Br | H | CH | Br |
| Cl | I | Br | Me | CH | Br |
| Cl | I | Br | Et | CH | Br |
| Cl | I | Br | i-Pr | CH | Br |
| Cl | I | Br | t-Bu | CH | Br |
| Cl | I | OCH₂CF₃ | H | CH | F |
| Cl | I | OCH₂CF₃ | Me | CH | F |
| Cl | I | OCH₂CF₃ | Et | CH | F |
| Cl | I | OCH₂CF₃ | i-Pr | CH | F |
| Cl | I | OCH₂CF₃ | t-Bu | CH | F |
| Cl | I | OCH₂CF₃ | H | CH | Cl |
| Cl | I | OCH₂CF₃ | Me | CH | Cl |
| Cl | I | OCH₂CF₃ | Et | CH | Cl |
| Cl | I | OCH₂CF₃ | i-Pr | CH | Cl |
| Cl | I | OCH₂CF₃ | t-Bu | CH | Cl |
| Cl | I | OCH₂CF₃ | H | CH | Br |
| Cl | I | OCH₂CF₃ | Me | CH | Br |
| Cl | I | OCH₂CF₃ | Et | CH | Br |
| Cl | I | OCH₂CF₃ | i-Pr | CH | Br |
| Cl | I | OCH₂CF₃ | t-Bu | CH | Br |
| Cl | Cl | OCHF₂ | H | CH | F |
| Cl | Cl | OCHF₂ | Me | CH | F |
| Cl | Cl | OCHF₂ | Et | CH | F |
| Cl | Cl | OCHF₂ | i-Pr | CH | F |
| Cl | Cl | OCHF₂ | t-Bu | CH | F |
| Cl | Cl | OCHF₂ | H | CH | Cl |
| Cl | Cl | OCHF₂ | Me | CH | Cl |
| Cl | Cl | OCHF₂ | Et | CH | Cl |
| Cl | Cl | OCHF₂ | i-Pr | CH | Cl |
| Cl | Cl | OCHF₂ | t-Bu | CH | Cl |
| Cl | Cl | OCHF₂ | H | CH | Br |
| Cl | Cl | OCHF₂ | Me | CH | Br |
| Cl | Cl | OCHF₂ | Et | CH | Br |
| Cl | Cl | OCHF₂ | i-Pr | CH | Br |
| Cl | Cl | OCHF₂ | t-Bu | CH | Br |
| Cl | Br | OCHF₂ | H | CH | F |
| Cl | Br | OCHF₂ | Me | CH | F |
| Cl | Br | OCHF₂ | Et | CH | F |
| Cl | Br | OCHF₂ | i-Pr | CH | F |
| Cl | Br | OCHF₂ | t-Bu | CH | F |
| Cl | Br | OCHF₂ | H | CH | Cl |
| Cl | Br | OCHF₂ | Me | CH | Cl |
| Cl | Br | OCHF₂ | Et | CH | Cl |
| Cl | Br | OCHF₂ | i-Pr | CH | Cl |
| Cl | Br | OCHF₂ | t-Bu | CH | Cl |

TABLE 2-continued

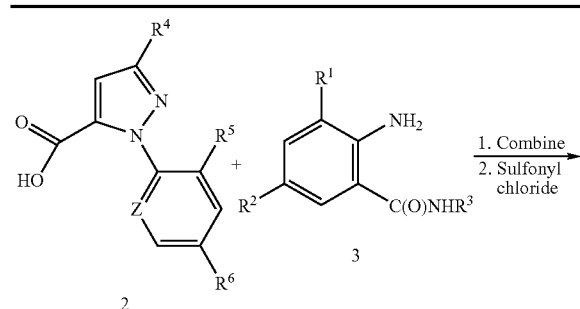

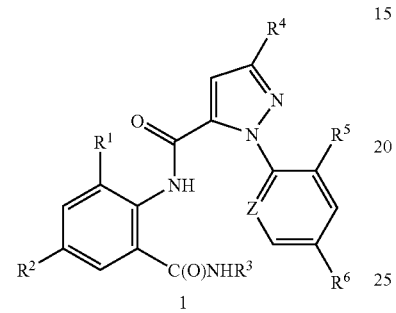

| R¹ | R² | R⁴ | R³ | Z | R⁵ |
|----|----|----|----|----|----|
| Cl | Br | OCHF₂ | H | CH | Br |
| Cl | Br | OCHF₂ | Me | CH | Br |
| Cl | Br | OCHF₂ | Et | CH | Br |
| Cl | Br | OCHF₂ | i-Pr | CH | Br |
| Cl | Br | OCHF₂ | t-Bu | CH | Br |
| Cl | I | OCHF₂ | H | CH | F |
| Cl | I | OCHF₂ | Me | CH | F |
| Cl | I | OCHF₂ | Et | CH | F |
| Cl | I | OCHF₂ | i-Pr | CH | F |
| Cl | I | OCHF₂ | t-Bu | CH | F |
| Cl | I | OCHF₂ | H | CH | Cl |
| Cl | I | OCHF₂ | Me | CH | Cl |
| Cl | I | OCHF₂ | Et | CH | Cl |
| Cl | I | OCHF₂ | i-Pr | CH | Cl |
| Cl | I | OCHF₂ | t-Bu | CH | Cl |
| Cl | I | OCHF₂ | H | CH | Br |
| Cl | I | OCHF₂ | Me | CH | Br |
| Cl | I | OCHF₂ | Et | CH | Br |
| Cl | I | OCHF₂ | i-Pr | CH | Br |
| Cl | I | OCHF₂ | t-Bu | CH | Br |
| Cl | CN | CF₃ | H | CH | F |
| Cl | CN | CF₃ | Me | CH | F |
| Cl | CN | CF₃ | Et | CH | F |
| Cl | CN | CF₃ | i-Pr | CH | F |
| Cl | CN | CF₃ | t-Bu | CH | F |
| Cl | CN | CF₃ | H | CH | Cl |
| Cl | CN | CF₃ | Me | CH | Cl |
| Cl | CN | CF₃ | Et | CH | Cl |
| Cl | CN | CF₃ | i-Pr | CH | Cl |
| Cl | CN | CF₃ | t-Bu | CH | Cl |
| Cl | CN | CF₃ | H | CH | Br |
| Cl | CN | CF₃ | Me | CH | Br |
| Cl | CN | CF₃ | Et | CH | Br |
| Cl | CN | CF₃ | i-Pr | CH | Br |
| Cl | CN | CF₃ | t-Bu | CH | Br |
| Cl | CN | Cl | H | CH | F |
| Cl | CN | Cl | Me | CH | F |
| Cl | CN | Cl | Et | CH | F |
| Cl | CN | Cl | i-Pr | CH | F |
| Cl | CN | Cl | t-Bu | CH | F |
| Cl | CN | Cl | H | CH | Cl |
| Cl | CN | Cl | Me | CH | Cl |
| Cl | CN | Cl | Et | CH | Cl |
| Cl | CN | Cl | i-Pr | CH | Cl |
| Cl | CN | Cl | t-Bu | CH | Cl |
| Cl | CN | Cl | H | CH | Br |
| Cl | CN | Cl | Me | CH | Br |

TABLE 2-continued

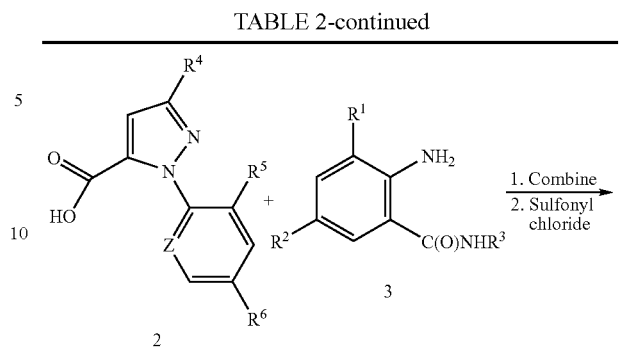

| R¹ | R² | R⁴ | R³ | Z | R⁵ |
|----|----|----|----|----|----|
| Cl | CN | Cl | Et | CH | Br |
| Cl | CN | Cl | i-Pr | CH | Br |
| Cl | CN | Cl | t-Bu | CH | Br |
| Cl | CN | Br | H | CH | F |
| Cl | CN | Br | Me | CH | F |
| Cl | CN | Br | Et | CH | F |
| Cl | CN | Br | i-Pr | CH | F |
| Cl | CN | Br | t-Bu | CH | F |
| Cl | CN | Br | H | CH | Cl |
| Cl | CN | Br | Me | CH | Cl |
| Cl | CN | Br | Et | CH | Cl |
| Cl | CN | Br | i-Pr | CH | Cl |
| Cl | CN | Br | t-Bu | CH | Cl |
| Cl | CN | Br | H | CH | Br |
| Cl | CN | Br | Me | CH | Br |
| Cl | CN | Br | Et | CH | Br |
| Cl | CN | Br | i-Pr | CH | Br |
| Cl | CN | Br | t-Bu | CH | Br |
| Cl | CN | OCH₂CF₃ | H | CH | F |
| Cl | CN | OCH₂CF₃ | Me | CH | F |
| Cl | CN | OCH₂CF₃ | Et | CH | F |
| Cl | CN | OCH₂CF₃ | i-Pr | CH | F |
| Cl | CN | OCH₂CF₃ | t-Bu | CH | F |
| Cl | CN | OCH₂CF₃ | H | CH | Cl |
| Cl | CN | OCH₂CF₃ | Me | CH | Cl |
| Cl | CN | OCH₂CF₃ | Et | CH | Cl |
| Cl | CN | OCH₂CF₃ | i-Pr | CH | Cl |
| Cl | CN | OCH₂CF₃ | t-Bu | CH | Cl |
| Cl | CN | OCH₂CF₃ | H | CH | Br |
| Cl | CN | OCH₂CF₃ | Me | CH | Br |
| Cl | CN | OCH₂CF₃ | Et | CH | Br |
| Cl | CN | OCH₂CF₃ | i-Pr | CH | Br |
| Cl | CN | OCH₂CF₃ | t-Bu | CH | Br |
| Cl | CN | OCHF₂ | H | CH | F |
| Cl | CN | OCHF₂ | Me | CH | F |
| Cl | CN | OCHF₂ | Et | CH | F |
| Cl | CN | OCHF₂ | i-Pr | CH | F |
| Cl | CN | OCHF₂ | t-Bu | CH | F |
| Cl | CN | OCHF₂ | H | CH | Cl |
| Cl | CN | OCHF₂ | Me | CH | Cl |
| Cl | CN | OCHF₂ | Et | CH | Cl |
| Cl | CN | OCHF₂ | i-Pr | CH | Cl |
| Cl | CN | OCHF₂ | t-Bu | CH | Cl |
| Cl | CN | OCHF₂ | H | CH | Br |
| Cl | CN | OCHF₂ | Me | CH | Br |

TABLE 2-continued

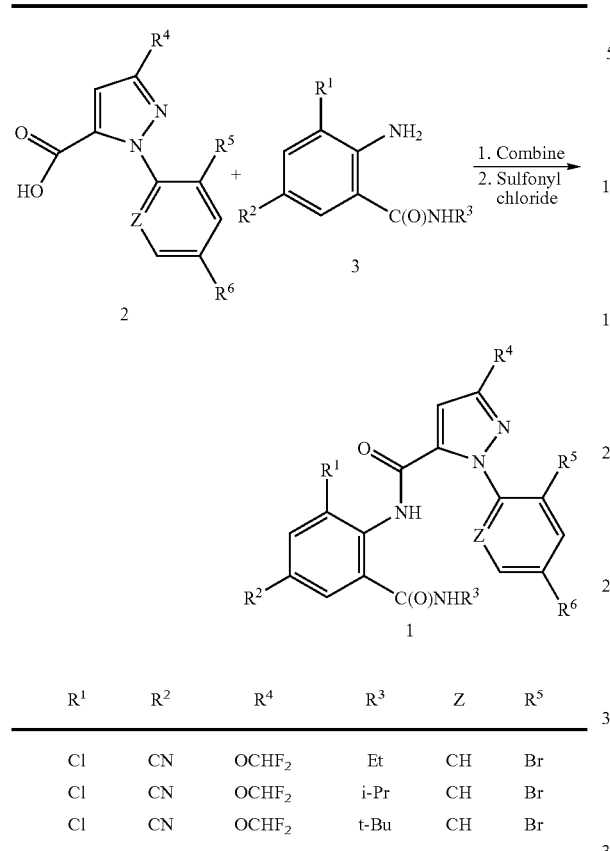

| R¹ | R² | R⁴ | R³ | Z | R⁵ |
|----|----|-----|------|----|----|
| Cl | CN | OCHF₂ | Et | CH | Br |
| Cl | CN | OCHF₂ | i-Pr | CH | Br |
| Cl | CN | OCHF₂ | t-Bu | CH | Br |

What is claimed is:

1. A method for preparing a compound of Formula 1,

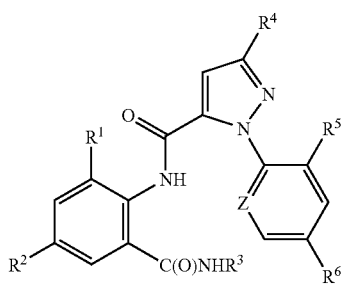

wherein
R¹ is $CH_3$ or Cl;
R² is Br, Cl, I or CN;
R³ is H or $C_1$-$C_4$ alkyl;
R⁴ is Cl, Br, $CF_3$, $OCF_2H$ or $OCH_2CF_3$;
R⁵ is F, Cl or Br;
R⁶ is H, F or Cl;
Z is $CR^7$ or N; and
R⁷ is H, F, Cl or Br; comprising:
combining (1) a carboxylic acid compound of Formula 2,

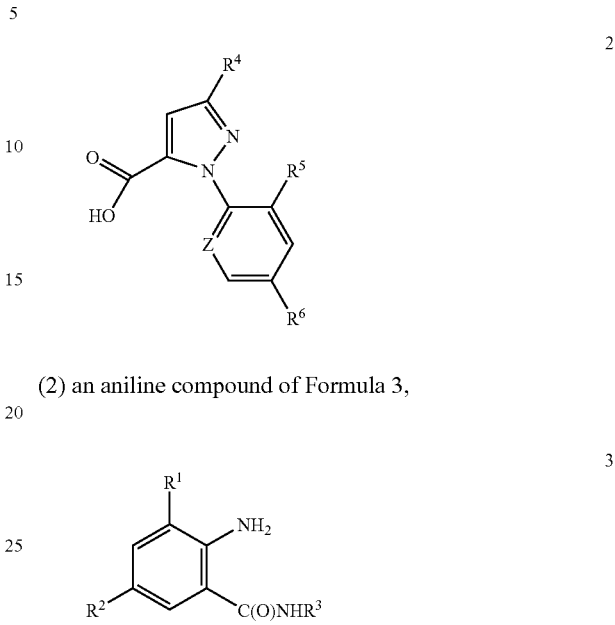

(2) an aniline compound of Formula 3, and (3) a sulfonyl chloride to form the compound of Formula 1.

2. The method of claim 1 wherein the sulfonyl chloride is of Formula 4

$$R^8S(O)_2Cl \qquad 4$$

wherein $R^8$ is $C_1$-$C_4$ alkyl, $C_1$-$C_2$ haloalkyl, or phenyl optionally substituted with 1-3 substituents selected from the group consisting of halogen, $C_1$-$C_3$ alkyl and nitro.

3. The method of claim 2 wherein the sulfonyl chloride is methanesulfonyl chloride.

4. The method of claim 1 wherein the carboxylic acid of Formula 2 is combined with the aniline of Formula 3 to form a mixture, and then the mixture is combined with the sulfonyl chloride.

5. The method of claim 4 wherein a base is combined with the compounds of Formulae 2 and 3 to form the mixture before combining with the sulfonyl chloride.

6. The method of claim 5 wherein the base is selected from tertiary amines.

7. The method of claim 6 wherein the base is selected from optionally substituted pyridines.

8. The method of claim 7 wherein the base is selected from 2-picoline, 3-picoline, 2,6-lutidine and pyridine.

9. The method of claim 8 wherein the sulfonyl chloride is of Formula 4

$$R^8S(O)_2Cl \qquad 4$$

wherein $R^8$ is $C_1$-$C_4$ alkyl, $C_1$-$C_2$ haloalkyl, or phenyl optionally substituted with 1-3 substituents selected from the group consisting of halogen, $C_1$-$C_3$ alkyl and nitro.

10. The method of claim 1 or claim 4 wherein a solvent is combined with the compounds of Formulae 2 and 3 and the sulfonyl chloride.

11. The method of claim 10 wherein the solvent is acetonitrile.

12. A compound of Formula 3

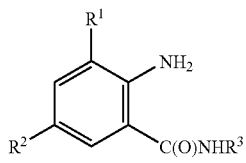

wherein $R^1$ is $CH_3$ or Cl;

$R^2$ is Br, Cl, I or CN; and $R^3$ is H or $C_1$-$C_4$ alkyl;

provided that
(a) when $R^1$ and $R^2$ are Cl, then $R^3$ is other than H, $CH_2CH_3$, or $CH(CH_3)CH_2CH_3$;
(b) when $R^1$ is $CH_3$ and $R^2$ is Cl, Br or CN, then $R^3$ is other than $CH_3$ or $CH(CH_3)_2$;
(c) when $R^1$ is Cl and $R^2$ is Cl or Br, then $R^3$ is other than H, $CH_3$ or $CH(CH_3)_2$; and
(d) when $R^1$ is $CH_3$ and $R^2$ is CN, then $R_3$ is other than H.

13. A compound of claim 12 wherein $R^1$ is $CH_3$.

14. A compound of claim 13 wherein $R^2$ is Cl and $R^3$ is H.

15. A compound of claim 13 wherein $R^2$ is CN and $R^3$ is $CH_2CH_3$, $CH_2CH_2CH_3$, $CH_2CH_2CH_2CH_3$, $CH_2CH(CH_3)_2$, $CH(CH_3)CH_2CH_3$ or $C(CH_3)_3$.

16. A compound of claim 12 wherein $R^2$ is CN.

* * * * *